United States Patent [19]

Mookherjee et al.

[11] Patent Number: 4,506,104

[45] Date of Patent: Mar. 19, 1985

[54] METHYL SUBSTITUTED PINYL OXOPENTENES, ORGANOLEPTIC USES THEREOF AND PROCESS FOR PREPARING SAME

[75] Inventors: Braja D. Mookherjee, Holmdel; Robert W. Trenkle, Bricktown; Robin K. Wolff, Point Pleasant; Richard M. Boden, Ocean; Takao Yoshida, West Long Branch, all of N.J.

[73] Assignee: International Flvors & Fragrances Inc., New York, N.Y.

[21] Appl. No.: 582,795

[22] Filed: Feb. 23, 1984

Related U.S. Application Data

[60] Division of Ser. No. 496,651, May 20, 1983, , said Ser. No. 396,485, is a continuation-in-part of Ser. No. 362,237, Mar. 26, 1982, Pat. No. 4,428,387.

[51] Int. Cl.$^3$ ............................................. C07C 35/22
[52] U.S. Cl. .................................................... 568/820
[58] Field of Search ........................................ 568/820

Primary Examiner—Werren B. Lone
Attorney, Agent, or Firm—Arthur L. Liberman

[57] ABSTRACT

Described are hydroxy alkenyl bicyclic terpene derivatives useful in perfumery.

4 Claims, 26 Drawing Figures

GLC PROFILE FOR EXAMPLE II.

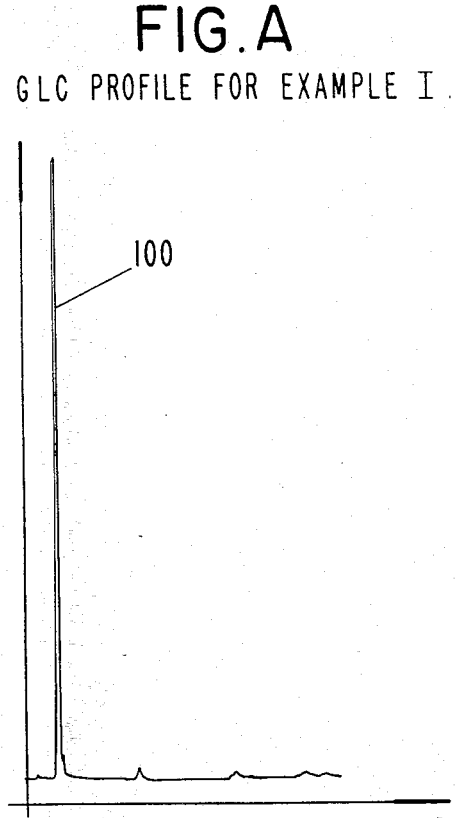
FIG. A
GLC PROFILE FOR EXAMPLE I.
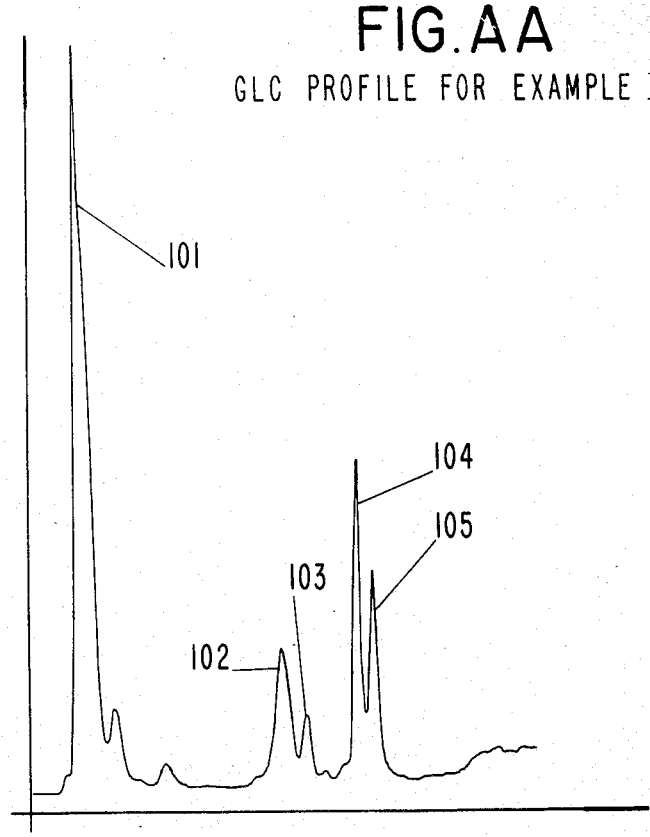
FIG. AA
GLC PROFILE FOR EXAMPLE I.
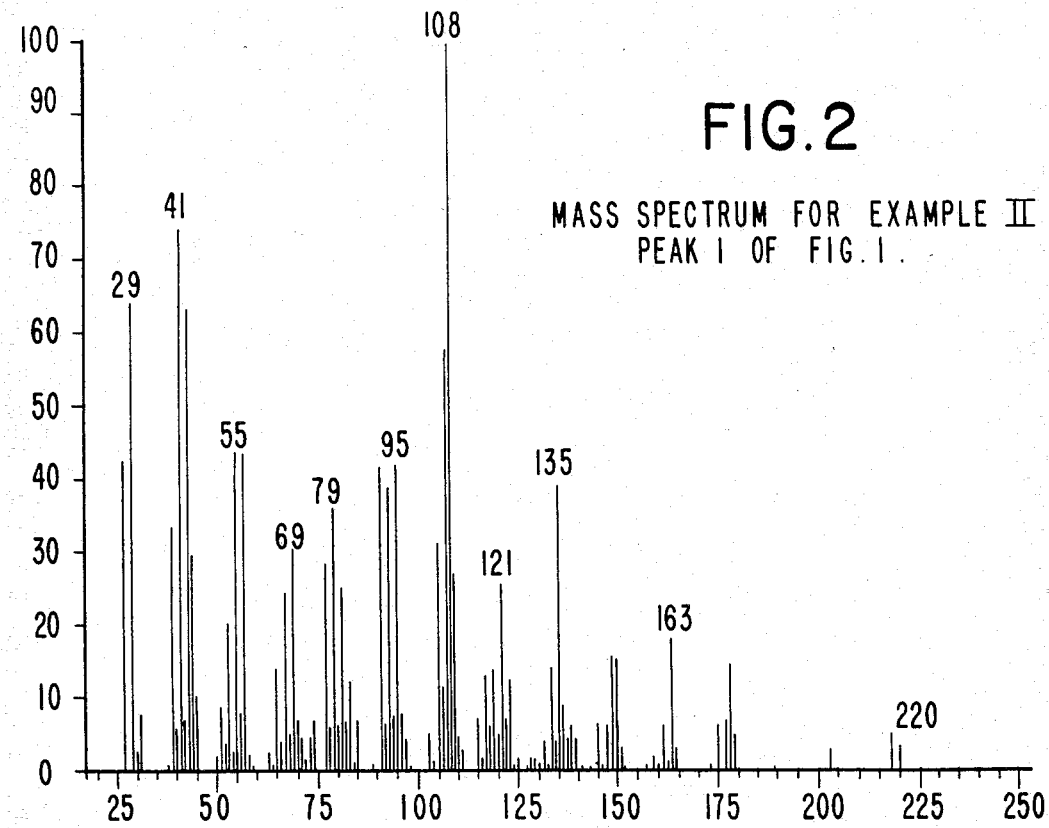
FIG. 2
MASS SPECTRUM FOR EXAMPLE II
PEAK 1 OF FIG. 1.

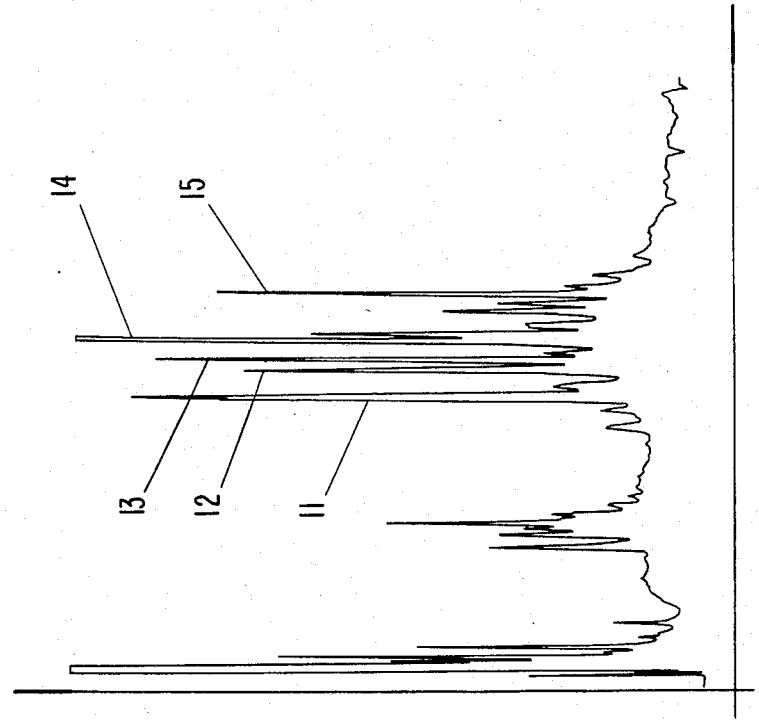
FIG.8 GLC PROFILE FOR EXAMPLE IV.
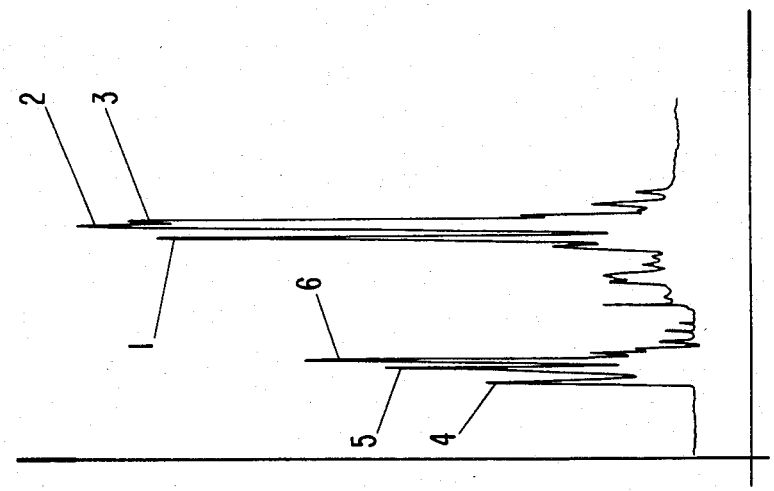
FIG.1 GLC PROFILE FOR EXAMPLE II.

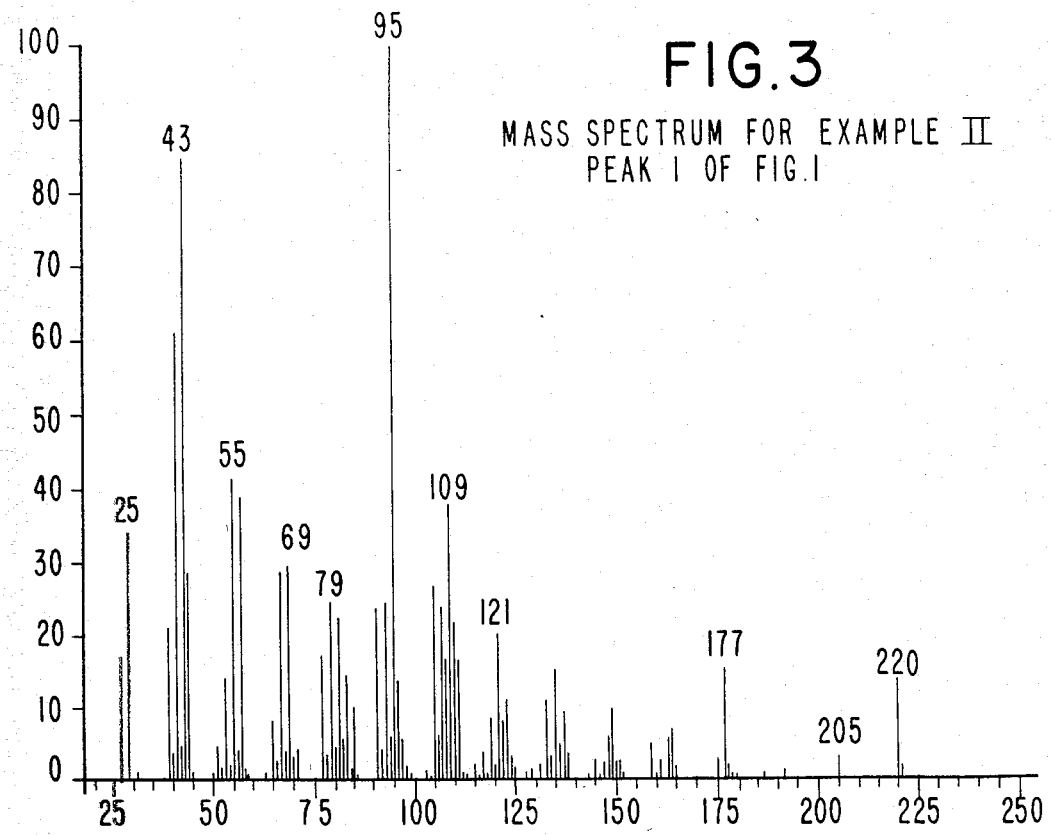
FIG.3
MASS SPECTRUM FOR EXAMPLE II PEAK I OF FIG.I
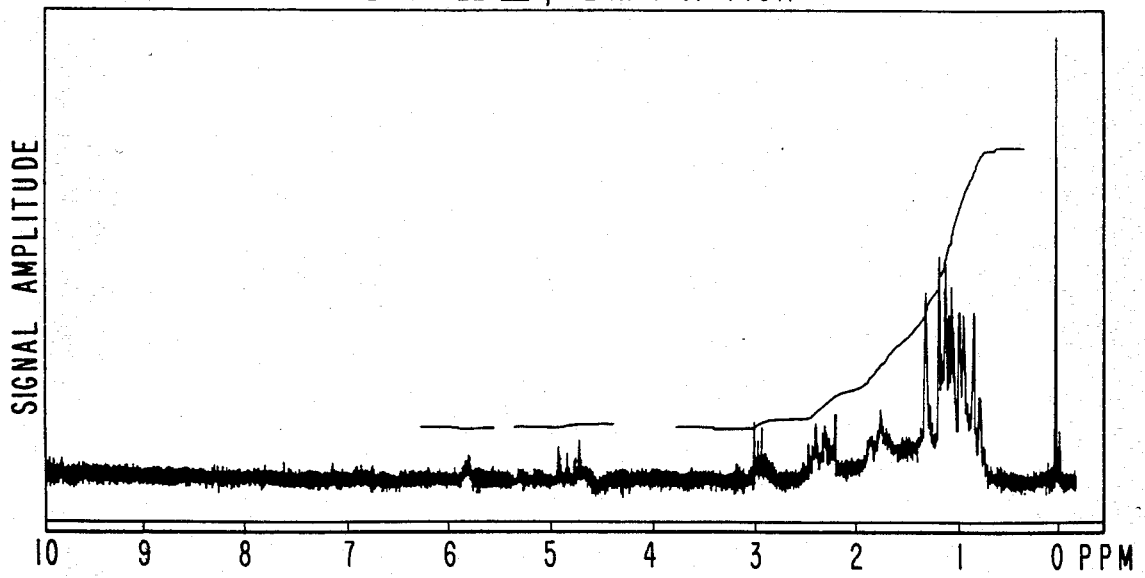

NMR SPECTRUM FOR EXAMPLE II, PEAK 3 OF FIG. I

IR SPECTRUM FOR EXAMPLE II, PEAK I OF FIG. I

IR SPECTRUM FOR EXAMPLE II, PEAK 3 OF FIG.1

MASS SPECTRUM FOR EXAMPLE IV, PEAK 15 OF FIG.8

FIG. 10
NMR SPECTRUM FOR PEAK 15 OF FIG. 8 FOR EXAMPLE IV.
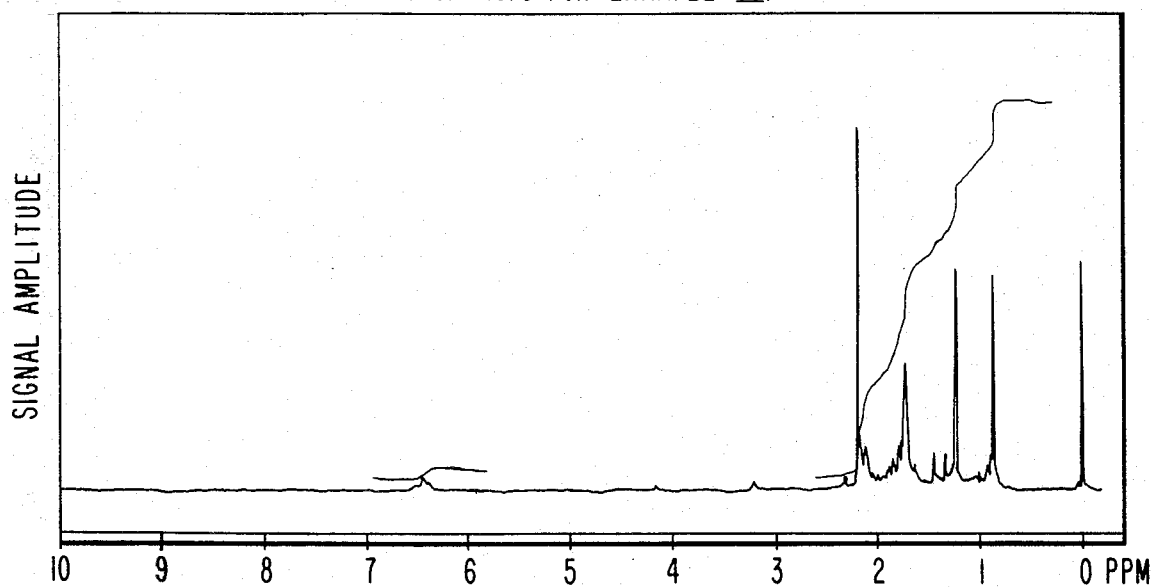
FIG.11
GLC PROFILE FOR EXAMPLE V.
CRUDE A
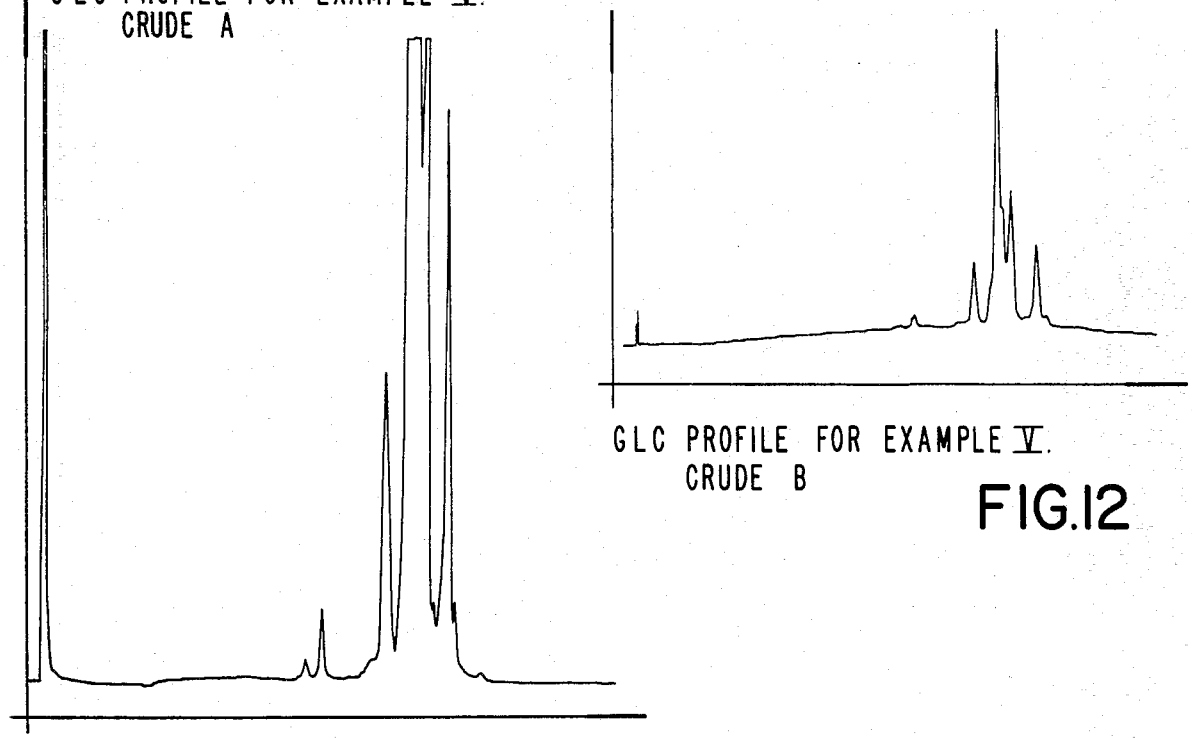
GLC PROFILE FOR EXAMPLE V.
CRUDE B
FIG.12

GLC PROFILE FOR FRACTION 6 OF EXAMPLE V-B.

GLC PROFILE FOR FRACTION 17 OF EXAMPLE V.

NMR SPECTRUM FOR PEAK 20 OF FIG. 20 FOR EXAMPLE V.

NMR SPECTRUM FOR PEAK 21 OF FIG. 13 FOR EXAMPLE V.

IR SPECTRUM FOR EXAMPLE V. (CRUDE B).

GLC PROFILE FOR EXAMPLE V-A

GLC PROFILE FOR EXAMPLE V-A FRACTION 3

GLC PROFILE FOR EXAMPLE V-A

NMR SPECTRUM FOR PEAK 52 OF FIG.19 FOR EXAMPLE V-A.

IR SPECTRUM FOR PEAK 52 OF FIG.19 OF EXAMPLE V-A

NMR SPECTRUM FOR PEAK 62 OF FIG. 22 FOR EXAMPLE V-B

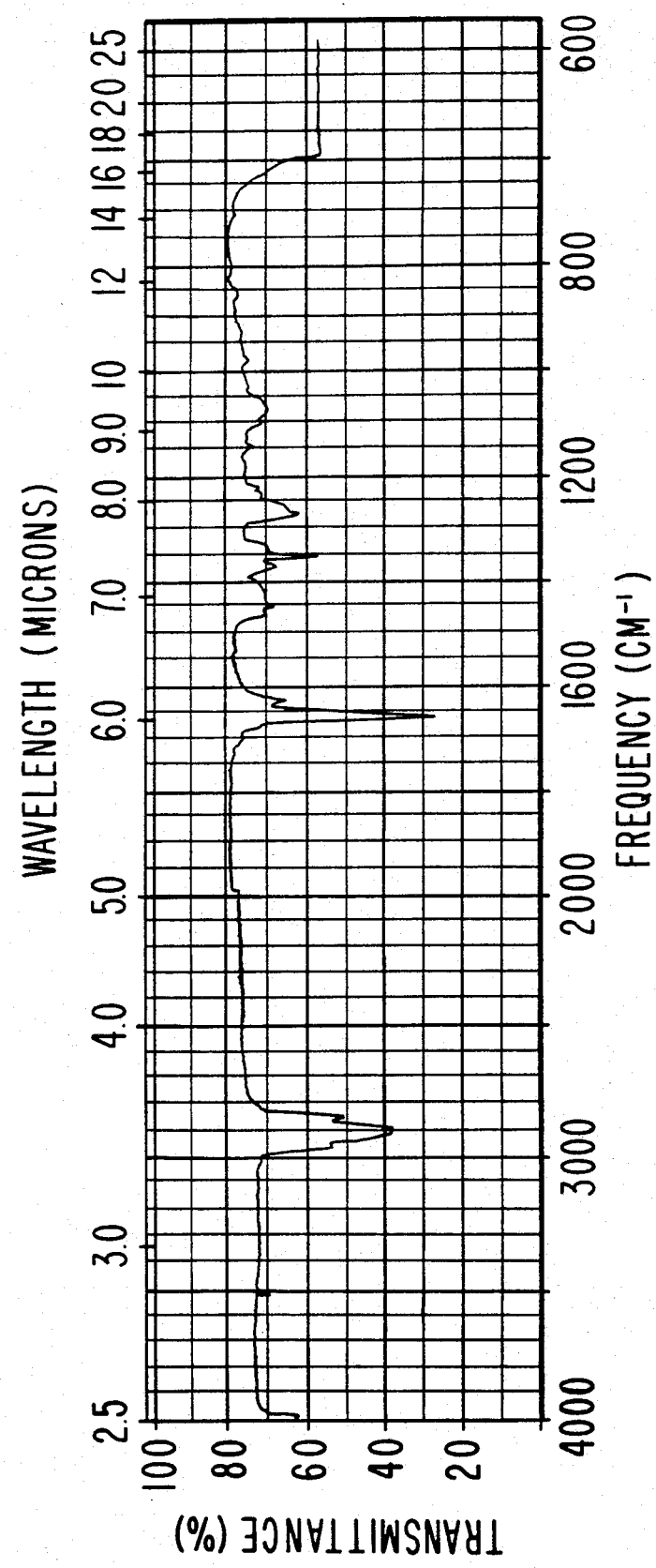

METHYL SUBSTITUTED PINYL OXOPENTENES, ORGANOLEPTIC USES THEREOF AND PROCESS FOR PREPARING SAME

This is a divisional of application Ser. No. 496,651, filed 5-20-83 which in turn is a stream line divisional of U.S. Letters Patent Ser. No. 396,485, filed 7-8-82 which issued on 1-3-84 as U.S. Letters Patent Ser. No. 4,424,378, which in turn is a continuation in part of U.S. Letters Patent Ser. No. 362,237 filed 3-26-82 which issued on 1-31-83 as U.S. Letters Patent No. 4,428,387.

BACKGROUND OF THE INVENTION

This invention relates to the use of novel methyl substituted pinyl oxopentenes defined according to the generic structure:

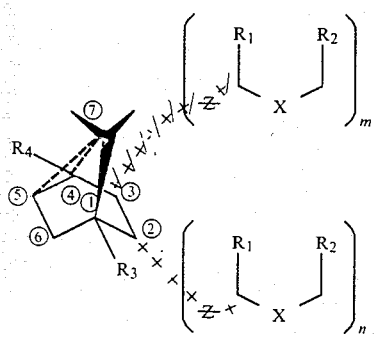

and the generic structure:

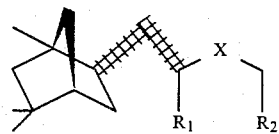

wherein Z represents methylidene defined according to the structure:

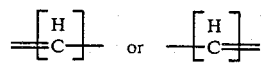

ethylidene defined according to the structure:

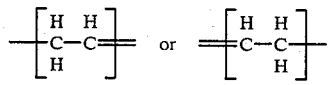

or ethylenyl defined according to the structure:

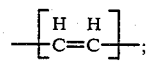

wherein one of the dashed lines represents a carbon-carbon single bond and the other of the dashed lines represents no bond; wherein n is 0 or 1 and m is 0 or 1 with the sum of n+m being equal to 1; wherein X represents carbinol having the structure:

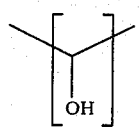

or ketone having the structure:

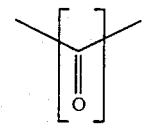

wherein $R_1$, $R_2$, $R_3$ and $R_4$ represents hydrogen or methyl; wherein one of the lines:

++++ represents a carbon-carbon single bond and the other of the lines:

++++ represents a carbon-carbon single bond or a carbon-carbon double bond; wherein one of the lines:

/+/+/+/+/+/ represents a carbon-carbon single bond and the other of the lines:

/+/+/+/+/+/ represents a carbon-carbon single bond or a carbon-carbon double bond; with the provisos that:

(i) when $R_3$ and $R_4$ are each hydrogen, the dashed line at the 7-5 position is a carbon-carbon single bond; n=0 and m is 1; Z represents ethylidene having the structure:

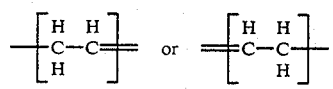

or ethylenyl having the structure:

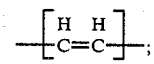

(ii) when one of $R_3$ or $R_4$ is methyl, then either the dashed line at the 7-5 position or the dashed line at the 7-4 position is a carbon-carbon single bond; and Z represents methylidene defined according to the structure:

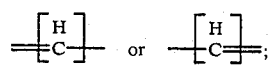

(iii) when $R_3$ is methyl, then n is 1 and m is 0 and $R_4$ is hydrogen; and (iv) when $R_4$ is methyl, then $R_3$ is hydrogen, n is 0 and m is 1;

and wherein one of the lines:

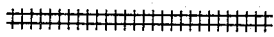

represents a carbon-carbon double bond and the other of the line:

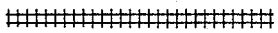

represents a carbon-carbon single bond; and uses thereof in augmenting or enhancing the aroma or taste of consumable materials.

Materials which can provide sandalwood-like, urine-like and musky aromas with floral and muguet undertones are desirable and are known in the art of perfumery. Many of the natural materials which provide such fragrances and such desired nuances to perfumery compositions and perfumed articles are high in cost, vary in quality from one batch to another and/or are generally subject to the usual variations of natural products.

By the same token, materials which can provide ionone-like, raspberry-like, oriental, floral, violet, musky and fruity aromas with sweet, ionone-like, raspberry, fruity and lactonic tastes are desirable and are well known in the art of flavoring for foodstuffs, toothpastes, chewing gums, medicinal products and chewing tobaccos. Many of the natural materials which provide such flavor notes and contribute such desired nuances to flavor and to compositions are high in cost, vary in quality from one batch to another and/or are generally subject to the usual variations of natural products.

By the same token, materials which can provide sweet, woody, oriental, ionone-like, sandalwood-like, patchouli-like and cigar box-like aroma and taste nuances to smoking tobacco or smoking tobacco aritcle components both prior to smoking and on smoking in the main stream and in the side stream are highly desirable and are well known in the art of flavoring for smoking tobacco and components for smoking tobacco articles such as filters and wrappers. Many of the natural materials which provide such aroma and taste nuances and contribute the desired nuances to tobacco flavoring compositions are high in cost, vary in quality from one batch to another and/or are generally subject to the usual variations of natural products.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product, for example, blackberry, peach and tropical fruit flavored foodstuffs. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is particularly noticeable in products having blackberry, peach and tropical fruit characteristics particularly.

Even more desirable are products which can serve to substitute for difficult to obtain natural perfumery oils and, at the same time, substitute for natural flavoring ingredients in foodstuffs, chewing gums, medicinal products, toothpastes, chewing tobaccos, and smoking tobaccos.

Pinyl pentenol derivatives are known in the art for having sandalwood aromas. Thus, the compound having the structure:

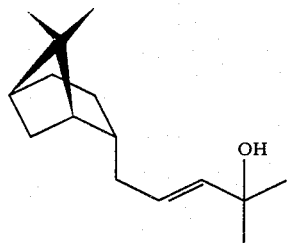

is shown to be prepared according to German Offenlegungsschrift No. 2708048 which, generically, discloses synthesis of compounds defined according to the structure:

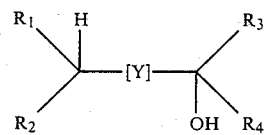

wherein $R_1$ and $R_2$ taken together can represent dimethyl bicyclo [3.1.1] heptyl; $R_3$ represents alkyl; $R_4$ represents alkyl and Y represents a divalent aliphatic group with at least four carbon atoms. Thus, German Offenlegungsschrift No. 2708048 discloses the reaction sequence, starting with pinene and ending up with a tertiary pentenol thusly:

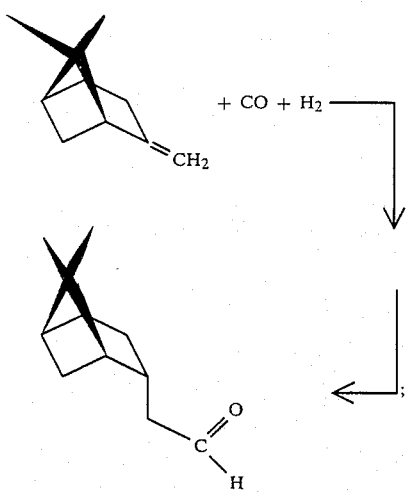

-continued

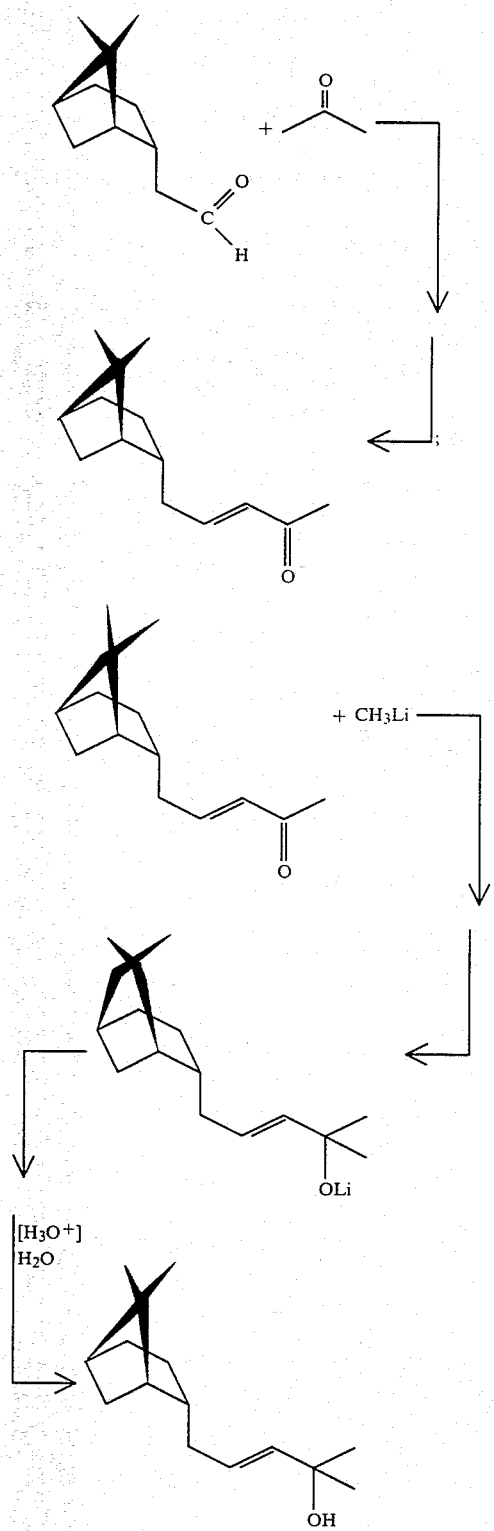

None of the chemicals produced using the process of our invention are tertiary alcohols and the chemicals produced according to the process of our invention are not considered to be similar from a chemical and organoleptic standpoint to the compounds of German Offenlegungsschrift No. 2708048.

German Offenlegungsschrift No. 2708048 is abstracted at Volume 87, 1977, 184084f of Chemical Abstracts.

Himmele and Siegel, Tetrahedron Letters No. 12, pages 907–910, 1976 in the paper entitled "Hydroformylierung Von Alpha-Pinen" discloses the reaction sequence, starting with alpha pinen first going to a carboxaldehyde according to the reaction sequences:

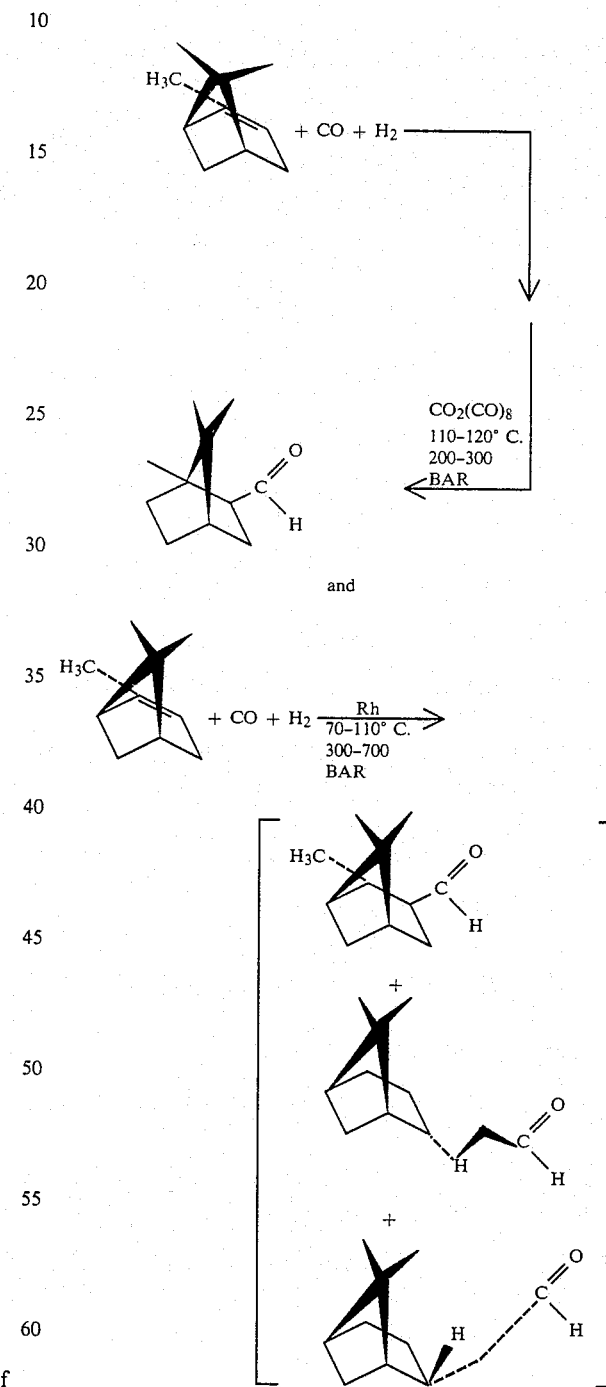

German Offenlegungsschrift No. 2849742 abstracted in Chem. Abstracts 1981, No. 186613a (Hagen and Bruns) published May 22, 1980 discloses the hydroformylation of monocyclic or bicyclic terpenes with at least one double bond in the presence of a rhodium complex containing triphenylphosphine at 70°–160° C. at 100–400 bar to give the corresponding terpenecarboxaldehydes and alleges that these terpenecarboxaldehydes are useful as perfume ingredients. Specifically, Hagen and Bruns state that 3,3-dimethyl-2-norbornane acetaldehyde and 10-formylpinane are prepared from camphene or beta-pinene. Furthermore, U.S. Pat. No. 3,716,498 issued on Feb. 13, 1973 indicates that such compounds as 6,6-dimethyl-bicyclo [3.1.1] hept-2-ene-2-propionaldehyde are capable of augmenting or enhancing the aroma of perfume compositions, for example, in order to give "fresh air qualities" to Foin Coupe colognes blends. Cosmetic Technology, April 1981 at page 18 states that Sandalore ® manufactured by the Givaudan Corporation of Clifton, New Jersey is a useful sandalwood fragrance and has approximately twice the amount of odor intensity of sandalwood oil. Sandalore ® is a mixture of compounds defined according to the structures:

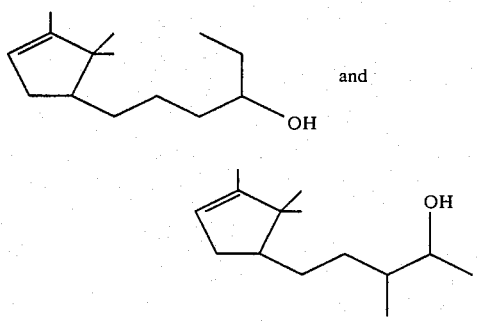

Application for United States Letters Patent No. 299,211 filed on Sept. 3, 1981 describes the compound, 4-methyl-3-cyclohexene-1-carboxylic acid having the structure:

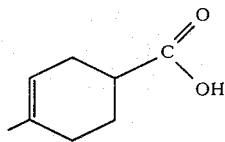

and uses thereof in augmenting or enhancing the aroma of perfume compositions, perfumed articles and colognes, particularly as a replacement for cumin oil and/or cumin aldehyde and the combination of this compound with compounds which yield sweaty, animal, leathery notes defined according to the genera having the structures:

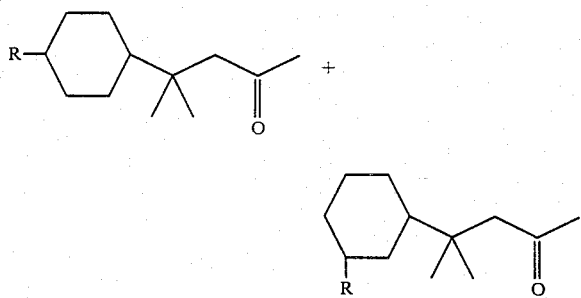

wherein R represents t-butyl or t-amyl as more particularly described in United States Letters Patent No. 3,702,343 issued on Nov. 7, 1972. The use of the mixtures of compounds disclosed in application for U.S. Letters Patent Ser. No. 299,211 filed on Sept. 3, 1981 in combination with the methyl substituted pinyl oxopentenes of our invention is also contemplated within the scope of our invention.

Nothing in the prior art, however, sets forth the products, processes or unique uses of the compositions of matter of our invention. Indeed, the compositions of matter of our invention either as mixtures or products per se, have unexpected, unobvious and advantageous properties over remotely similar compounds set forth in the prior art, for example, the compounds of the German Offenlegungsschrift No. 2708048.

United Kingdom Specification No. 1,471,856 published on Apr. 27, 1977 discloses the reaction sequence:

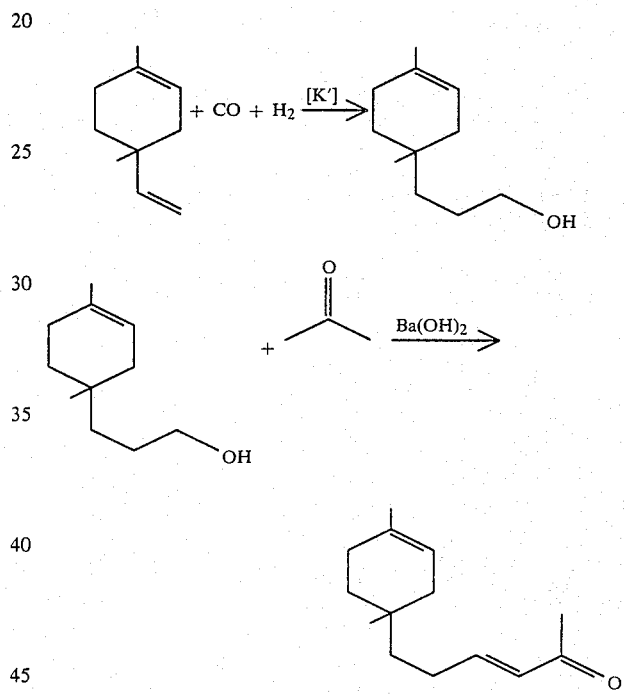

wherein K' represents the catalyst having the structure:

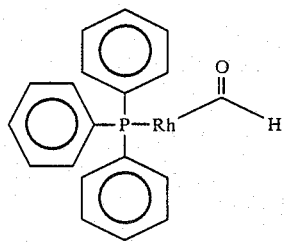

The products produced according to U.K. Specification No. 1,471,856 are structurally dissimilar from the products of the instant invention.

BRIEF DESCRIPTION OF THE DRAWINGS

FIG. A is the GLC profile for the alpha pinene reactant for Example I having the structure:

Figure 5:
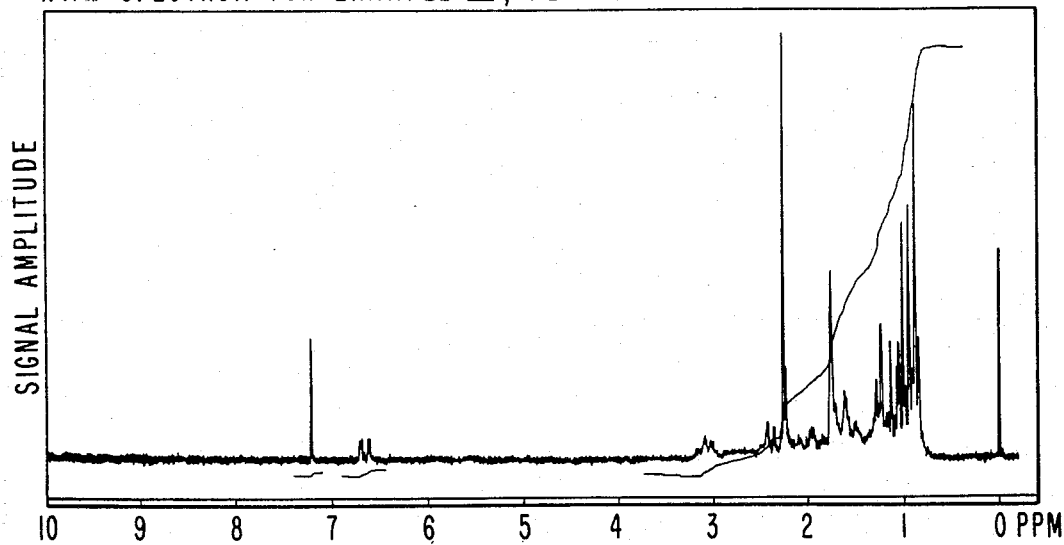

(conditions: 10'×⅛"5% Carbowax 20M programmed at 100°–220° C. at 2° C. per minute).

FIG. AA is the GLC profile for the reaction product of Example I containing a mixture of aldehyde compounds defined according to the structure:

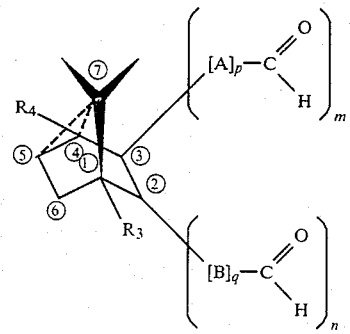

together with the aldehyde having the structure:

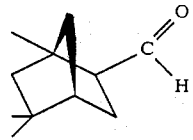

wherein in the mixture, one of the dashed lines at the 7-5 or 7-4 positions represents a carbon-carbon single bond and the other of the dashed lines at the 7-5 or 7-4 position represents no bond; wherein one of $R_3$ or $R_4$ represents hydrogen and the other or $R_3$ or $R_4$ represents hydrogen or methyl; wherein m=0 or 1 and n=0 or 1 with the sum of m+n being equal to 1; wherein A and B each represents methylene defined according to the structure:

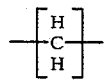

wherein p=0 or 1 and q=0 or 1 with the provisos that:
(i) when the dashed line at the 7-5 position is a carbon-carbon single bond, then $R_3$ and $R_4$ are both hydrogen, m is 0, n is 1 and q is 1;
(ii) when one of $R_3$ or $R_4$ is methyl and the other of $R_3$ or $R_4$ is hydrogen, then p and q are both 0;
(iii) when $R_3$ is methyl, then $R_4$ is hydrogen and the dashed line at the 7-5 position or the dashed line at the 7-4 position is a carbon-carbon single bond; and m is 0; n is 1 and q is 0;
(iv) when $R_4$ is methyl and $R_3$ is hydrogen, then n is 0 and m is 1 and p is 0 and one of the dashed lines at the 7-5 position or the 7-4 position is a carbon-carbon single bond.

FIG. 1 is the GLC profile for the reaction product of Example II (conditions: 10'×⅛" 5% Carbowax column programmed at 100°–220° C. at 4° C. per minute) containing a mixture of compounds defined according to the structure:

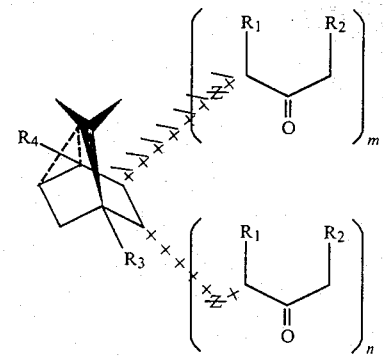

together with the mixture of compounds defined according to the structure:

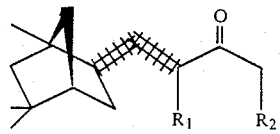

wherein one of the lines:

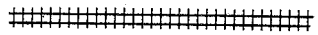

represents a carbon-carbon double bond and the other of the lines:

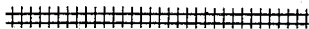

represents a carbon-carbon single bond; wherein Z represents methylidene defined according to the structure:

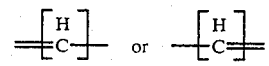

ethylidene defined according to the structure:

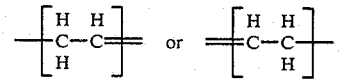

or ethylenyl defined according to the structure

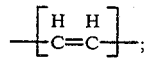

wherein one of the dashed lines represents a carbon-carbon single bond and the other of the dashed lines represents no bond; wherein n is 0 or 1 and m is 0 or 1 with the sum of n×m being equal to 1; wherein $R_1$, $R_2$, $R_3$ and $R_4$ represent hydrogen or methyl; wherein one of the lines:

+ + + + represents a carbon-carbon single bond and the other of the lines:

$$+\!+\!+\!+$$

represents a carbon-carbon single bond or a carbon-carbon double bond; wherein one of the lines:

$$/\!+\!/\!+\!/\!+\!/\!+\!/$$

represents a carbon-carbon single bond and the other of the lines:

$$/\!+\!/\!+\!/\!+\!/\!+\!/$$

represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

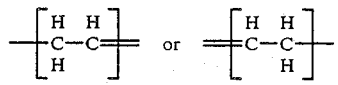

or ethylenyl having the structure:

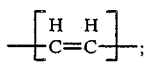

(ii) when one of $R_3$ or $R_4$ is methyl, then either the dashed line at the 7-5 position or the dashed line at the 7-4 position is a carbon-carbon single bond; and Z represents methylidene defined according to the structure:

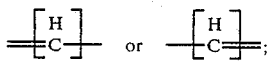

(iii) when $R_3$ is methyl, then n is 1 and m is 0 and $R_4$ is hydrogen; and
(iv) when $R_4$ is methyl, then $R_3$ is hydrogen, n is 0 and m is 1.

FIG. 2 is the mass spectrum for the peak indicated by reference numeral "1" of the GLC profile of FIG. 1 containing the compound having the structure:

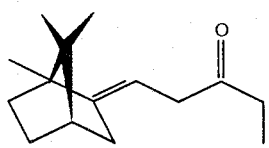

produced according to Example II.

FIG. 3 is the mass spectrum for the peak indicated by reference numeral "3" of the GLC profile of FIG. 1 containing the compound having the structure:

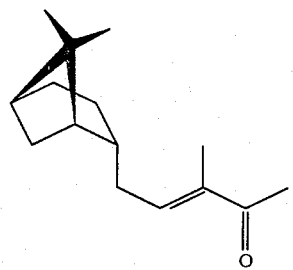

FIG. 4 is the NMR spectrum for the peak indicated by reference numeral "1" of the GLC profile of FIG. 1 containing a component of the reaction product of Example II having the structure:

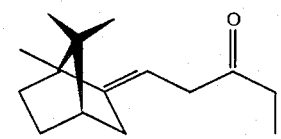

FIG. 5 is the NMR spectrum for the peak indicated by reference numeral "3" of the GLC profile of FIG. 1 containing a component of the reaction product of Example II having the structure:

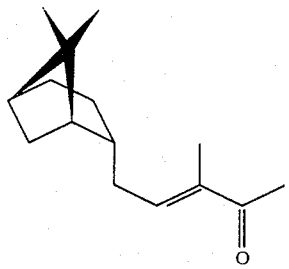

Figure 6:
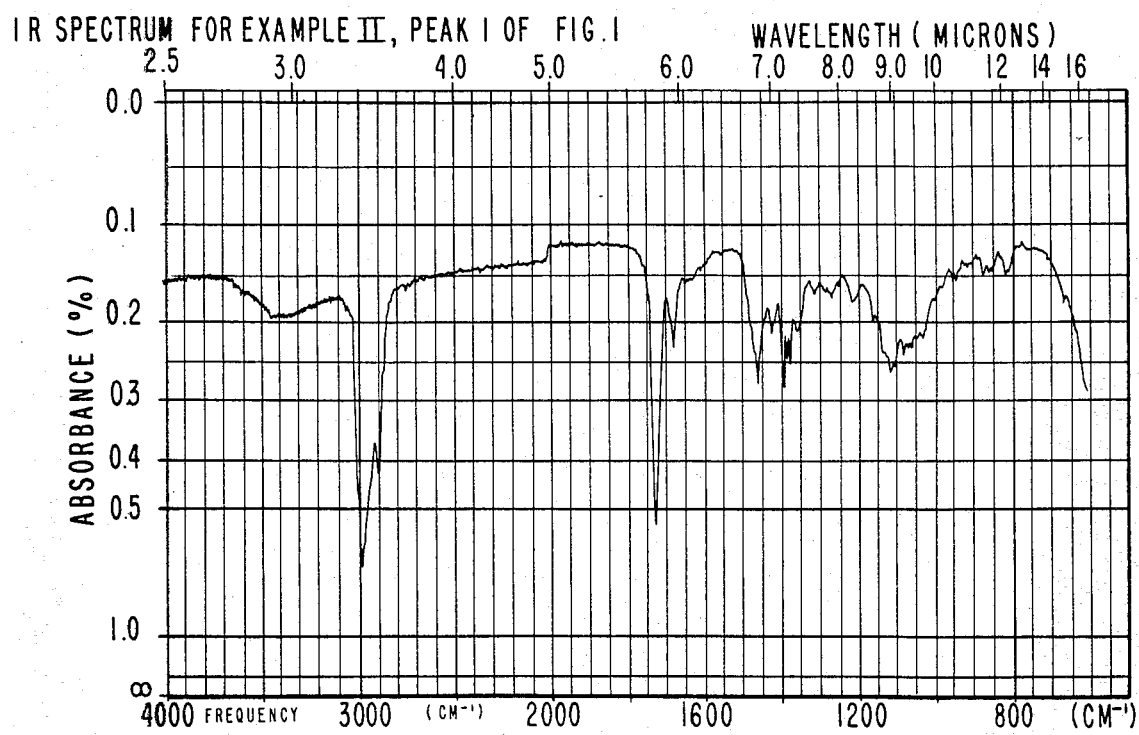

FIG. 6 is the infra-red spectrum for the peak indicated by reference numeral "1" on the GLC profile of FIG. 1 which contains a component of the reaction product of Example II having the structure:

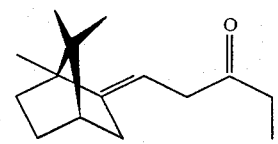

Figure 7:
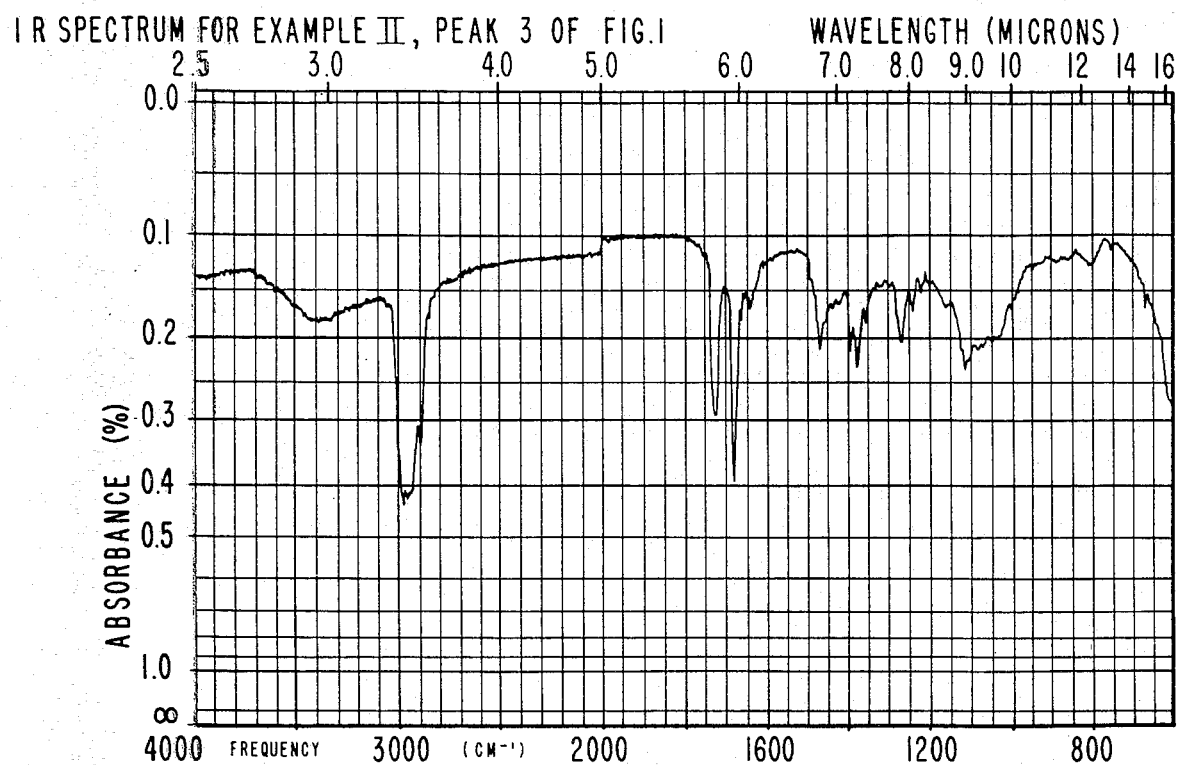

FIG. 7 is the infra-red spectrum for the peak indicated by reference numeral "3" of the GLC profile of FIG. 1 containing a component of the reaction product of Example II having the structure:

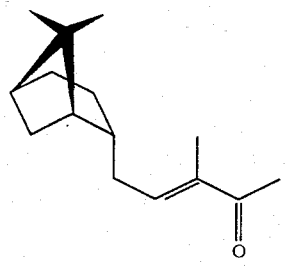

FIG. 8 is the GLC profile for the reaction product of Example IV containing a mixture of ketones defined according to the generic structure:

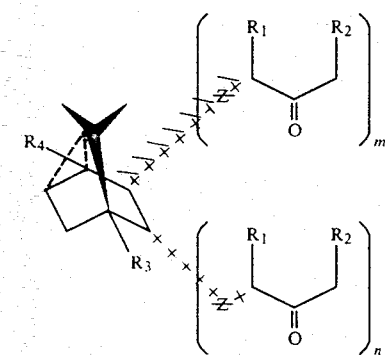

taken together with the mixture of ketones defined according to the structure:

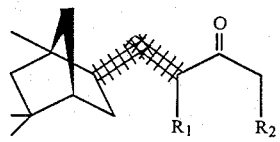

wherein in the mixture, Z represents methylidene defined according to the structure:

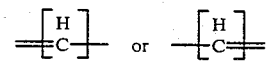

ethylidene defined according to the structure:

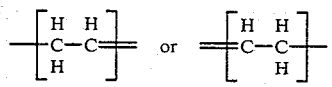

or ethylenyl defined according to the structure:

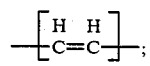

wherein one of the dashed line represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

+ + + + represents a carbon-carbon single bond and other of the lines:

+ + + + represents a carbon-carbon single bond or a carbon-carbon double bond; wherein one of the lines:

/+/+/+/+/+/ represents a carbon-carbon single bond and the other of the lines:

/+/+/+/+/+/ represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure;

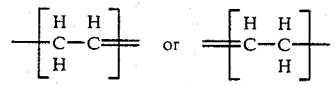

or ethylenyl having the structure:

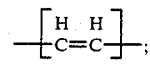

(ii) when one of $R_3$ or $R_4$ is methyl, then either the dashed line at the 7-5 position or the dashed line at the 7-4 position is a carbon-carbon single bond; and Z represents methylidene defined according to the structure:

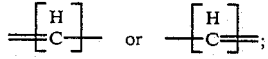

(iii) when $R_3$ is methyl, then n is 1 and m is 0 and $R_4$ is hydrogen; and
(iv) when $R_4$ is methyl, then $R_3$ is hydrogen, n is 0 and m is 1
and wherein one of the lines:

is a carbon-carbon double bond and the other of the lines:

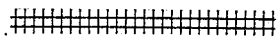

is a carbon-carbon single bond.

Figure 9:
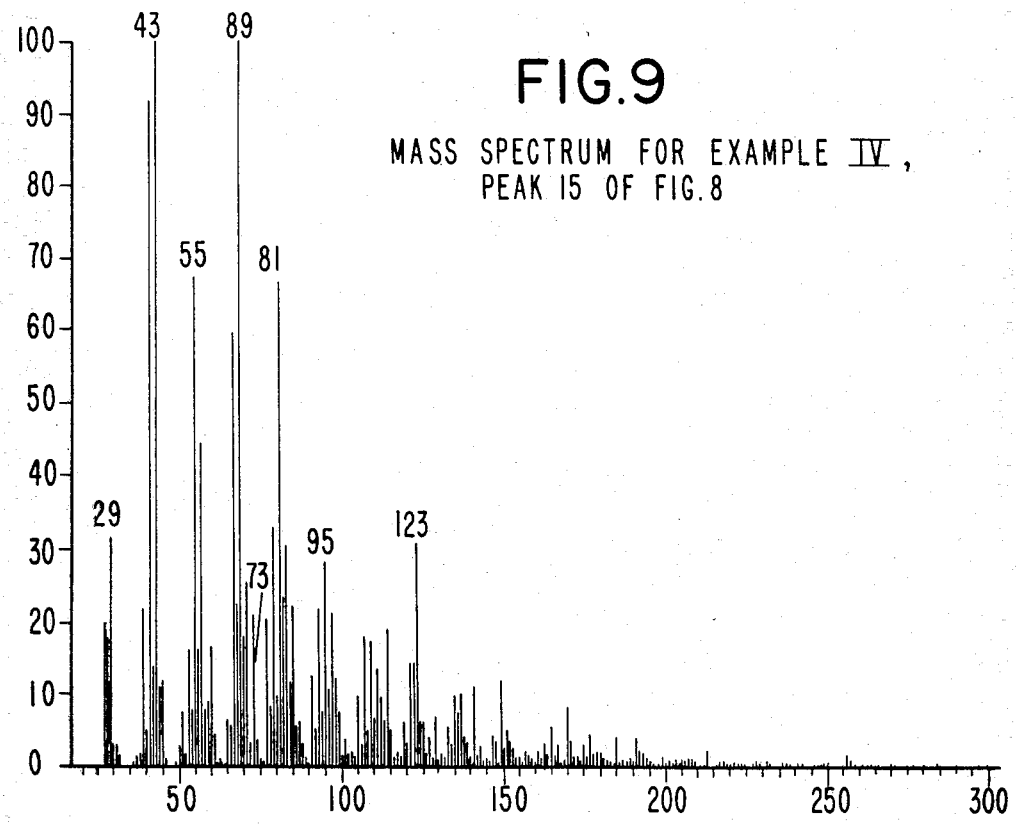

FIG. 9 is the mass spectrum for the peak indicated by reference numeral "15" of the GLC profile of FIG. 8 containing a component of the reaction product of Example IV having the structure:

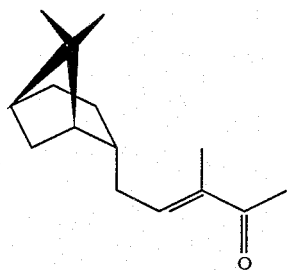

FIG. 10 is the NMR spectrum for the peak indicated by reference numeral "15" of the GLC profile of FIG. 8 containing a component of the reaction product of Example IV having the structure:

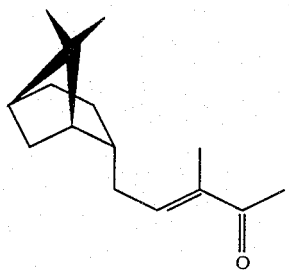

FIG. 11 is the GLC profile of the crude reaction product of Example V (crude "A") prior to "work-up" containing a mixture of compounds defined according to the structure:

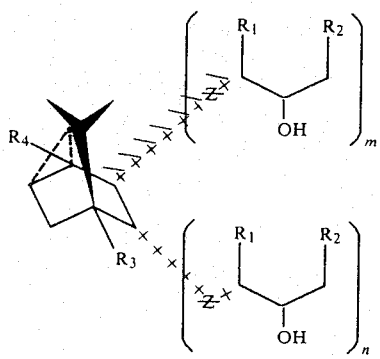

taken together with the mixture of compounds defined according to the structure:

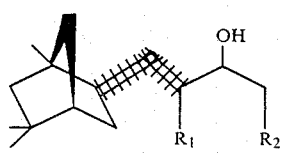

wherein the mixture Z represents methylidene defined according to the structure:

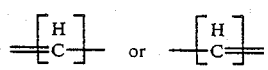

ethylidene defined according to the structure:

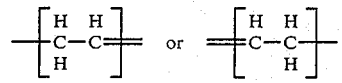

or ethylenyl defined according to the structure:

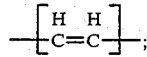

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

+ + + + represents a carbon-carbon single bond and the other of the lines:

+ + + + represents a carbon-carbon single bond or a carbon-carbon double bond; wherein one of the lines:

/+/+/+/+/+/ represents a carbon-carbon single bond and the other of the lines:

/+/+/+/+/+/ represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

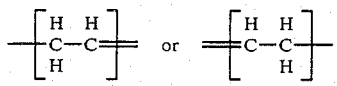

or ethylenyl having the structure:

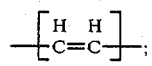

(ii) when one of $R_3$ or $R_4$ is methyl, then either the dashed line at the 7-5 position or the dashed line at the 7-4 position is a carbon-carbon single bond; and Z represents methylidene defined according to the structure:

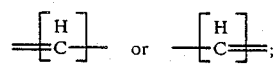

(iii) when $R_3$ is methyl, then n is 1 and m is 0 and $R_4$ is hydrogen; and
(iv) when $R_4$ is methyl, then $R_3$ is hydrogen, n is 0 and m is 1 and wherein one of the lines:

is a carbon-carbon double bond and the other of the lines:

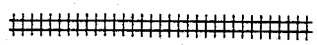
is a carbon-carbon single bond.

FIG. 12 is the GLC profile for the crude reaction product of Example V (after work-up) containing the mixture of compounds defined according to the structure:

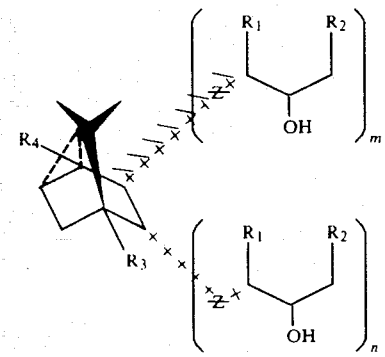

Figure 13:
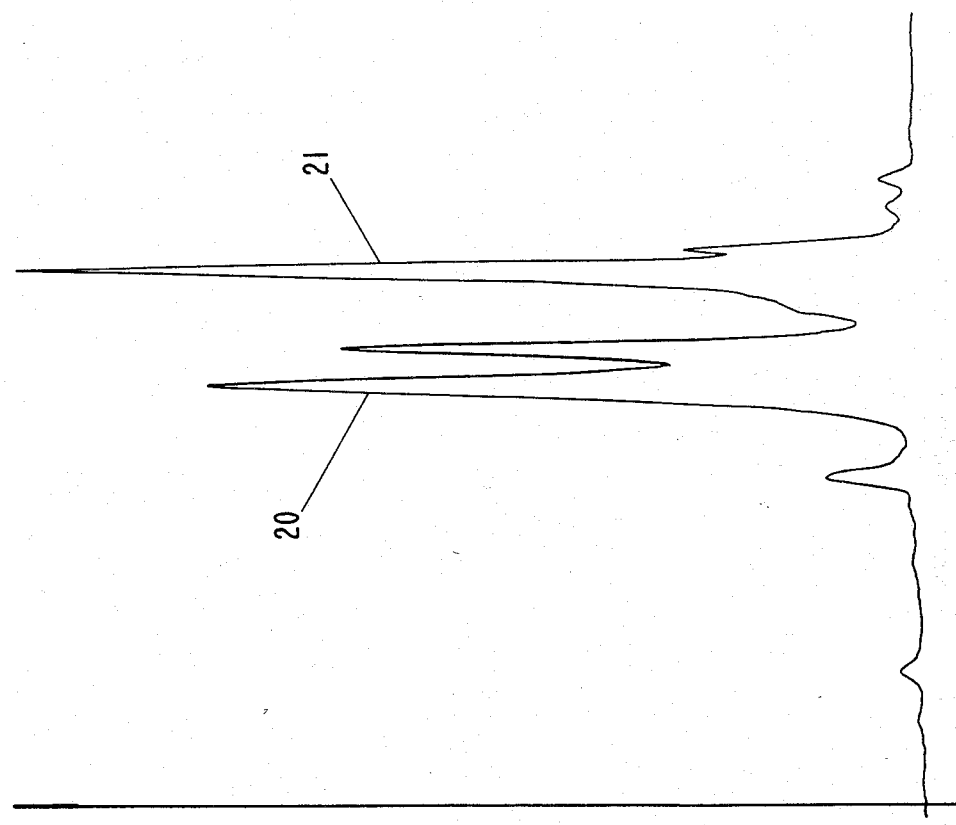

FIG. 13 is the GLC profile for fraction 17 of the distillation product of Example V containing a mixture of compounds defined according to the structure:

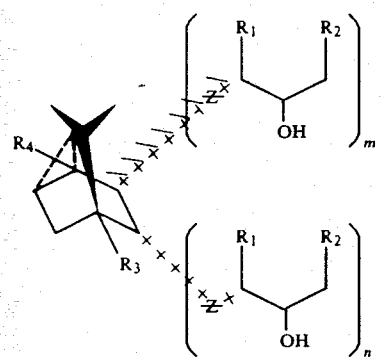

taken together with the mixture of compounds defined according to the structure:

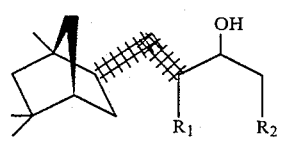

Figure 14:
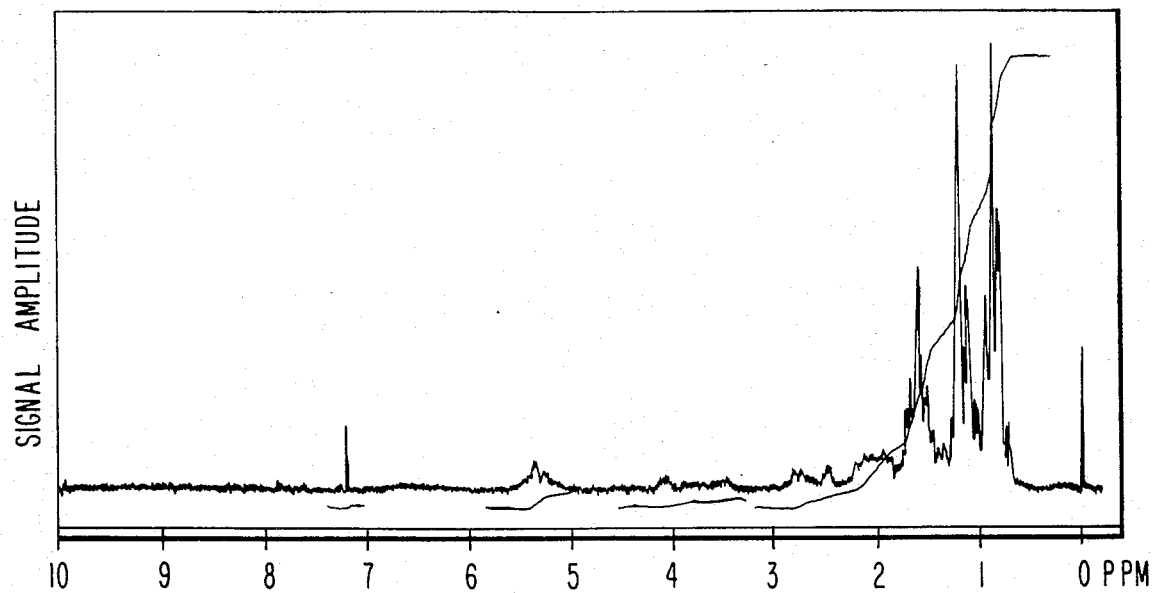

FIG. 14 is the NMR spectrum for the peak indicated by the reference numeral "20" of the GLC profile of FIG. 13 containing a component of fraction 17 of the distillation product of the reaction product of Example V containing a mixture of compounds defined according to the structures:

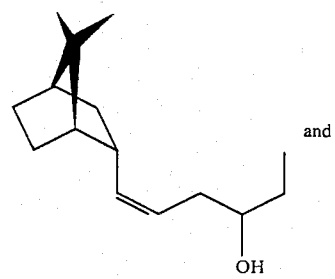

and

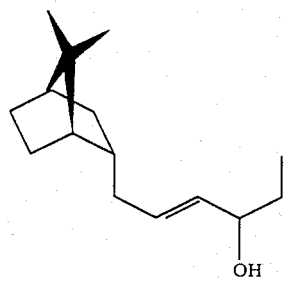

Figure 15:
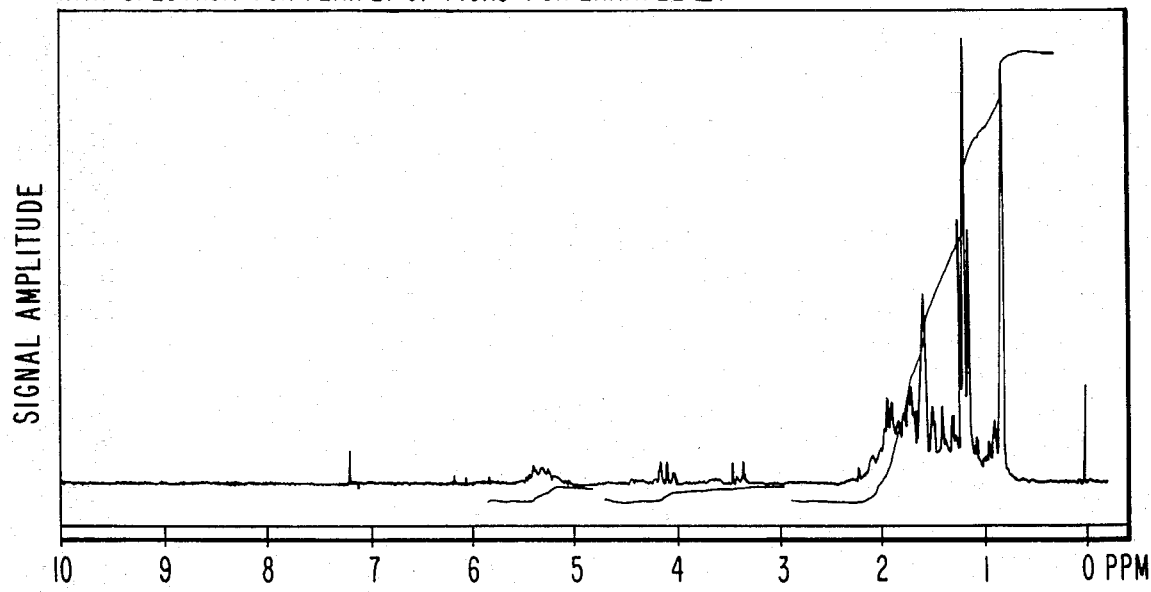

FIG. 15 is the NMR spectrum for the peak indicated by the reference numeral "21" of the GLC profile of FIG. 13 containing a component of fraction 17 of the distillation product of the reaction product of Example V defined according to the structure:

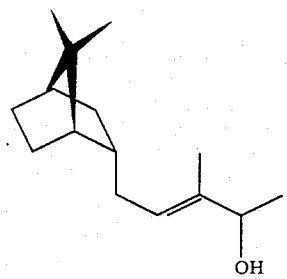

Figure 16:
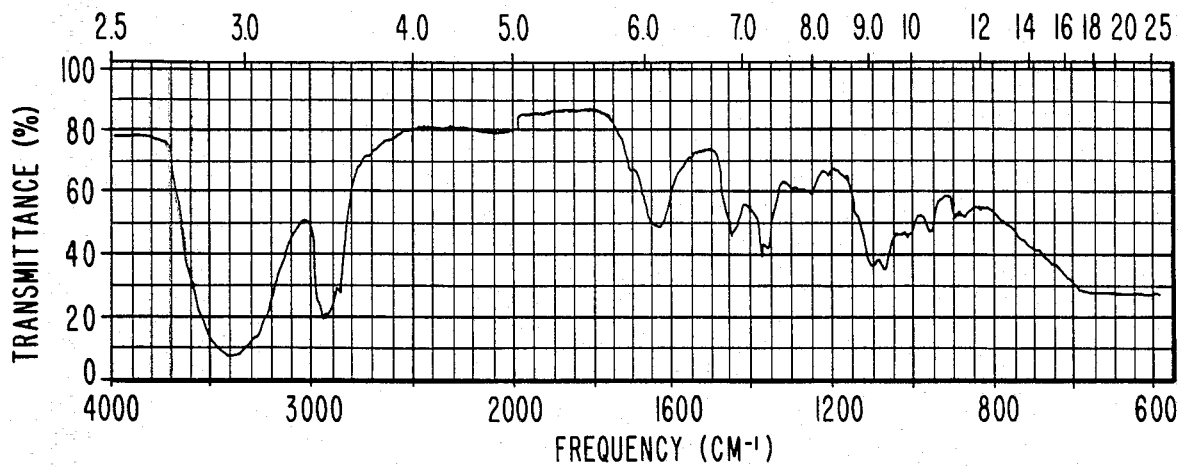

FIG. 16 is the infra-red spectrum for the crude reaction product of Example V (after work-up; crude reaction product "B") containing a mixture of compounds defined according to the structure:

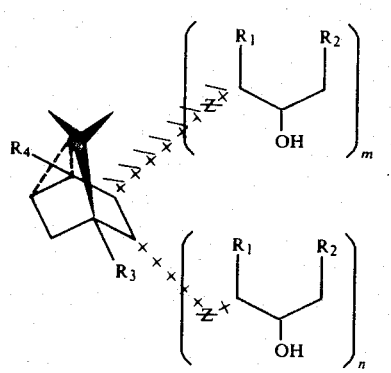

taken together with the mixture of compounds defined according to the structure:

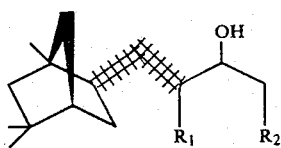

Figure 17:
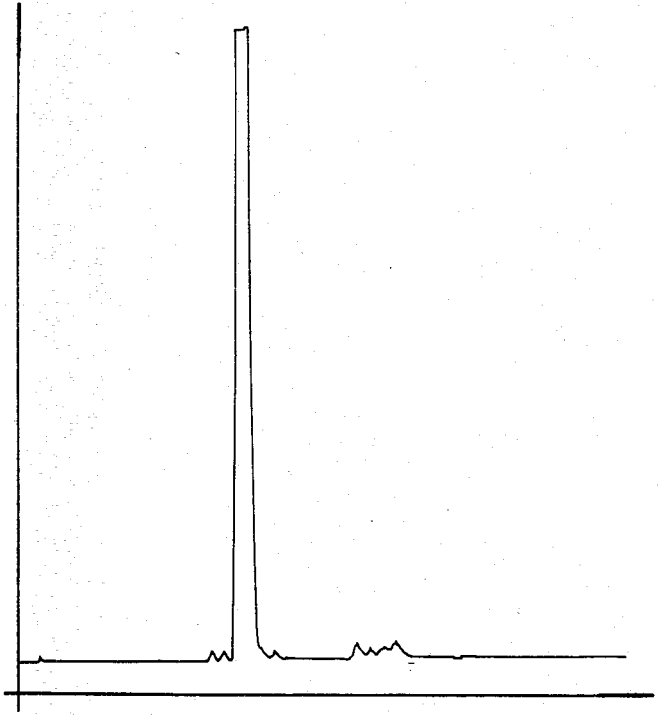

FIG. 17 is the GLC profile for the beta pinene use as a reactant in Example V(A), having the structure:

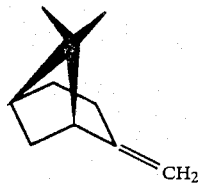

Figure 18:
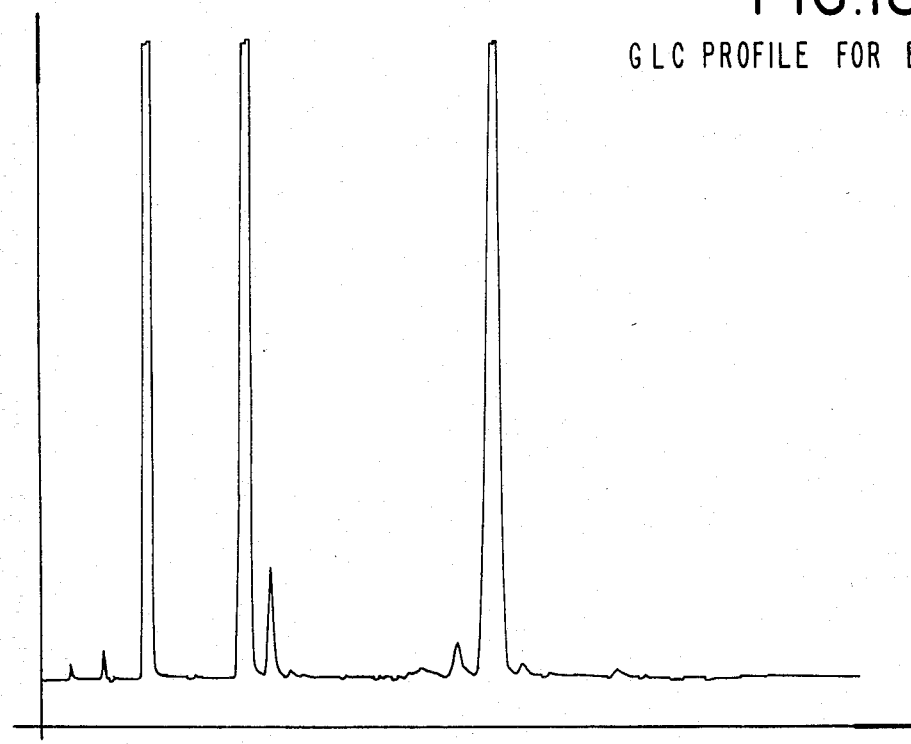

FIG. 18 is the GLC profile for the reaction product of Example V(A) containing the compound defined according to the structure:

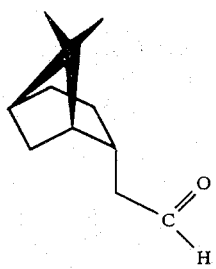

Figure 19:
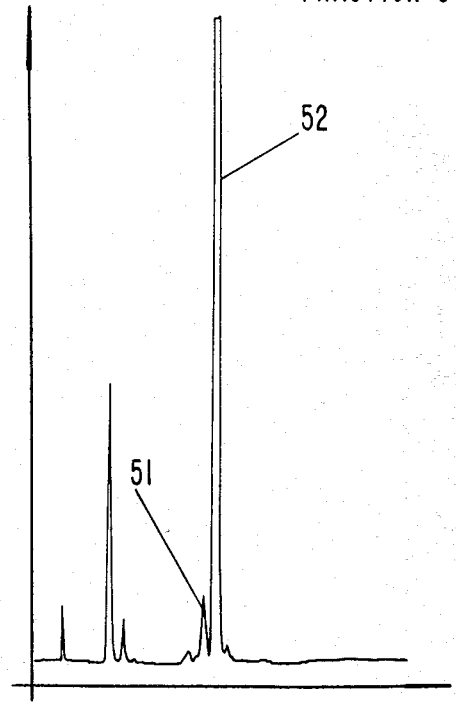

FIG. 19 is the GLC profile for fraction 3 of the distillation product of the reaction product of Example V(A) (conditions: 10'×⅛' 5% Carbowax column programmed at 100°–220° C. at 4° C. per minute) containing the compounds having the structures:

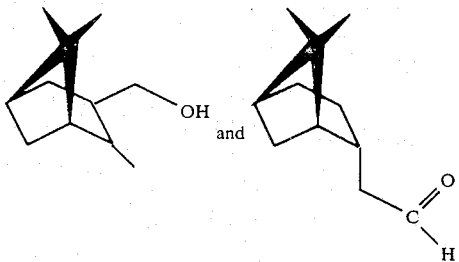

Figure 20:
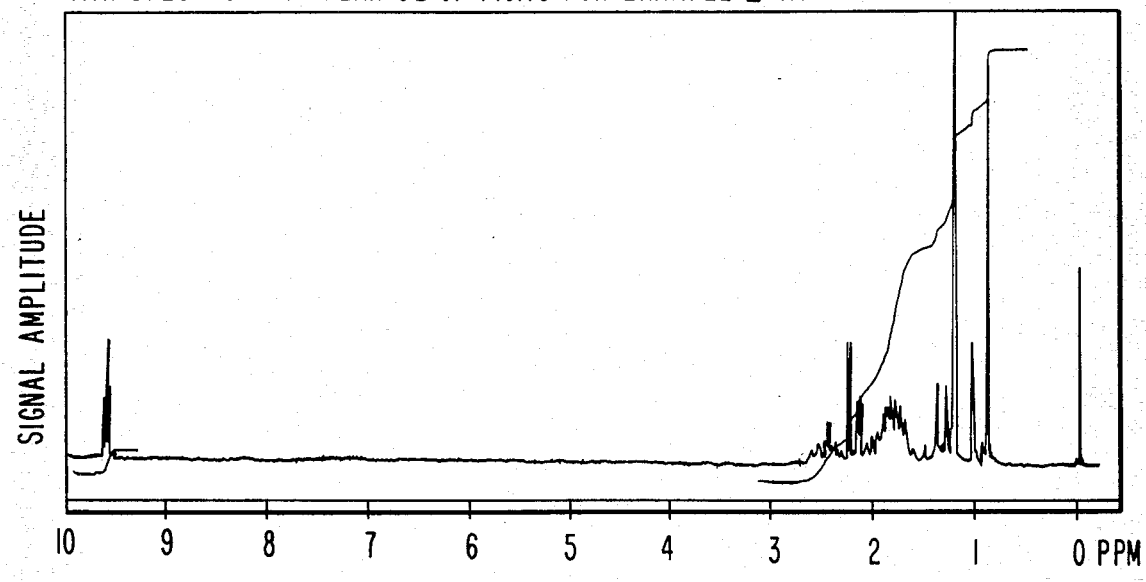

FIG. 20 is the NMR spectrum for the peak indicated by reference numeral "52" of FIG. 19 for the compound defined according to the structure:

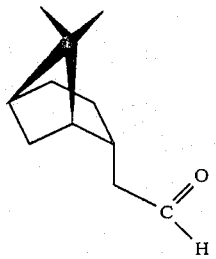

Figure 21:
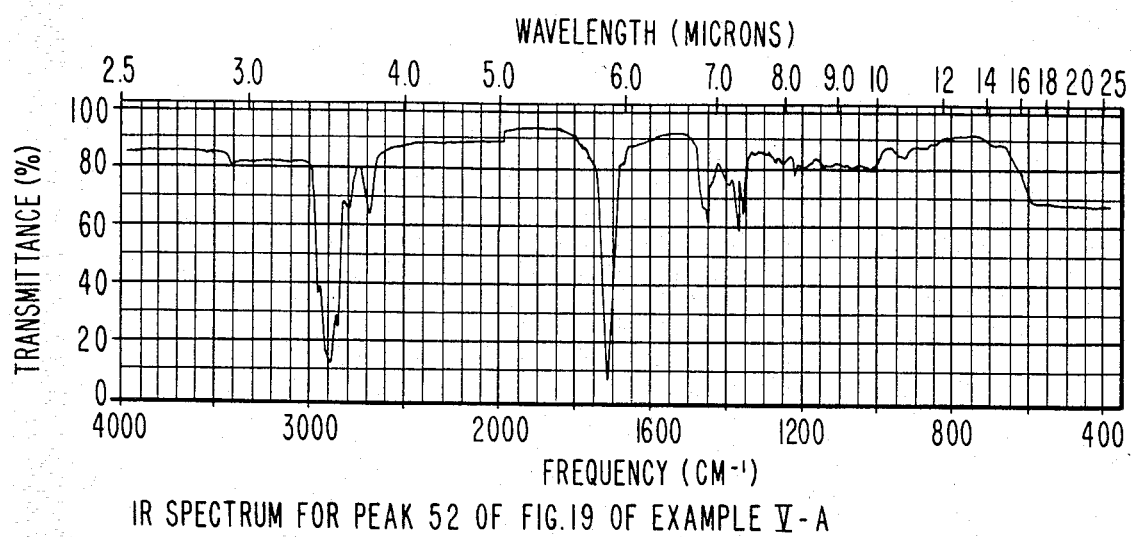

FIG. 21 is the infra-red spectrum for the compound of peak 52 of FIG. 19 for Example V(A) for the compound having the structure:

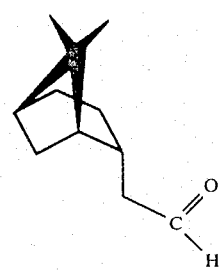

Figure 22:
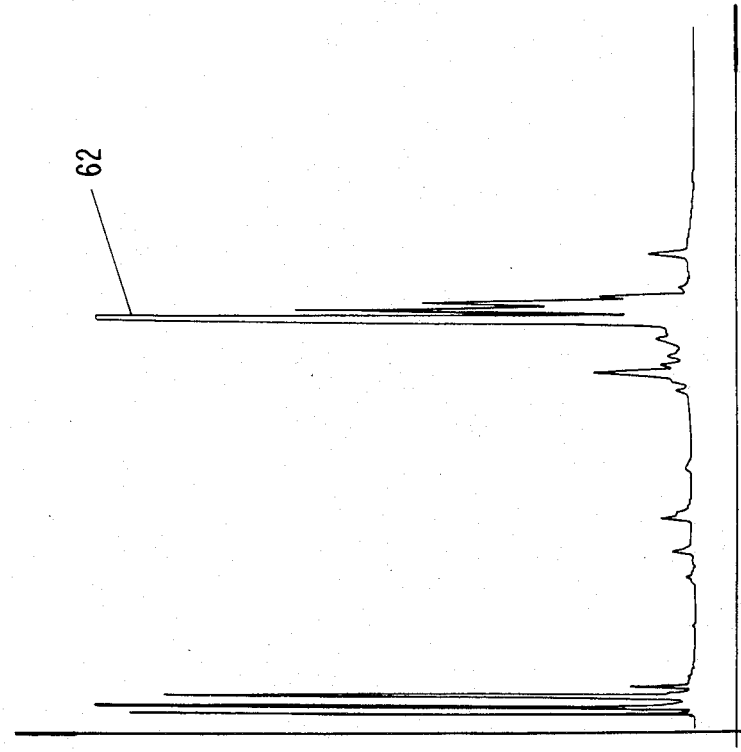

FIG. 22 is the GLC profile for fraction 6 of the reaction product of Example V(B) (conditions: 10'×⅛" 5% Carbowax column programmed at 100°–220° C. at 4° C. per minute) containing the compound having the structure:

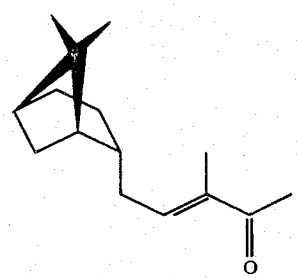

Figure 23:
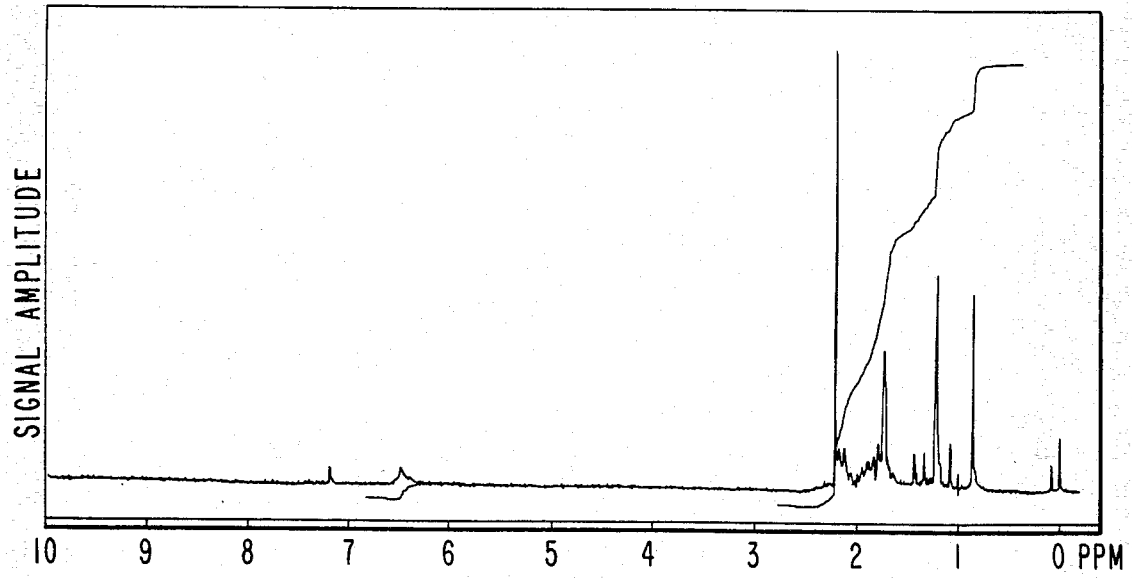

FIG. 23 is the NMR spectrum for the peak indicated by reference numeral "62" of FIG. 22 for Example V(B) containing the compound defined according to the structure:

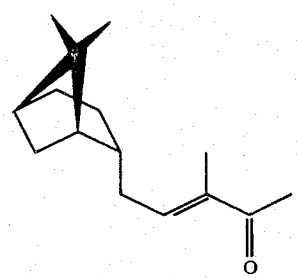

FIG. 24 is the infra-red spectrum for the peak indicated by reference numeral "62" of FIG. 22 for Example V(B) for the compound defined according to the structure:

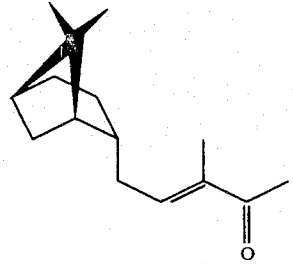

DETAILED DESCRIPTION OF THE DRAWINGS

FIG. A is the GLC profile for the alpha pinene reactant used in Example I (conditions: 10'×⅛" 5% Carbowax 20M column programmed at 100°–220° C. at 2° C. per minute). The peak indicated by reference numeral "100" is the peak for the alpha pinene which is defined according to the structure:

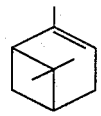

FIG. AA is the GLC profile for the reaction product of Example I resulting from the reaction of alpha pinene with carbon monoxide and hydrogen (conditions: 2'×⅛" Carbowax column programmed at 100°–220° C. at 6° C. per minute). The peak indicated by reference numeral "101" is the peak for the unreacted alpha pinene defined according to the structure:

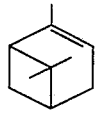

The peaks indicated by reference numeral "102", "103", "104", and "105" are for aldehydes defined according to the structures:

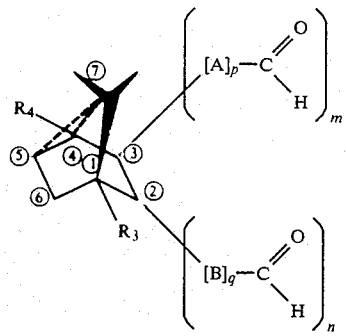

taken together with the compound having the structure:

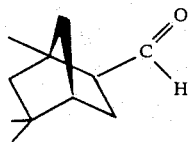

wherein in the mixture one of the dashed lines at the 7–5 or 7–4 positions represents a carbon-carbon single bond and the other of the dashed lines at the 7–5 or 7–4 position represents no bond; wherein one of $R_3$ or $R_4$ represents hydrogen and the other of $R_3$ or $R_4$ represents hydrogen or methyl; wherein m=0 or 1 and n=0 or 1 with the sum of m+n being equal to 1; wherein A and B each represents methylene defined according to the structure:

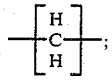

wherein p=0 or 1 and q=0 or 1 with the provisos that:

(i) when the dashed line at the 7–5 position is a carbon-carbon single bond, then $R_3$ and $R_4$ are both hydrogen, m is 0, n is 1 and q is 1;

(ii) when one of $R_3$ or $R_4$ is methyl and the other of $R_3$ or $R_4$ is hydrogen, then p and q are both 0;

(iii) when $R_3$ is methyl, then $R_4$ is hydrogen and the dashed line at the 7–5 position or the dashed line at the 7–4 position is a carbon-carbon single bond; and m is 0; n is 1 and q is 0;

(iv) when $R_4$ is methyl and $R_3$ is hydrogen, then n is 0 and m is 1 and p is 0 and one of the dashed lines at the 7–5 position or the 7–4 position is a carbon-carbon single bond.

FIG. 1 is the GLC profile for the crude reaction product of Example II (conditions: 10'×⅛" 5% Carbowax column programmed at 100°–220° C. at 4° C. per minute). The peaks indicated by reference numerals "4", "5" and "6" are the peaks for the mixture of aldehydes defined according to the structure:

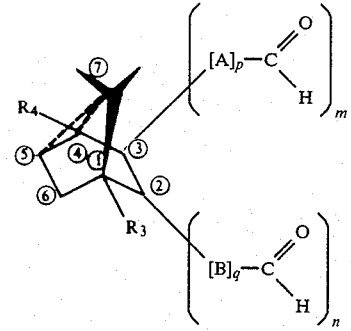

taken together with the compound having the structure:

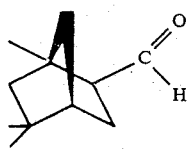

The peaks indicated by reference numerals "1", "2" and "3" are for the ketone reaction product defined according to the structure:

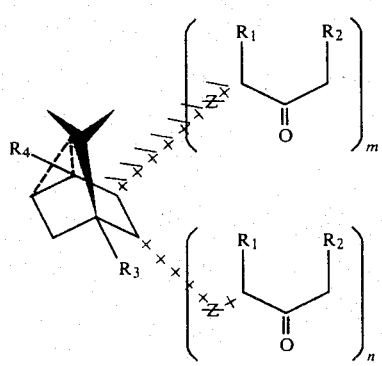

taken together with the mixture of compounds defined according to the structure:

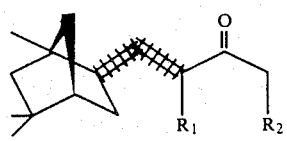

wherein in the mixture, Z represents methylidene defined according to the structure:

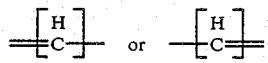

ethylidene defined according to the structure:

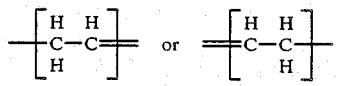

or ethylenyl defined acccording to the structure:

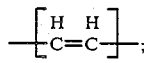

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represents hydrogen or methyl; wherein one of the lines;

+ + + + represents a carbon-carbon single bond and the other of the lines:

+ + + + represents a carbon-carbon single bond or a carbon-carbon double bond; wherein one of the lines:

/+/+/+/+/ represents a carbon-carbon single bond and the other of the lines:

/+/+/+/+/ represents a carbon-carbon single bond or a carbon-carbon double bond; with the provisos that:

(i) when $R_3$ and $R_4$ are each hydrogen, the dashed line at the 7-5 position is a carbon-carbon single bond; n=0 and m is 1; Z represents ethylidene having the structure:

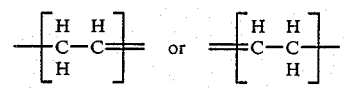

or ethylenyl having the structure:

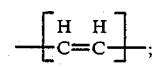

(ii) when one of $R_3$ or $R_4$ is methyl, then either the dashed line at the 7-5 position or the dashed line at the 7-4 position is a carbon-carbon single bond; and Z represents methylidene defined according to the structure:

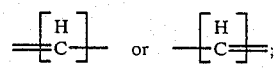

(iii) when $R_3$ is methyl, then n is 1 and m is 0 and $R_4$ is hydrogen; and
(iv) when $R_4$ is methyl, then $R_3$ is hydrogen, n is 0 and m is 1 wherein one of the lines:

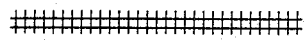

is a carbon-carbon double bond and the other of the lines:

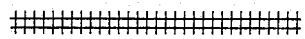

is a carbon-carbon single bond.

FIG. 8 is the GLC profile for the reaction product of Example IV (conditions: 10′×⅛″ 5% Carbowax column programmed at 100°–220° C. at 4° C. per minute). The peaks indicated by reference numerals "11", "12", "13", "14" and "15" are for the ketone reaction product defined according to the structure:

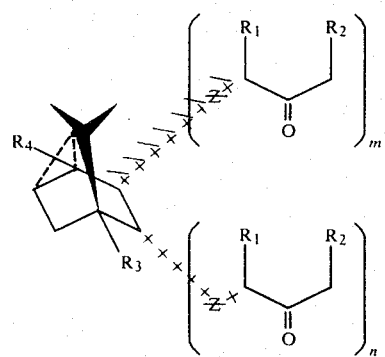

taken together with the mixture of compounds defined according to the structure:

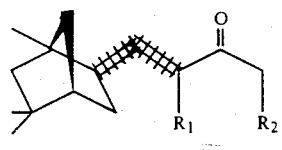

FIG. 13 is the GLC profile for fraction 17 of the distillation product of the reaction product of Example V (conditions: 3′33⅛″ 5% Carbowax column programmed at 70°–230° C. at 2° C. per minute). The peak indicated by reference numeral "20" is for the mixture of compounds defined according to the structures:

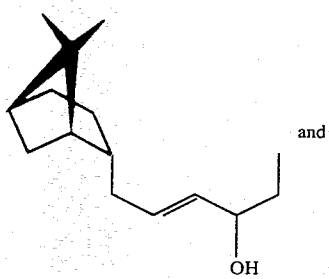

and

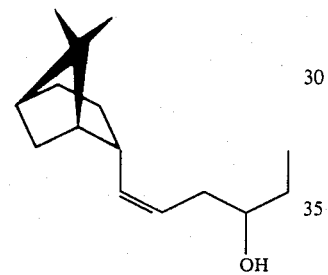

The peak indicated by reference numeral "21" is for the compound defined according to the structure:

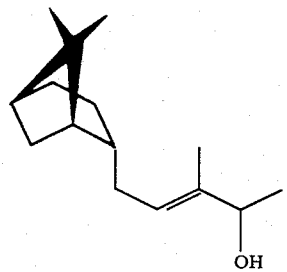

FIG. 19 is the GLC profile for distillation fraction 3 of the reaction product of Example V(A). The conditions are: 10′×⅛″ 5% Carbowax column programmed at 100°–220° C. at 4° C. per minute. The peak indicated by reference numeral "51" is the peak for the compound having the structure:

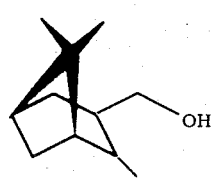

The peak indicated by reference numeral "52" is for the compound having the structure:

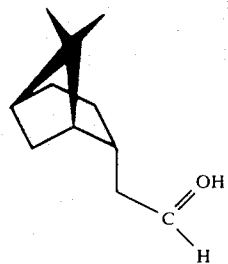

FIG. 22 is the GLC profile for fraction 6 of the distillation product of the reaction product of Example V(B). The conditions for this GLC profile are: 10′×⅛″ 5% Carbowax column programmed at 100°–220° C. at 4° C. per minute. The peak indicated by reference numeral "62" is the peak for the compound defined according to the structure:

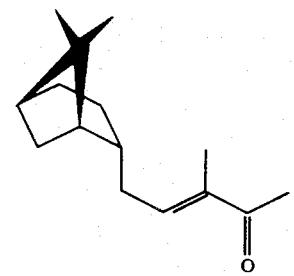

THE INVENTION

The present invention provides the compounds defined according to the generic structure:

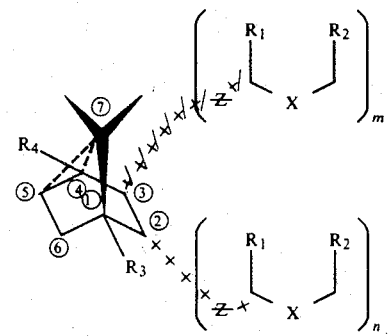

as well as compounds defined according to the structure:

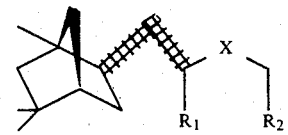

wherein Z represents methylidene defined according to the structure:

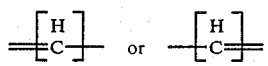

ethylidene defined according to the structure:

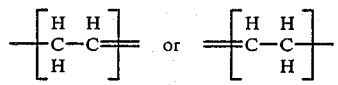

or ethylenyl defined according to the structure:

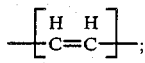

wherein one of the dashed lines represents a carbon-carbon single bond and the other of the dashed lines represents no bond; wherein n is 0 or 1 and m is 0 or 1 with the sum of n+m being equal to 1; wherein X represents carbinol having the structure:

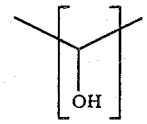

or ketone having the structure:

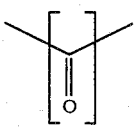

wherein $R_1$, $R_2$, $R_3$ and $R_4$ represent hydrogen or methyl; wherein one of the lines:

+ + + + represents a carbon-carbon single bond and the other of the lines:

+ + + + represents a carbon-carbon single bond or a carbon-carbon double bond; wherein one of the lines:

/+/+/+/+/ represents a carbon-carbon single bond and the other of the lines:

/+/+/+/+/ represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

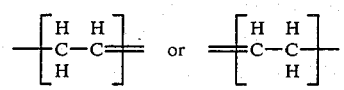

or ethylenyl having the structure:

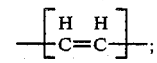

(ii) when one of $R_3$ or $R_4$ is methyl, then either the dashed line at the 7-5 position or the dashed line at the 7-4 position is a carbon-carbon single bond; and Z represents methylidene defined according to the structure:

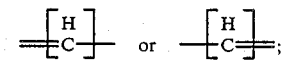

(iii) when $R_3$ is methyl, then n is 1 and m is 0 and $R_4$ is hydrogen; and
(iv) when $R_4$ is methyl, then $R_3$ is hydrogen, n is 0 and m is 1 wherein one of the lines:

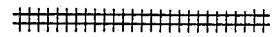

is a carbon-carbon double bond and the other of the lines:

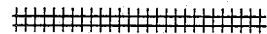

is a carbon-carbon single bond.

The present invention also provides an economical, efficient process for synthesizing the compounds having the generic structure:

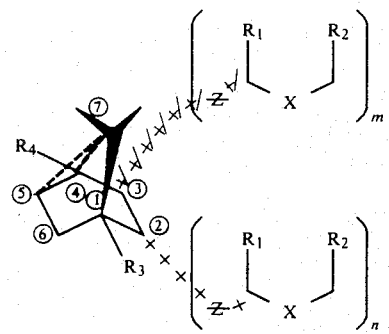

as well as compounds defined according to the structure:

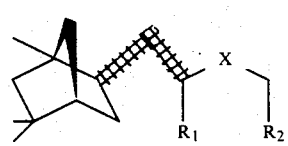

by reacting alpha pinene defined according to the structure:

or beta pinene having the structure:

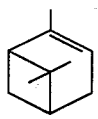

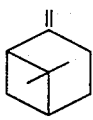

or a mixture of alpha pinene and beta pinene defined according to the structure:

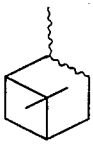

wherein one of the wavy lines:

is a carbon-carbon double bond and the other of the wavy lines is a carbon-carbon single bond with a mixture of carbon monoxide and hydrogen to produce a mixture of aldehydes defined according to the structure:

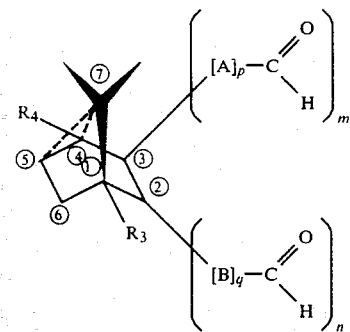

taken together with the compound having the structure:

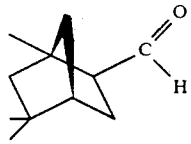

wherein in the mixture one of the dashed lines at the 7-5 or 7-4 positions represents a carbon-carbon single bond and the other of the dashed lines at the 7-5 or 7-4 position represents no bond; wherein one of $R_3$ or $R_4$ represents hydrogen and the other of $R_3$ or $R_4$ represents hydrogen or methyl; wherein m=0 or 1 and n=0 or 1 with the sum of m+n being equal to 1; wherein A and B each represents methylene defined according to the structure:

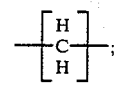

wherein
p=0 or 1 and q=0 or 1 with the provisos that:
(i) when the dashed line at the 7-5 position is a carbon-carbon single bond, then $R_3$ and $R_4$ are both hydrogen, m is 0, n is 1 and q is 1;
(ii) when one of $R_3$ or $R_4$ is methyl and the other of $R_3$ or $R_4$ is hydrogen, then p and q are both 0;
(iii) when $R_3$ is methyl, then $R_4$ is hydrogen and the dashed line at the 7-5 position or the dashed line at the 7-4 position is a carbon-carbon single bond; and m is 0; n is 1 and q is 0;
(iv) when $R_4$ is methyl and $R_3$ is hydrogen, then n is 0 and m is 1 and p is 0 and one of the dashed lines at the 7-5 position or the 7-4 position is a carbon-carbon single bond;

and then reacting the resulting mixture of aldehydes with methyl ethyl ketone or separating the mixture of aldehydes to its individual components and reacting one or more of the individual components with methyl ethyl ketone to produce a ketone or a mixture of ketones defined according to the structure:

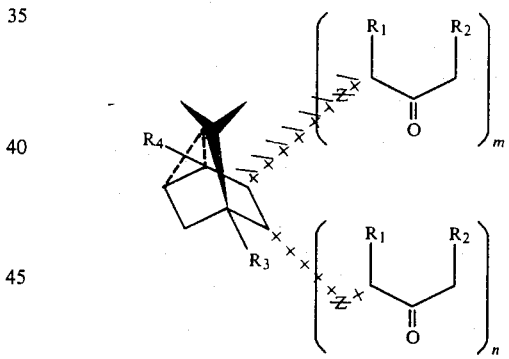

taken together with the compounds defined according to the structure:

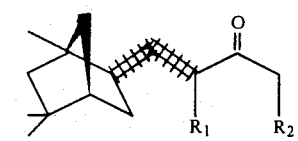

and either using the resulting mixture for its organoleptic properties or using the individual ketones for their respective organoleptic properties or further reacting the mixture or the individual ketones with lithium aluminum hydride or an alkali metal borohydride to form individually or in admixture alcohol(s) defined according to the structure:

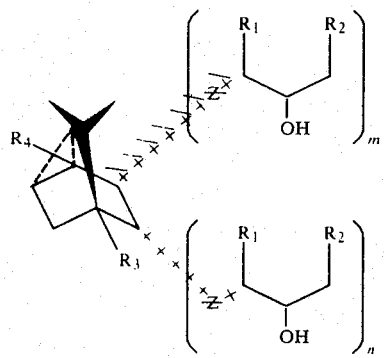

and/or alcohol(s) defined according to the structure:

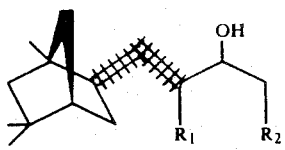

The alcohol mixtures can be used as is for their organoleptic properties or the resulting mixtures can be separated into their individual components and used for their organoleptic properties.

Thus, the present invention also provides processes for using compounds defined according to the generic structure:

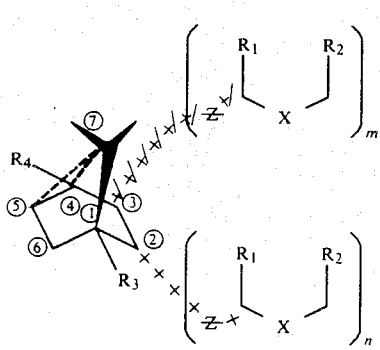

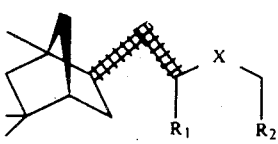

for their organoleptic properties in augmenting or enhancing the organoleptic properties of consumable materials, that is, the aroma or taste of perfumes, colognes, perfumed articles (such as solid or liquid cationic, anionic, nonionic or zwitterionic detergents, soaps, fabric softeners, drier-added fabric softener articles such as BOUNCE ®, a registered trademark of the Procter & Gamble Company of Cincinnati, Ohio, fabric brighteners and cosmetic powders), food flavor compositions, foodstuffs, chewing gums, toothpastes, chewing tobaccos, medicinal products, smoking tobacco articles, smoking tobacco products and flavors for augmenting or enhancing smoking tobacco articles or smoking tobacco compositions.

The methyl substituted pinyl oxopentenes of our invention may be prepared by first reacting alpha pinene or beta pinene or a mixture of alpha pinene and beta pinene with carbon monoxide and hydrogen according to an oxo reaction to produce a mixture of aldehydes according to the reaction:

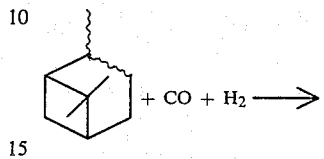

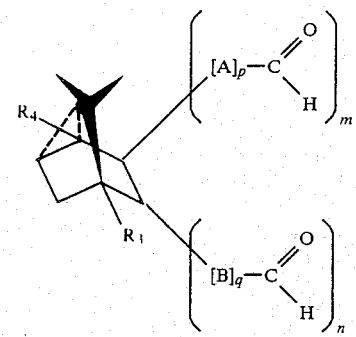

and/or the reaction:

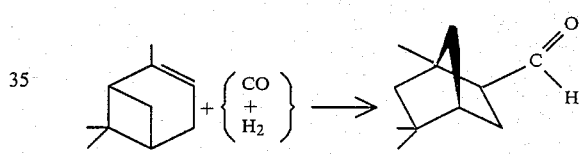

wherein one of the wavy lines:

represents a carbon-carbon double bond and the other of the wavy lines:

represents a carbon-carbon single bond.

This reaction is carried out in the presence of a "oxo reaction catalyst" such as rhodium, $Co_2(CO)_8$, or an organophosphorous polydentate ligand such as those described in European Published Application No. 33,554 published on Aug. 12, 1981, the specification for which is incorporated herein by reference. Examples of which are:

$\phi_2$-P—$(CH_2)_2$—P$\phi_2$, $\phi$-P$+(CH_2)_2$—P$\phi_2]_2$, P$+(CH_2)_2$—P$\phi_2]_3$, $\phi_2$P—HC=CH—P$\phi_2$, and $\phi$-P—CH—$CH_2$—P$\phi_2$
                                              |
                                              $CH_3$ at pressures of from about 3 atmospheres up to about 1,000 atmospheres and at temperatures in the range of from about 30° C. up to about 150° C. Preferably when using a rhodium catalyst, the temperature of reaction is between 70° and 110° C.; when using a $Co_2(CO)_8$ catalyst, the temperature is between 110° and 120° C.; and when using a ligand such as those exemplified in European Published Application No. 33,554, the temperature may vary from 95° C. up to 120° C. as is set forth in the following table:

TABLE A

| Ligand | Reaction Temperature |
|---|---|
| $\phi_2P(CH_2)_2P\phi_2$ | 95–120° C. |
| $\phi P \begin{cases} CH_2-CH_2-P\phi_2 \\ CH_2-CH_2-P\phi_2 \end{cases}$ | 120° C. |
| $P \begin{cases} CH_2-CH_2-P\phi_2 \\ CH_2-CH_2-P\phi_2 \\ CH_2-CH_2-P\phi_2 \end{cases}$ | 120° C. |
| $\phi_2P-CH=CH-P\phi_2$ | 120° C. |
| $\phi_2P-CH(CH_3)-CH_2-P\phi_2$ | 95° C. |
| $\phi_2P(CH_2)_4P\phi_2$ | 95° C. |
| $\phi_2P(CH_2)_3P\phi_2$ | 95° C. |
| $P\phi_3$ | 120° C. |
| $\phi_2P(CH_2)_{10}P\phi_2$ | 120° C. |
| $\phi_2PCH_2P\phi_2$ | 120° C. |
| $(CH_3)_2P(CH_2)_2P(CH_3)_2$ | 120° C. |

The resulting mixture of aldehydes may then be separated for subsequent reaction or may be used as is and is preferably used as is as a mixture (which is the most economical way to proceed). The mixture or individual aldehydes are then reacted with methyl ethyl ketone according to the reactions:

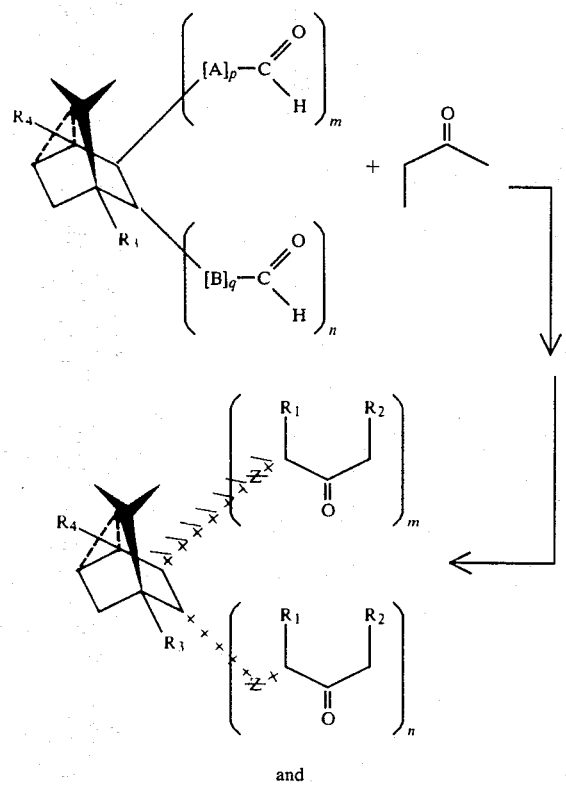

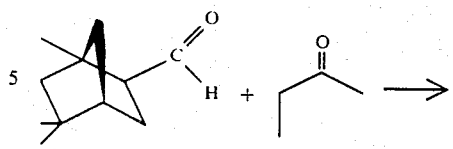

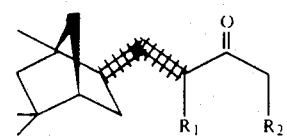

whereby a mixture of ketones is produced. This reaction is carried out under standard "aldol" condensation reaction conditions, that is, using a basic catalyst and reflux conditions with the basic catalyst being sodium hydroxide, potassium hydroxide, lithium hydroxide, barium hydroxide or calcium hydroxide. The reaction can be carried out using a "Soxhlet" apparatus in the laboratory or analogous apparatus in the plant. The reaction temperature may vary from about 40° C. up to about 150° C. and is preferably carried out at reflux conditions at atmospheric pressure. However, the reaction may be carried out at higher pressures and higher temperatures in pressure equipment which preferably is either glass-lined pressure equipment or stainless steel pressure equipment. At the end of the reaction, the reaction mixture is distilled by means of fractional distillation and the resulting products in admixture may be used "as is" for their organoleptic properties or may be used "as is" for further reaction or may be separated by means of commercial chromatographic techniques, e.g. "HPLC" techniques.

The resulting reaction product may be reduced using lithium aluminum hydride, sodium borohydride or potassium borohydride reducing agents according to the reactions:

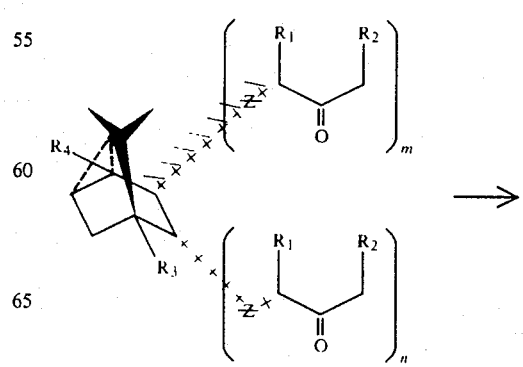

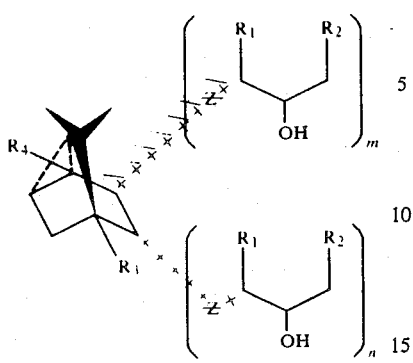

taken together with the reaction:

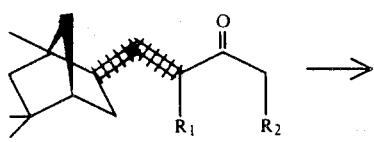

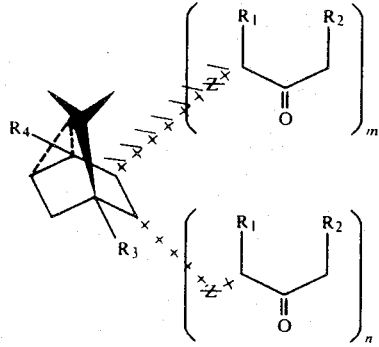

These reactions are preferably carried out in a solvent which is inert to the reaction mass such as diethylether or tetrahydrofuran under reflux conditions at atmospheric pressure. The reaction may be carried out at pressures higher than atmospheric at higher temperatures thereby resulting in shorter times of reaction. However, the yield of reaction product is not affected by the higher temperature of reaction. However, higher temperatures will vary the ratio of isomeric products produced without, however, materially affecting the organoleptic properties thereof. At the end of the reaction, the reaction product may be used "as is" for its organoleptic properties after appropriate fractional distillation or the reaction product after fractional distillation may be separated into the individual components of the mixture by standard chromatographic techniques, e.g. HPLC techniques.

Examples of mixtures of products and individual products produced according to the foregoing reaction sequence are set forth in Table I, infra:

TABLE I

| Structure of Product(s) and Example by which Produced | Fragrance Evaluation | Food Flavor Evaluation | Tobacco Flavor Evaluation |
|---|---|---|---|
| Reaction product of Example IV defined according to the structure:<br><br>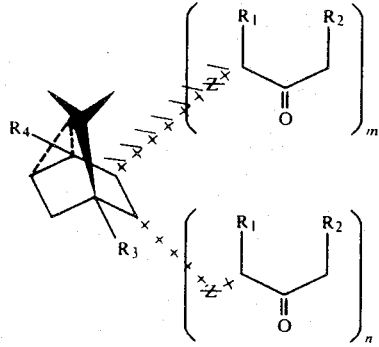<br><br>taken together with the compounds defined according to the structure:<br><br>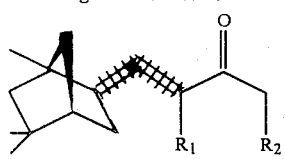<br><br>(mixture, bulked fractions 14–17). | A strong, woody, urine-like note with a buttery, caramel topnote. | An ionone-like raspberry, oriental, floral, violet aroma profile with a sweet, ionone-like, raspberry, fruity, taste profile with a raspberry aftertaste at 0.05 ppm. | A woody, sweet, oriental, raspberry, ionone-like aroma and taste prior to smoking with a woody, sweet, oriental, ionone-like taste on smoking in the main stream and the side stream. |
| Compound defined according to the structure: | Powerful sandalwood aroma with urine, sweet, floral | | |

TABLE I-continued

| Structure of Product(s) and Example by which Produced | Fragrance Evaluation | Food Flavor Evaluation | Tobacco Flavor Evaluation |
|---|---|---|---|
| 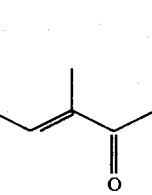 produced according to Example IV. | (muguet) undertone. | | |
| Mixture of compounds defined according to the structure: 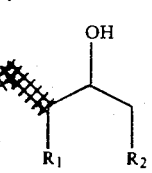 (mixture). | Powerful sandalwood aroma at 0.0001 ppm. | | |
| Mixture of compounds produced according to Example V, bulked fraction 6-14 defined according to the structure: 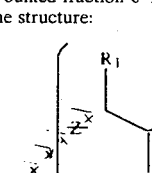 taken together with the mixture of compounds defined according to the structure: 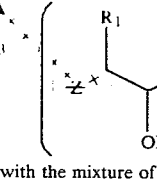 | A sandalwood, musky aroma profile. | A musky, fruity, ionone-like aroma with a lactonic taste at 0.1 ppm. | A woody, sandalwood, patchouli-like, cigar boxlike aroma and taste profile both prior to and on smoking in the main stream and the side stream. |

When the methyl substituted pinyl oxopentenes of our invention are used as food flavor adjuvants, the nature of the co-ingredients included with the methyl substituted pinyl oxopentenes of our invention used in formulating the product composition will also serve to alter, modify, augment or enhance the organoleptic properties of the ultimate foodstuff treated therewith.

As used herein as regards to flavor, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum", is intended herein to mean a composition which comprises a substantially water-insoluble, chewable plastic gum base such as chicle or substitutes therefor, including jelutong, guttakay, rubber or certain cosmetible natural or synthetic resins or waxes. Incorporated with the gum base in admixture therewith may be plasticizers or softening agents, e.g. glycerine, and a flavoring composition which incorporates one or more of the substituted norbornane carboxaldehyde derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious, particularly from an organoleptic standpoint whereby the ultimate flavor and/or aroma of a consumable material used is not caused to have unacceptable aroma and taste nuances. Such materials may in general be characterized as flavoring agents or vehicles comprising broadly stabilizers, thickeners, surface agents, conditioners, other flavorants and flavor intensifiers.

Stabilizer compounds include preservatives, e.g. sodium chloride, antioxidants, e.g. calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan, cellulose and cellulose derivatives such as carboxymethyl cellulose and methyl cellulose; natural and synthetic gums such as gum arabic, gum tragacanth, gelatin, proteinaceous materials, lipids. carbohydrates; starches, pectins and emulsifiers, e.g. mono- and diglycerides of fatty acids, skim milk powder, hexoses, pentoses, disaccharides, e.g. sucrose, corn syrup and the like.

Surface active agents include emulsifying agents, e.g. fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like, colorants, e.g. carminic acid, cochineal, tumeric and curcuma and the like; firming agents such as aluminum sodium sulfate, calcium chloride and calcium gluconate; texturizers, anti-caking agents, e.g. aluminum calcium sulfate and tribasic calcium phosphate; enzymes; yeast foods e.g. calcium lactate and calcium sulfate, nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alphamethyl-butyric acid, propionic acid, valeric acid, 2-methyl-2-pentenoic acid and 2-methyl-cis-3-pentenoic acid; ketones and aldehydes, e.g. acetaldehyde, acetophenone, acetone, acetyl methyl carbinol, acrolein, n-butanal, crotonal, diacetyl, 2-methyl butanal, beta-beta-dimethylacrolein, methyl-n-amyl ketone, n-hexanol, iso-pentanal, hydrocinnamic aldehyde, cis-3-hexenal, 2-heptanal, n-nonylaldehyde, 4-(p-hydroxyphenyl)-2-butanone, alpha-ionone, beta-ionone, methyl-3-butanone, benzaldehyde, beta-damascone, beta-damascenone, acetophone, 2-heptanone, o-hydroxyacetophone, 2-methyl-2-hepten-6-one, 2-octanone, 2-undecanone, 3-phenyl-4-pentenal, 2-phenyl-2-hexanal, 2-phenyl-2-pentenal, furfural, 5-methyl furfural, cinnamaldehyde, beta-cyclohomocitral, 2-pentanone, 2-pentenal and propanol; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, n-dodecane, methyl diphenyl, methyl naphthalene, mycrene, naphthalene, n-octadecane, n-tetradecane, tetramethyl naphthalene, n-trimethyl naphthalene, undecane, caryophyllene, 1-phellandrene, p-cymene and 1-alpha-pimene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isopropyl-4,5-dimethylpyrazine, 1-methyl-2-ethylpyrazine, tetramethylpyrazinne, trimethylpyrazine, essential oils such as jasmine absolute, cassia oil, cinnamon bark oil, rose absolute, orris absolute, lemon essential oil, Bulgarian rose, yara yara and vanilla, lactones such as delta nonalactone, gamma nonalactone, delta dodecalactone, gamma dodecalactone, sulfides, e.g. methyl sulfide and other materials such as maltol, acetoin and acetals (e.g. 1,1-diethoxyethane, 1,1-dimethoxyethane and dimethoxymethane).

The specific flavoring adjuvant selected for use may be either solid or liquid depending upon the desired physical form of the ultimate product, i.e. foodstuff, whether simulated or natural, and should, in any event, (i) be organoleptically compatible with the methyl substituted pinyl oxopentenes of our invention by not covering or spoiling the organoleptic properties (aroma and/or taste) thereof; (ii) be non-reactive with the methyl substituted pinyl oxopentenes of our invention and (iii) be capable of providing an environment in which the methyl substituted pinyl oxopentenes of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of the methyl substituted pinyl oxopentenes employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e. sufficient to alter, modify or enhance the organoleptic characteristics of the parent composition, whether foodstuff per se, chewing gum per se, medicinal product per se, toothpaste per se, or flavor composition.

The use of insufficient quantities of methyl substituted pinyl oxopentenes will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of methyl substituted pinyl oxopentenes ranging from a small but effective amount, e.g. 0.02 parts per million up to about 300 parts per million based on total composition are suitable. Concentrations in excess of the maximum quantity stated are not normally recommended, since they fail to provide commensurate enhancement of organoleptic properties. In those instances wherein methyl substituted pinyl oxopentenes are added to the foodstuff as an integral component of a flavoring composition, it is, of course, essential that the total amount of flavoring composition employed be sufficient to yield an effective concentration of methyl substituted pinyl oxopentenes in the foodstuff product.

Food flavoring compositions prepared in accordance with the present invention preferably contain methyl substituted pinyl oxopentenes in concentrations ranging from about 0.1% up to about 15% by weight of the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing methyl substituted pinyl oxopentenes with, for example, gum arabic, gum tragacanth, carrageenan and the like, and thereafter spray-drying the resultant mixture whereby to obtain the particulate solid product. Pre-prepared flavor mixes in powder form, e.g. fruit flavored powder mixes, are obtained by mixing the dried solid components e.g. starch, sugar and the like and one or more methyl substituted pinyl oxopentenes in a dry blender until the requisite degree of uniformity is achieved.

It is presently preferred to combine with methyl substituted pinyl oxopentenes of our invention, the following adjuvants:
p-hydroxybenzylacetone;
geraniol;
cassia oil;
acetaldehyde;
maltol;
ethyl methyl phenyl glycidate;
benzyl acetate;
dimethyl sulfide;
eugenol;
vanillin;
caryophyllene;
guaiacol;
ethyl pelargonate;
cinnamaldehyde;
methyl anthranilate;
5-methyl furfural;
isoamyl acetate;
isobutyl acetate;
cuminaldehyde;
alpha ionone;
cinnamyl formate;
ethyl butyrate;
methyl cinnamate;
acetic acid;
gamma-undecalactone;
naphthyl ethyl ether;
diacetyl;
furfural;
ethyl acetate;
anethole;
2,3-dimethyl pyrazine;
2- ethyl-3-methyl pyrazine;
3-phenyl-4-pentenal;
2-phenyl-2-hexanal;
2-phenyl-2-pentenal;
2-phenyl-4-pentenal diethyl acetal;
beta-damascone (1-crotonyl-2,6,6-trimethyl-cyclohex-1-ene);
beta-damascenone (1crotonyl2,6,6-trimethyl-cyclohexa-1,3-diene);
beta-cyclohomocitral (2,6,6-trimethylcyclohex-1-ene carboxaldehyde);
isoamyl butyrate;
cis-3-hexanol-1;
2-methyl-2-pentenoic acid;
elemecine (4allyl-1,2,6-trimethoxybenzene);
isoelemecine (4-propenyl 1,2,6-trimethoxybenzene); and 2-(4-hydroxy-4-methylpentyl)norbornadiene.

The methyl substituted pinyl oxopentenes of our invention can be used contribute sandalwood, urine-like, animal-like aromas with floral and muguet undertones and woody topnotes to perfume compositions, perfumed articles such as solid or liquid anionic, cationic, nonionic or zwitterionic detergents, fabric softener compositions, fabric softener articles, fabric optical brighteners, fabric conditioners, hair preparations and perfumed polymers. As olfactory agents, the methyl substituted pinyl oxopentenes of our invention can be formulated into or used as components of a perfume composition.

The term "perfume composition" is used herein to mean a mixture of organic compounds including for example, alcohols, aldehydes, ketones, nitriles, ethers, lactones and frequently hydrocarbons which are admixed so that the combined odors of the individual components produce a pleasant or desired fragrance. Such perfumed compositions usually contain (a) the main note of the "bouquet" or foundation stone of the composition; (b) modifiers which round off and accompany the main note; (c) fixatives which include odorous substances which lend a particular note to the perfume throughout all stages of evaporation, and substances which retard evaporation and (d) topnotes which are usually low-boiling, fresh-smelling materials.

In perfume compositions, the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of methyl substituted pinyl oxopentenes of our invention which will be effective in perfume compositions depends upon many factors including the other ingredients, their amounts and the effects which are desired. It has been found that perfume compositions containing as little as 0.5% of the methyl substituted pinyl oxopentenes of our invention or even less in perfume compositions containing as much as 70% of the methyl substituted pinyl oxopentenes of our invention can be used to impart interesting, sandalwood, animal-like, musky and urine-like aromas with floral and muguet undertones to perfumed articles, perfume compositions and colognes. Such perfumed articles include fabric softener compositions, perfumed polymers (e.g. perfumed microporous polyethylene and microporous polypropylene), drier-added fabric softeners, cosmetic powders, talcs, and solid or liquid anionic, cationic, nonionic or zwitterionic detergents. The amount employed can range up to 70% and will depend on considerations of cost, nature of the end product and the effect desired on the finished product and the particular fragrance sought.

Thus the methyl substituted pinyl oxopentenes of our invention can be used alone or in a perfume composition as an olfactory component in solid or liquid anionic, cationic, nonionic or zwitterionic detergents (including soaps), space odorants and deodorants; perfumes; colognes, toilet water, bath salts, hair preparations such as lacquers, brilliantines, pomades and shampoos; cosmetic preparations such as creams, deodorants, hand lotions and sun screens; powders such as talcs, face powders, dusting powders, perfumed polymers such as perfumed microporous thermoplastic polymers, e.g. perfumed polyethylene, perfumed polypropylene, perfumed polyesters or perfumed thermoset resins such as cross-linked polyacrylates, cross-linked polyurethanes and the like.

When used as an olfactory component of a perfumed article such as a solid or liquid anionic, cationic, nonionic or zwitterionic detergent or of a cosmetic powder or of a plastic polymer, as little as 0.01% of one or more of the methyl substituted pinyl oxopentenes of our invention will suffice to provide interesting musky, woody, animal-like, sandalwood-like aromas with floral and muguet undertones. Generally no more than 0.8% of the methyl substituted pinyl oxopentenes of our invention are required.

Thus the range of methyl substituted pinyl oxopentenes in the perfumed article may vary from about 0.01% up to about 0.8% of the overall perfurmed article.

In addition, the perfume compositions of our invention can contain a vehicle or carrier for the methyl substituted pinyl oxopentenes of our invention alone or with other ingredients. The vehicle can be a liquid such as an alcohol such as ethanol, a glycol such as propylene glycol or the like. The carrier can be an absorbent solid such as a gum (e.g. xanthan gum or guar gum), or components for encapsulating the composition as by coacervation (e.g. gelatin) or as by polymerization around a liquid perfume oil core as by polymerization of a urea formaldehyde polymer.

Also contemplated within the scope of this invention are mixtures of the methyl substituted pinyl oxopentenes of our invention taken further together with:

(i) 4-methyl-3-cyclohexene-1-carboxylic acid having the structure:

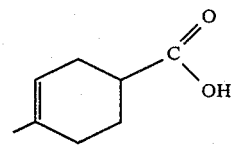

taken alone or taken further together with other compounds which yield sweaty, animal, leathery notes defined according to genera having the structures:

(ii)

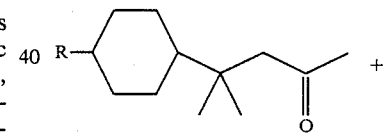

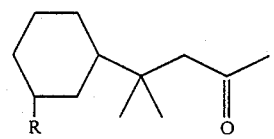

wherein R represents t-butyl or t-amyl as more specifically described in United States Letters Patent No. 3,702,343 issued on Nov. 7, 1972, the disclosure for which is incorporated by reference herein.

In addition to the methyl substituted pinyl oxopentenes of our invention and to the compounds having the structure:

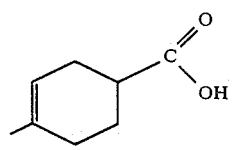

and/or the compounds defined according to the structures:

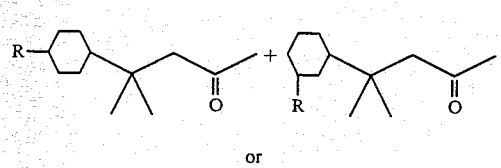

or

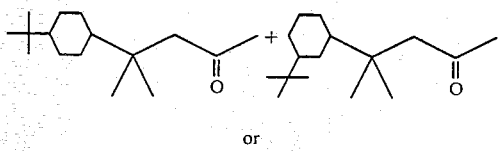

or

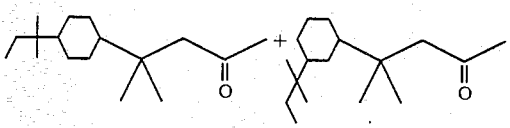

it is contemplated that these compounds can also be used in admixture with cedrol alkyl ethers disclosed in United States Letters Patent No. 3,373,208 issued on Mar. 12, 1968, the disclosure of which is incorporated by reference herein. The cedrol alkyl ethers of U.S. Pat. No.3,373,208 are defined according to the generic structure:

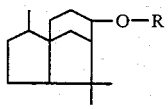

wherein R represents methyl, ethyl, propyl, butyl, allyl or methallyl.

Contemplated within the scope of our invention are ratios of methyl substituted pinyl oxopentenes:4-methyl-3-cyclohexene-1-carboxylic acid or 2-methyl-2-(t-alkyl cyclohexyl) pentan-4-one or cedrol alkyl ethers of from 1:30 to 30:1 (mole ratios).

The compounds defined according to the structure:

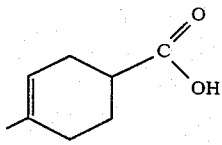

may be prepared by methods well known in the art, e.g. according to the reaction:

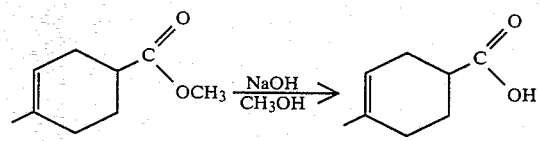

as further disclosed in Example I of application for United States Letters Patent Ser. No. 299,211 filed on Sept. 3, 1981, the disclosure of which is incorporated by reference herein.

When using the mixtures of our invention, that is the methyl substituted pinyl oxopentenes and the compounds defined according to the structure:

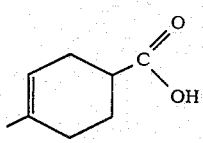

or the compounds defined according to the structures:

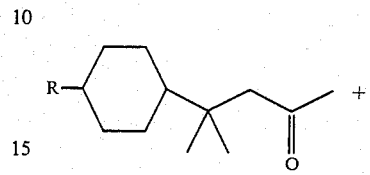

or the compound defined according to the structure:

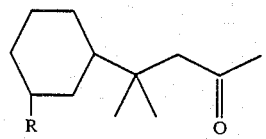

the additional notes provided to the perfume compositions or perfumed articles as set forth, supra, are cumin-like, sweaty, and cedar-like with castoreum undertones.

Furthermore, the methyl substituted pinyl oxopentenes produced according to the processes of our invention are capable of supplying and/or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor as well as methods of making the same which overcome specific problems heretofore encountered in which specific desired Turkish-type, oriental or Virginia tobacco aroma and taste nuances thereof are created or enhanced and may be readily controlled and maintained at the desired uniform level regardless of variations in the tobacco components of the blend.

This invention further provides improved tobacco additives and methods whereby various Virginia-type, oriental-type and Turkish-type tobacco notes may be imparted to smoking tobacco products and may be readily varied and controlled to produce the desired uniform flavor characteristics.

In carrying out this aspect of our invention, we add to smoking tobacco materials or a suitable substitute therefor (e.g. dried lettuce leaves) an aroma and flavor additive containing as an active ingredient one or more methyl substituted pinyl oxopentenes produced according to the processes of our invention.

In addition to the methyl substituted pinyl oxopentenes produced according to the processes of our invention, other flavoring and aroma additives may be added to the smoking tobacco materials or substitute therefor either separately or in admixture with the methyl substituted pinyl oxopentenes produced according to the processes of our invention as follows:

(i) Synthetic Materials:
   Beta-ethyl-cinnamaldehyde;
   Beta-cyclohomocitral;
   Eugenol;
   Dipentene;
   Beta-damascenone;
   Beta-damascone;
   Maltol;
   Ethyl maltol;
   Delta-undecalactone;
   Delta-decalactone;
   Benzaldehyde;
   Amyl acetate;
   Ethyl butyrate;
   Ethyl valerate;
   Ethyl acetate;
   2-hexenol-1;
   2-methyl-5-isopropyl-1,3-nonadiene-8-one;
   2,6-dimethyl-2,6-undecadiene-10-one;
   2-methyl-5-isopropyl acetophenone;
   2-hydroxy-2,5,5,8a-tetramethyl-1-(2-hydroxyethyl)-decahydronaphthalene;
   Dodecahydro-3a,6,6,9a-tetramethylnaphtho[2,1,b]-furan;
   4-hydroxy hexanoic acid, gamma lactone and polyisoprenoid hydrocarbons defined in Example V or U.S. Pat. No. 3,589,372, issued on June 29, 1971.

(ii) Natural Oils:
   Celery seed oil;
   Coffee extract;
   Bergamot oil;
   Cocoa extract;
   Nutmeg oil;
   Origanum oil.

An aroma and flavoring concentrate containing one or more of the methyl substituted pinyl oxopentenes produced according to the processes of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of natural and/or sweet and/or woody, e.g. sandalwoody, and/or oriental notes, we have found that satisfactory results are obtained if the proportion by weight of the sum total of the methyl substituted pinyl oxopentenes produced according to the processes of our invention to smoking tobacco material is between 200 ppm and 2,000 ppm (0.02%–0.20%) of the active ingredients to the smoking tobacco material. We have further found that satisfactory results are obtained if the proportion by weight of the sum total of the methyl substituted pinyl oxopentenes produced according to the processes of our invention used to flavoring material is between 2,500 and 15,000 ppm (0.25%–1.5%).

Any convenient method for incorporating the methyl substituted pinyl oxopentenes produced according to the processes of our invention in the tobacco product may be employed. Thus, the methyl substituted pinyl oxopentenes produced according to the processes of our invention taken alone or along with other flavoring additives may be dissolved in a suitable solvent such as ethanol, n-pentane, diethylether, and/or other volatile organic solvents and the resulting solution may either be sprayed on the cured, cased and blended tobacco material or the tobacco material may be dipped into such solution. Under certain circumstances, a solution of the methyl substituted pinyl oxopentenes produced according to the process of our invention taken alone or further together with other flavoring additives as set forth above, may be applied by means of a suitable applicator such as a brush or roller on the paper or leaf wrapper for the smoking product, or it may be applied to the filter by either spraying, dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the methyl substituted pinyl oxopentenes produced according to the process of our invention in excess of our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the mixture of alcohols produced according to Example V, infra (bulked fractions 10–20 of the distillation product) defined according to the formula:

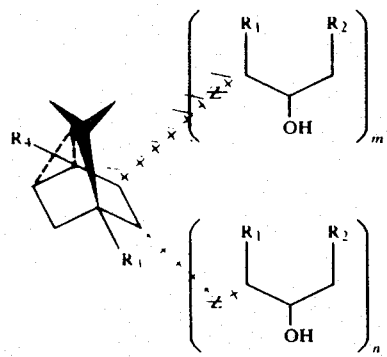

taken together with the compounds defined according to the structure:

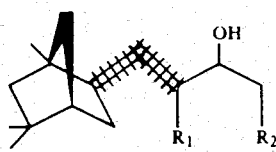

(wherein in the mixture, in each of the compounds Z represents methylidene defined according to the structure:

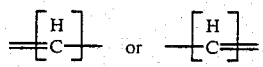

ethylidene defined according to the structure:

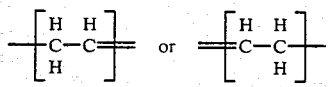

or ethylenyl defined according to the structure:

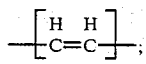

wherein one of the dashed line represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

represents a carbon-carbon single bond and the other of the lines:

represents a carbon-carbon single bond or a carbon-carbon double bond; wherein one of the lines:

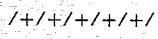

represents a carbon-carbon single bond and the other of the lines:

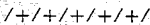

represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

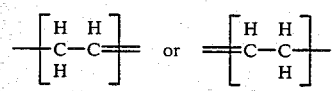

or ethylenyl having the structure:

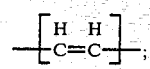

(ii) when one of $R_3$ or $R_4$ is methyl, then either the dashed line at the 7-5 position or the dashed line at the 7-4 position is a carbon-carbon single bond; and Z represents methylidene defined according to the structure:

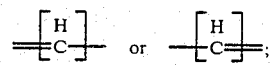

(iii) when $R_3$ is methyl, then n is 1 and m is 0 and $R_4$ is hydrogen; and
(iv) when $R_4$ is methyl, then $R_3$ is hydrogen, n is 0 and m is 1
and wherein one of the lines:

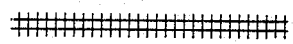

is a carbon-carbon double bond and the other of the lines:

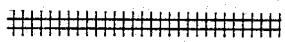

is a carbon-carbon single bond) in an amount to provide a tobacco composition containing 800 ppm by weight of the mixture of alcohols of Example V, infra, on a dry basis. Thereafter, the volatile ethyl alcohol is removed by evaporation and the tobacco is manufactured into cigarettes by the usual techniques. The cigarettes, when treated as indicated, have desired and pleasing aromas (increased smoke body sensation in the mouth with enhanced tobacco-like notes and pleasant aromatic nuances) which is detectable in the main and side streams when the cigarette is smoked. This aroma is described as having sweet, woody, sandalwood, patchouli, Havana cigar and burley characteristics.

While our invention is particularly useful in the manufacture of smoking tobacco, such as cigarette tobacco, cigar tobacco and pipe tobacco, other tobacco products formed from sheeted tobacco dust or fines may also be used. Likewise, the methyl substituted pinyl oxopentenes produced according to the processes of our invention can be incorporated with materials such as filter tip materials, seam paste, packaging materials and the like which are used along with tobacco to form a product adapted for smoking. Furthermore, the methyl substituted pinyl oxopentenes produced according to the process of our invention can be added alone or in admixture to certain tobacco substitutes of natural or synthetic origin (e.g. dried lettuce leaves) and, accordingly, by the term "tobacco" as used throughout this specification, is meant any composition intended for human consumption by smoking whether composed of tobacco plant parts, substitute materials or both.

The following examples serve to illustrate our invention and the invention is to be considered restricted thereto only as indicated in the appended claims.

All parts and percentages given herein are by weight unless otherwise specified.

EXAMPLE I

PREPARATION OF OXOALKYL SUBSTITUTED PINANE DERIVATIVES

Reactions:

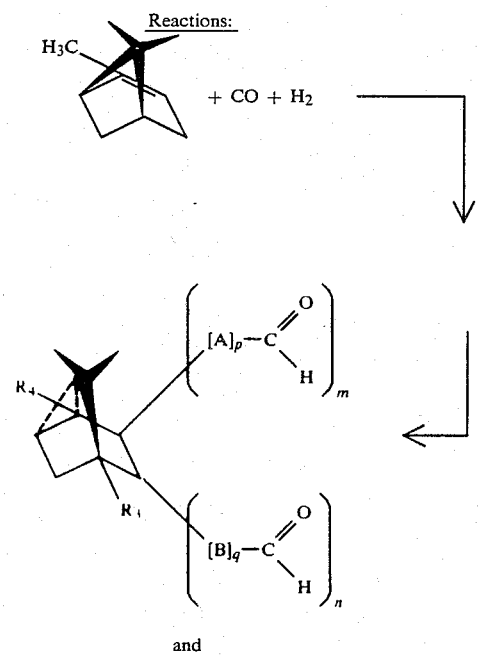

and

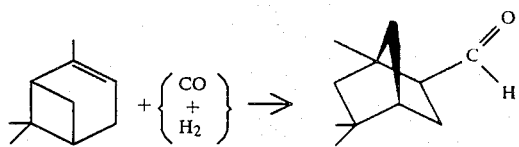

(wherein a mixture is produced wherein in the mixture one of the dashed lines in each of the compounds at the 7-5 or 7-4 positions represent a carbon-carbon single bond and the other of the dashed lines at the 7-5 or 7-4 positions represents no bond; wherein one of $R_3$ or $R_4$ represents hydrogen and the other of $R_3$ or $R_4$ represents hydrogen or methyl; wherein m=0 or 1 with the sum of m+n being equal to 1; wherein A and B each represents methylene defined according to the structure:

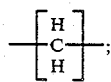

wherein
p=0 or 1 and q=0 or 1 with the provisos that:
(i) when the dashed line at the 7-4 position is a carbon-carbon single bond, then $R_3$ and $R_4$ are both hydrogen, m is 0, n is 1 and q is 1;
(ii) when one of $R_3$ or $R_4$ is methyl and the other of $R_3$ or $R_4$ is hydrogen, then p and q are both 0;
(iii) when $R_3$ is methyl, then $R_4$ is hydrogen and the dashed line at the 7-5 position or the dashed line at the 7-4 position is a carbon-carbon single bond; and m is 0; n is 1 and q is 0;
(iv) when $R_4$ is methyl and $R_3$ is hydrogen, then n is 0 and m is 1 and p is 0 and one of the dashed lines at the 7-5 position or the 7-4 position is a carbon-carbon single bond).

Into a 3 liter autoclave equipped for pressures up to 6,000 psig is placed 200 ml dicobalt octacarbonyl catalyst; and 4 pounds of alpha pinene. The autoclave is closed and the vessel is pressurized with a 1:1 mole ratio of carbon monoxide and hydrogen and maintained at 185°-208° C. and 4,000 psig pressure while adding the mixture of carbon monoxide and hydrogen. The carbon monoxide:hydrogen mixture is added until seven cubic feet (at atmospheric pressure and 20° C.) of each of the carbon monoxide and hydrogen is added to the reaction mass.

At the end of the reaction, the autoclave is depressurized and opened. The resulting reaction mass is wsahed five times with equal volumes of water. The resulting reaction product is dried over anhydrous magnesium sulfate and distilled on a 1' silver mirror column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 30/34 | 70/93 | 10/10 | 4:1 | 23.2 |
| 2 | 59 | 86 | 10 | 4:1 | 21.8 |
| 3 | 65 | 88 | 10 | 7:1 | 25.1 |
| 4 | 65 | 89 | 10 | 9:1 | 71.3 |
| 5 | 65/75 | 80/93 | 10/10 | 9:1 | 19.6 |
| 6 | 70 | 94 | 10 | 17:3 | 39.8 |
| 7 | 69 | 94 | 10 | 17:3 | 49.9 |
| 8 | 74 | 100 | 10 | 17:3 | 39.4 |
| 9 | 74 | 101 | 10 | 17:3 | 39.9 |
| 10 | 74 | 101 | 10 | 17:3 | 35.7 |
| 11 | 81 | 100 | 10 | 17:3 | 22.1 |
| 12 | 80/87 | 101/104 | 10/9 | 17:3 | 29.1 |
| 13 | 90 | 106 | 8 | 17:3 | 39.3 |
| 14 | 90 | 107 | 7 | 17:3 | 40.7 |
| 15 | 94 | 108 | 7 | 17:3 | 44.0 |
| 16 | 94 | 113 | 7 | 17:3 | 64.8 |
| 17 | 93/95 | 113/136 | 8/7 | 4:1 | 55.7 |
| 18 | 50 | 210 | 2.5 | 4:1 | 24.0 |

Fractions 3–8 are bulked for subsequent reaction in Example II.

FIG. A is the GLC profile for the alpha pinene reactant for Example I (conditions: 10'×⅛" 5% Carbowax 20M column programmed at 100°-220° C. at 2° C. per minute). The peak indicated by reference numeral "100" is the peak for the alpha pinene.

FIG. AA is the GLC profile for the reaction product of this example (conditions: 2'×⅛" Carbowax column programmed from 100°-220° C. at 6° C. per minute).

EXAMPLE II

PREPARATION OF METHYL SUBSTITUTED PINYL OXOPENTENE MIXTURE

Reactions:

(mixture produced wherein in the mixture, in each of the compounds, Z represents methylidene defined according to the structure:

$$-\begin{bmatrix} H \\ C \\ \end{bmatrix}- \quad \text{or} \quad -\begin{bmatrix} H \\ C \\ \end{bmatrix}-$$

ethylidene defined according to the structure:

$$-\begin{bmatrix} H & H \\ C-C \\ H \end{bmatrix}- \quad \text{or} \quad =\begin{bmatrix} H & H \\ C-C \\ H \end{bmatrix}-$$

or ethylenyl defined according to the structure:

$$-\begin{bmatrix} H & H \\ C=C \end{bmatrix}-;$$

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

+ + + + represents a carbon-carbon single bond and the other of the lines:

+ + + + represents a carbon-carbon single bond or a carbon-carbon double bond; wherein one of the lines:

/+/+/+/+/+/ represents a carbon-carbon single bond and the other of the lines:
/+/+/+/+/+/ represents a carbon-carbon single bond or a carbon-carbon double bond; with the provisos that:

(i) when $R_3$ and $R_4$ are each hydrogen, the dashed line at the 7–5 position is a carbon-carbon single bond; n=0 and m is 1; Z represents ethylidene having the structure:

$$-\begin{bmatrix} H & H \\ C-C \\ H \end{bmatrix}- \quad \text{or} \quad =\begin{bmatrix} H & H \\ C-C \\ H \end{bmatrix}-$$

or ethylenyl having the structure:

$$-\begin{bmatrix} H & H \\ C=C \end{bmatrix}-;$$

(ii) when one of $R_3$ or $R_4$ is methyl, then either the dashed line at the 7–5 position or the dashed line at the 7–4 position is a carbon-carbon single bond; and Z represents methylidene defined according to the structure:

$$-\begin{bmatrix} H \\ C \\ \end{bmatrix}- \quad \text{or} \quad -\begin{bmatrix} H \\ C \\ \end{bmatrix}-;$$

(iii) when $R_3$ is methyl, than n is 1 and m is 0 and $R_4$ is hydrogen; and (iv) when $R_4$ is methyl, then $R_3$ is hydrogen, n is 0 and m is 1 wherein one of the lines:

######## is a carbon-carbon double bond and the other of the lines:

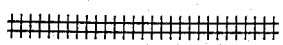

is a carbon-carbon single bond).

Into a three-neck reaction flask equipped with reflux condenser, magnetic stirrer, thermometer and addition funnel is added 50 ml of methanol and 1.5 grams of potassium hydroxide. The resulting mixture is stirred until all the potassium hydroxide is dissolved. The reaction flask is cooled to 10° C. and 25 grams of the reaction product of Example I, bulked fractions 3-8, a mixture defined according to the structure:

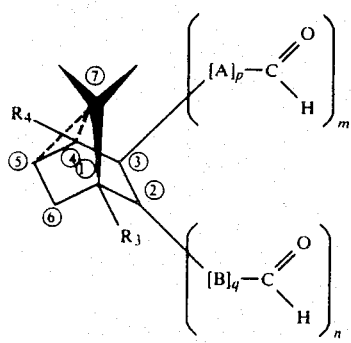

taken together with the compound having the structure:

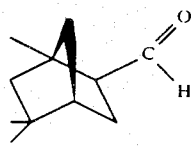

is added dropwise from the addition funnel over a one-hour period to the reaction mass.

The reaction mixture is allowed to warm to room temperature (23° C.) and 32 grams of methyl ethyl ketone is added dropwise over a 2.5 hour period while maintaining the reaction mass at room temperature. The reaction mass is monitored for completion of reaction using GLC. The reaction mass is heated at the end of a 16 hour period to 45°-50° C. and maintained at 45°-50° C. for a period of six hours.

The reaction mass is then diluted with saturated sodium chloride solution (75 ml) and extracted with four 30 ml volumes of toluene. The toluene extracts are combined and washed with three volumes of saturated sodium chloride followed by two volumes of water and one volume of saturated sodium chloride. The reaction mass is then dried over anhydrous magnesium sulfate and the solvent is removed leaving 36.3 grams of crude material which is distilled on a microvigreux column to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 49/66 | 96/115 | 3.2 | 3.1 |
| 2 | 83 | 115 | 1 | 1.8 |
| 3 | 84 | 118 | 1 | 3.2 |
| 4 | 86 | 119 | 1 | 2.6 |
| 5 | 86 | 124 | 1 | 2.2 |
| 6 | 87 | 131 | 1 | 1.9 |
| 7 | 87 | 135 | 1 | 2.9 |
| 8 | 104 | 166 | 1.8 | 3.2 |
| 9 | 107 | 190 | 1.9 | 1.0 |

FIG. 1 is the GLC profile of the reaction mass after the 16-hour reaction time at room temperature (conditions: 10′×⅛″ 5% Carbowax column programmed at 100°-220° C. at 4° C. per minute). The peak indicated by reference numeral "1" is the peak for the compound having the structure:

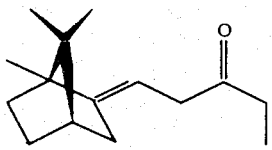

The peak indicated by reference numeral "3" is for the compound having the structure:

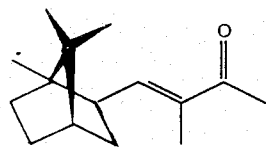

The peaks indicated by reference numerals "4", "5" and "6" are for unreacted aldehydes defined according to the structure:

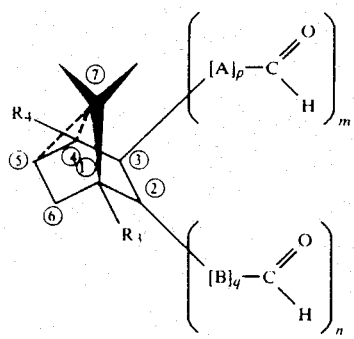

as well as the compound having the structure:

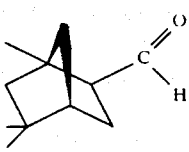

In addition, the compound defined according to the structure:

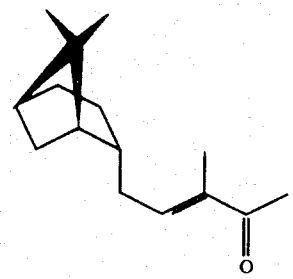

is also formed in a minor amount.

In addition, an important component for the aroma of sandalwood is formed which is a mixture of compounds defined according to the structure:

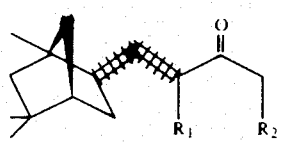

wherein in the mixture one of $R_1$ or $R_2$ is methyl and the other of $R_1$ or $R_2$ is hydrogen; and one of the lines:

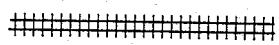

is a carbon-carbon double bond and the other of the lines:

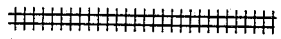

is a carbon-carbon single bond.

FIG. 2 is the mass spectrum for the peak indicated by reference numeral "1" on FIG. 1, for the compound having the structure:

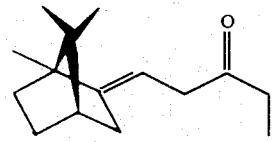

FIG. 3 is the mass spectrum for the peak indicated by reference numeral "3" on FIG. 1 for the compound defined according to the structure:

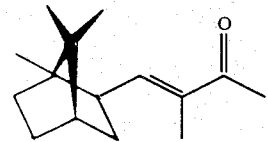

FIG. 4 is the NMR spectrum for the peak indicated by reference numeral "1" of FIG. 1 for the compound having the structure:

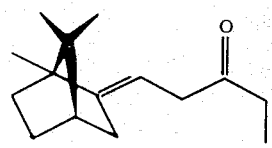

FIG. 5 is the NMR spectrum for the peak indicated by reference numeral "3" on FIG. 1, for the compound defined according to the structure:

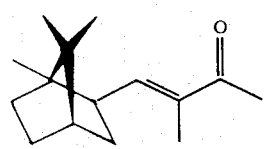

FIG. 6 is the infra-red spectrum for the peak indicated by reference numeral "1" on FIG. 1 for the compound having the structure:

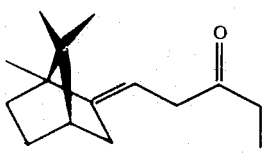

FIG. 7 is the infra-red spectrum for the peak indicated by reference numeral "3" of FIG. 1 for the compound having the structure:

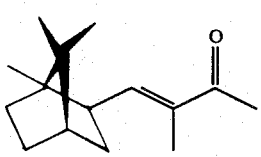

EXAMPLE III

PREPARATION OF OXOALKYL SUBSTITUTED PINANE DERIVATIVE MIXTURE

Reactions:

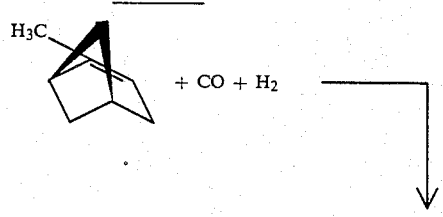

-continued
Reactions:

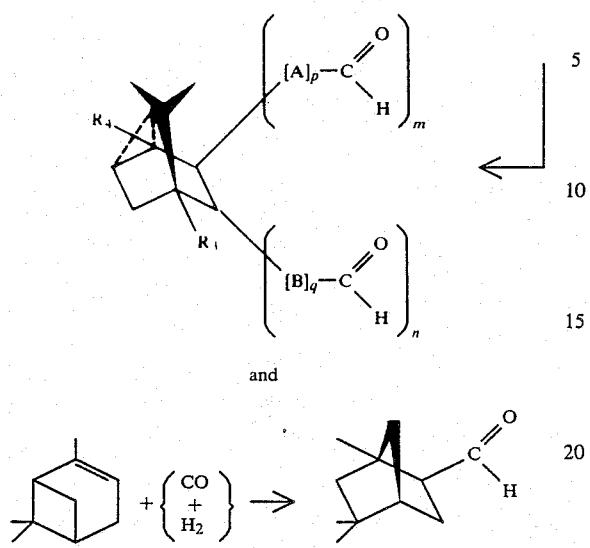

and (a mixture being produced wherein in the mixture one of the dashed lines in each of the compounds at the 7-5 or 7-4 positions represents a carbon-carbon single bond and the other of the dashed lines at the 7-5 or 7-4 positions represents no bond; wherein one of $R_3$ or $R_4$ represents hydrogen and the other of $R_3$ or $R_4$ represents hydrogen or methyl; wherein $m=0$ or 1 with the sum of $m+n$ being equal to 1; wherein A and B each represents methylene defined according to the structure:

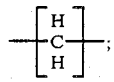

wherein
p=0 or 1 and q=0 or 1 with the provisos that:
(i) when the dashed line at the 7-5 position is a carbon-carbon single bond, then $R_3$ and $R_4$ are both hydrogen, m is 0, n is 1 and q is 1;
(ii) when one of $R_3$ or $R_4$ is methyl and the other of $R_3$ or $R_4$ is hydrogen, then p and q are both 0;
(iii) when $R_3$ is methyl, then $R_4$ is hydrogen and the dashed line at the 7-5 position or the dashed line at the 7-4 position is a carbon-carbon single bond; and m is 0; n is 1 and q is 0;
(iv) when $R_4$ is methyl and $R_3$ is hydrogen, then n is 0 and m is 1 and p is 0 and one of the dashed lines at the 7-5 position or the 7-4 position is a carbon-carbon single bond).

Into an autoclave equipped for 6,000 psig pressure is placed 4,000 grams of alpha pinene and 125 ml of dicobalt octacarbonyl catalyst. The autoclave is closed and is pressurized with an equimolar mixture of carbon monoxide and hydrogen to a pressure of 4,000 psig. The reaction mixture is heated to a temperature in the range of 200°-220° C. at a pressure of 4,000 psig until 8 cubic feet of carbon monoxide and 8 cubic feet of hydrogen are absorbed (conditions: 1 atmosphere at 20° C.). At the end of the reaction, the autoclave is depressurized and opened yielding 3,870 grams of reaction product.

The resulting material is washed with four volumes of water. The resulting material is then dried over anhydrous magnesium sulfate and distilled on a 4" Splash column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 27/40 | 38/53 | 5/5 | 16.2 |
| 2 | 50 | 65 | 15 | 61.8 |
| 3 | 56 | 72 | 15 | 77.8 |
| 4 | 59 | 78 | 15 | 76.2 |
| 5 | 63 | 89 | 15 | 91.6 |
| 6 | 83 | 103 | 10 | 70.1 |
| 7 | 85 | 93 | 4 | 196.2 |
| 8 | 93 | 109 | 3 | 217.3 |
| 9 | 105 | 165 | 3 | 173.7 |
| 10 | 114 | 210 | 3 | 24.4 |

EXAMPLE IV

PREPARATION OF METHYL SUBSTITUTED PINYL OXOPENTENE MIXTURE

Reactions:

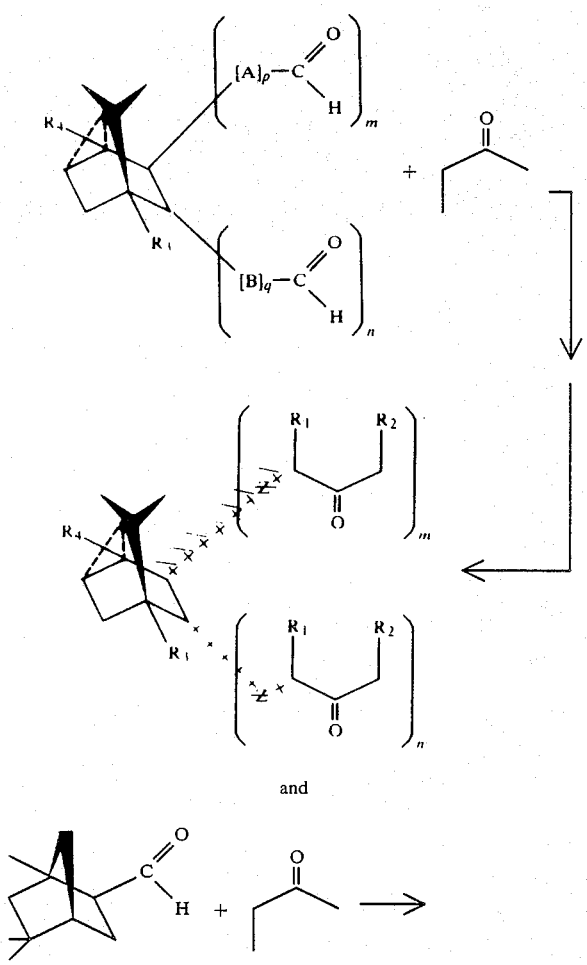

-continued
Reactions:

[structure shown]

(mixture produced wherein m in the mixture, in each of the compounds, Z represents methylidene defined according to the structure:

$$=\left[\begin{array}{c}H\\C\end{array}\right]- \quad \text{or} \quad -\left[\begin{array}{c}H\\C\end{array}\right]=$$

ethylidene defined according to the structure:

$$-\left[\begin{array}{cc}H & H\\C-C\\H\end{array}\right]= \quad \text{or} \quad =\left[\begin{array}{cc}H & H\\C-C\\ & H\end{array}\right]-$$

or ethylenyl defined according to the structure:

$$-\left[\begin{array}{cc}H & H\\C=C\end{array}\right]-;$$

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

+ + + + represents a carbon-carbon single bond and the other of the lines:

+ + + + represents a carbon-carbon single bond or a carbon-carbon double bond; wherein one of the lines:

/+/+/+/+/+/ represents a carbon-carbon single bond and the other of the lines:

/+/+/+/+/+/ represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

$$-\left[\begin{array}{cc}H & H\\C-C\\H\end{array}\right]= \quad \text{or} \quad =\left[\begin{array}{cc}H & H\\C-C\\ & H\end{array}\right]-$$

or ethylene having the structure:

$$-\left[\begin{array}{c}H & H\\C=C\end{array}\right]-;$$

(ii) when one of $R_3$ or $R_4$ is methyl, then either the dashed line at the 7-5 position or the dashed line at the 7-4 position is a carbon-carbon single bond; and Z represents methylidene defined according to the structure:

$$=\left[\begin{array}{c}H\\C\end{array}\right]- \quad \text{or} \quad -\left[\begin{array}{c}H\\C\end{array}\right]=;$$

(iii) when $R_3$ is methyl, then n is 1 and m is 0 and $R_4$ is hydrogen; and
(iv) when $R_4$ is methyl, then $R_3$ is hydrogen, n is 0 and m is 1
and wherein one of the lines:

████████████████ is a carbon-carbon double bond and the other of the lines:

████████████████ is a carbon-carbon single bond).

Into a five liter, three-neck reaction flask equipped with thermometer, condenser, addition funnel, mechanical stirrer, wet ice cooling bath and constant temperature warming bath, is placed 1,650 ml anhydrous methyl alcohol and 23.3 grams of potassium hydroxide. The mixture is stirred until all the potassium hydroxide is dissolved. The resulting mixture is cooled to 10° C. and 405 grams of the mixture of aldehydes prepared according to Example III (bulked fractions 7 and 8) defined according to the structure:

[structure shown with $R_4$, $R_1$, $[A]_p$, $[B]_q$, positions 1-7]

taken together with the compound having the structure:

[structure shown]

is added dropwise over a period of approximately one hour to the reaction mass with stirring. The mixture is then allowed to warm to room temperature (23° C.) and 533 grams of methyl ethyl ketone is added to the reaction mass, dropwise, over a 2.5 hour period at room temperature.

The reaction mixture is then heated to approximately 45° C. for a period of six hours. The reaction mass is then diluted with 750 ml saturated sodium chloride solution at room temperature and the aqueous phase is extracted with four volumes of toluene. The toluene extracts are combined and washed with three 1 liter volumes of saturated sodium chloride followed by two 1 liter volumes of water and one 1 liter volume of saturated sodium chloride solution.

The resulting product (weight 428.7 grams) is then distilled yielding the following fractions:

| Fraction Number | Vapor Temp (°C.) | Liquid Temp (°C.) | Pressure mm/Hg. | Reflux Ratio | Weight of Fraction (grams) |
|---|---|---|---|---|---|
| 1 | 32/33 | 100/106 | 3.5/2.2 | 4:1 | 14.7 |
| 2 | 57 | 107 | 2.0 | 4:1 | 10.8 |
| 3 | 65 | 108 | 1.9 | 4:1 | 9.1 |
| 4 | 77 | 114 | 1.9 | 4:1 | 12.2 |
| 5 | 75 | 119 | 1.9 | 4:1 | 26.7 |
| 6 | 80 | 122 | 1.8 | 9:1 | 16.3 |
| 7 | 80 | 125 | 1.8 | 9:1 | 18.2 |
| 8 | 81 | 129 | 1.8 | 9:1 | 13.8 |
| 9 | 86 | 130 | 1.8 | 9:1 | 20.5 |
| 10 | 89 | 130 | 1.8 | 9:1 | 14.1 |
| 11 | 69/86 | 137/138 | 1.8/1.8 | 9:1/9:1 | 10.6 |
| 12 | 85 | 139 | 1.8 | 9:1 | 15.5 |
| 13 | 89 | 140 | 1.8 | 9:1 | 12.2 |
| 14 | 88 | 140 | 1.8 | 17.3 | 21.0 |
| 15 | 88 | 140 | 1.8 | 17.3 | 18.8 |
| 16 | 86 | 142 | 1.6 | 17.3 | 20.0 |
| 17 | 84 | 145 | 1.6 | 17.3 | 18.4 |
| 18 | 84 | 150 | 1.6 | 17.3 | 20.6 |
| 19 | 88 | 170 | 1.6 | 17.3 | 22.6 |
| 20 | 35 | 210 | 1.4 | 17.3 | 19.7 |

FIG. 8 is the GLC profile for the crude reaction product, prior to distillation (conditions: 10'×⅛" 5% Carbowax column programmed at 100°–220° C. at 4° C. per minute). The peak indicated by reference numeral "15" is the peak for the compound defined according to the structure:

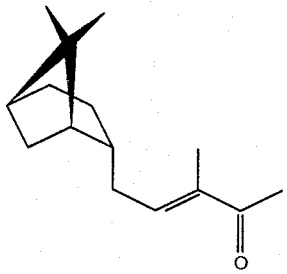

The peaks indicated by reference numerals "11", "12", "13" and "14" are peaks for other ketones in the reaction mass defined according to the structures:

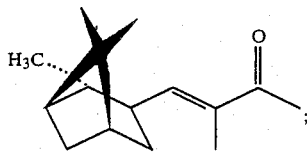

-continued

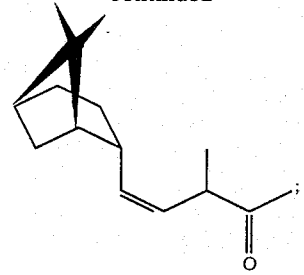

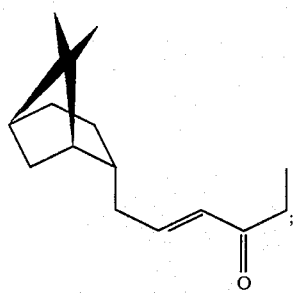

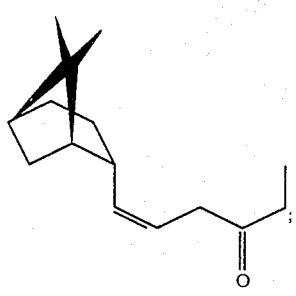

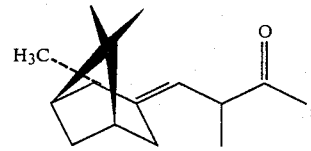

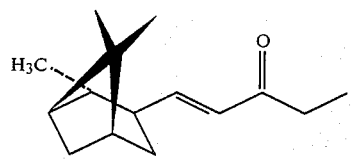

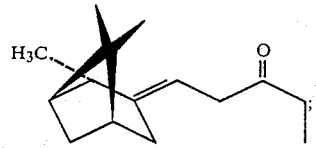

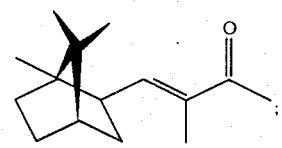

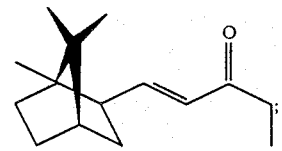

-continued

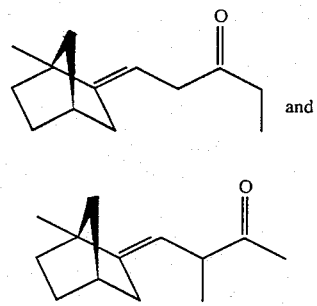
and

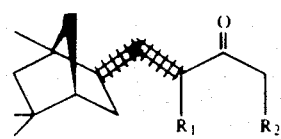

In addition, other peaks on the GLC profile are indicative of the mixture of compounds defined according to the structure:

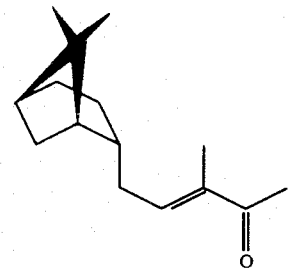

wherein in the mixture, one of $R_1$ or $R_2$ is methyl and the other of $R_1$ or $R_2$ is hydrogen; and wherein one of the lines:

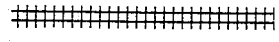

is a carbon-carbon double bond and the other of the lines:

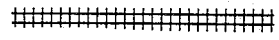

is a carbon-carbon single bond.

FIG. 9 is the mass spectrum for the peak indicated by the reference numeral "15" of FIG. 8 for the compound defined according to the structure:

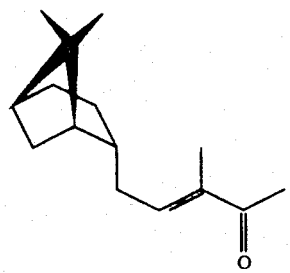

FIG. 10 is the NMR spectrum for the peak indicated by reference numeral "15" of FIG. 8, having the structure:

EXAMPLE V

PREPARATION OF METHYL SUBSTITUTED PINYL HYDROXY PENTENE MIXTURE

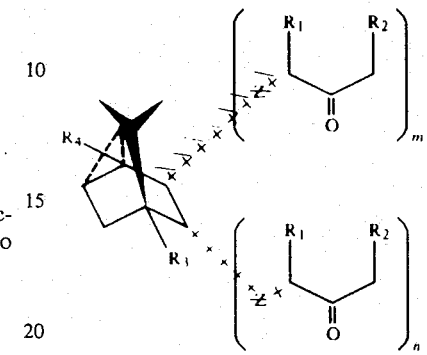

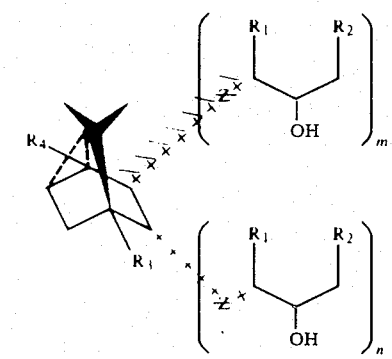

and

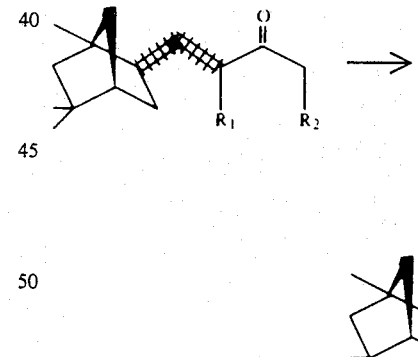

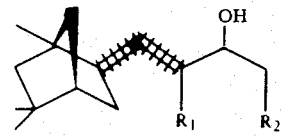

(mixture produced wherein in the mixture, in each of the compounds, Z represents methylidene defined according to the structure:

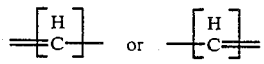

ethylidene defined according to the structure:

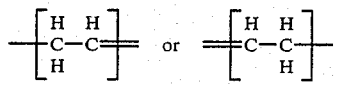

or ethylenyl defined according to the structure:

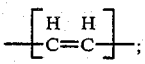

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

represents a carbon-carbon single bond and the other of the lines:

represents a carbon-carbon single bond or a carbon-carbon double bond; wherein one of the lines:

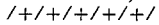

represents a carbon-carbon single bond and the other of the lines:

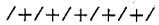

represents a carbon-carbon single bond or a carbon-carbon double bond; with the provisos that:
(i) when $R_3$ and $R_4$ are each hydrogen, the dashed line at the 7–5 position is a carbon-carbon single bond; n=0 and m is 1; Z represents ethylidene having the structure:

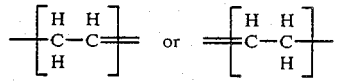

or ethylenyl having the structure:

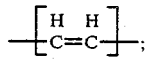

(ii) when one of $R_3$ or $R_4$ is methyl, then either the dashed line at the 7–5 position or the dashed line at the 7–4 position is a carbon-carbon single bond; and Z represents methylidene defined according to the structure:

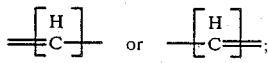

(iii) when $R_3$ is methyl, then n is 1 and m is 0 and $R_4$ is hydrogen; and
(iv) when $R_4$ is methyl, then $R_3$ is hydrogen, n is 0 and m is 1
and wherein one of the lines:

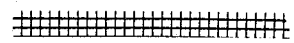

is a carbon-carbon double bond and the other of the lines:

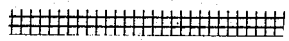

is a carbon-carbon single bond).

Into a 1 liter reaction flask equippd with mechanical stirrer, thermometer, condenser, addition funnel and nitrogen purge apparatus is placed 200 ml anhydrous diethylether and 4.0 grams of lithium aluminum hydride.

50 grams (0.23 moles) of the distillation product (bulked fractions 14–17) of the reaction product of Example IV defined according to the structures:

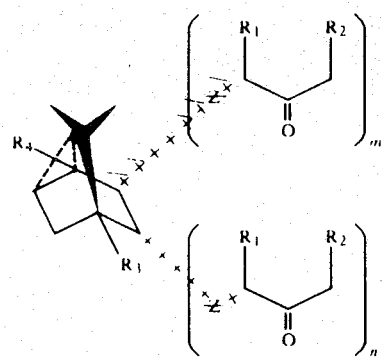

taken together with the structure:

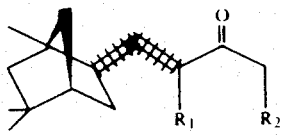

are then intimately admixed and dissolved in 50 ml anhydrous diethylether. The resulting ether-ketone solution is then added, with stirring over a period of one hour, to the reaction mass which exotherms to 34° C. The reaction mass, after addition of the ketone mixture, is then stirred for a period of three hours. The reaction mass is then added dropwise with cooling to 250 ml water. The resulting mixture is then extracted with three volumes of diethylether and dried over anhydrous magnesium sulfate and concentrated. (Crude weight of reaction mass 48.3 grams).

The reaction mass is then distilled on a microvigreux column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 92/92 | 112/113 | 1/1 | 0.5 |
| 2 | 92 | 110 | 1 | 1.0 |
| 3 | 85 | 110 | 1 | 1.1 |
| 4 | 117 | 124 | 1 | 2.1 |
| 5 | 95/101 | 116/121 | 2/1 | 0.7 |
| 6 | 115 | 126 | 1 | 3.0 |
| 7 | 122 | 134 | 1 | 5.0 |
| 8 | 115 | 135 | 1 | 2.4 |
| 9 | 115 | 132 | 1 | 2.9 |
| 10 | 108 | 128 | 1 | 2.5 |
| 11 | 112 | 124 | 1 | 2.3 |
| 12 | 110 | 122 | 1 | 2.3 |

-continued

| Fraction Number | Vapor Temp. (°C.) | Liquid Temp. (°C.) | Pressure mm/Hg. | Weight of Fraction (grams) |
|---|---|---|---|---|
| 13 | 109 | 124 | 1 | 1.9 |
| 14 | 107 | 126 | 1 | 2.6 |
| 15 | 80 | 140 | 1 | 1.9 |
| 16 | 102 | 190 | 1 | 1.2 |
| 17 | 50 | 220 | 1 | 0.7 |

FIG. 11 is the GLC profile for the crude reaction product prior to work-up (referred to as "Crude A").

FIG. 12 is the GLC profile for the crude reaction product after work-up but prior to distillation (hereinafter referred to as "Crude B").

FIG. 13 is the GLC profile for fraction 17 of the foregoing distillation. (Conditions: 3'×⅛" 5% Carbowax column programmed at 70°–230° C. at 2° C. per minute). The peak indicated by reference numeral "20" is the peak for the mixture of compounds having the structures:

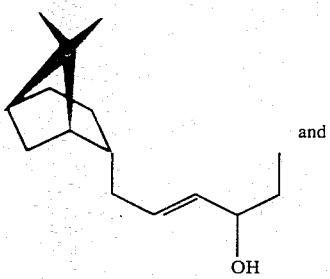

and

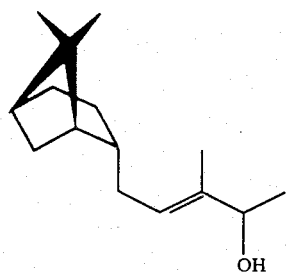

The peak indicated by reference numeral "21" is the peak for the compound having the structure:

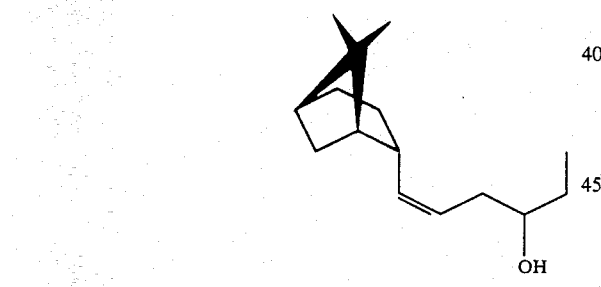

In addition, peaks on the GLC profile are indicative of the mixture of compounds defined according to the structure:

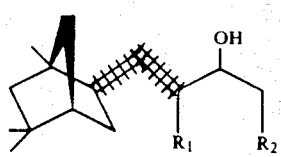

wherein one of $R_1$ or $R_2$ is methyl and the other of $R_1$ or $R_2$ is hydrogen; and wherein one of the lines:

is a carbon-carbon double bond and the other of the lines:

is a carbon-carbon single bond.

FIG. 14 is the NMR spectrum for the peak indicated by reference numeral "20" of FIG. 13 for the mixture of compounds defined according to the structures:

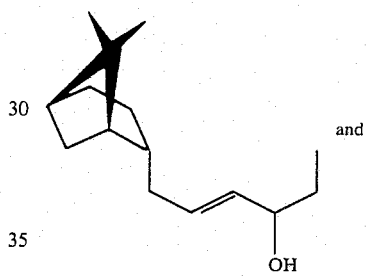

and

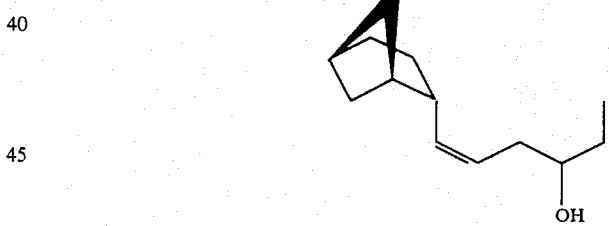

FIG. 15 is the NMR spectrum for the peak indicated by reference numeral "21" of the GLC profile of FIG. 13 for the compound having the structure:

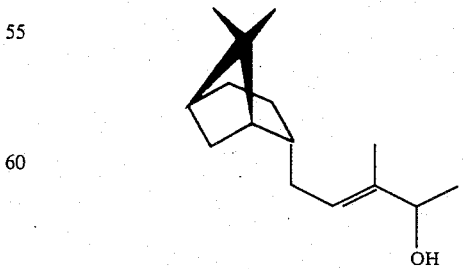

FIG. 16 is the infra-red spectrum for the mixture of compounds (fraction 17) of the distillation product of the reaction product of this example.

EXAMPLE V(A)

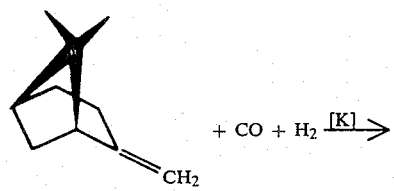
+ CO + H₂ —[K]→ wherein K represents the compound defined according to the structure:

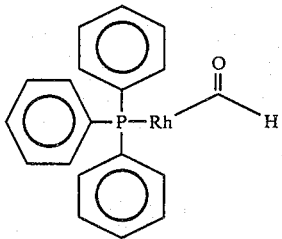

Into a 500 ml autoclave equipped for 1,000 psig pressure is placed 136 grams beta pinene; 0.5 grams of the catalyst defined according to the structure:

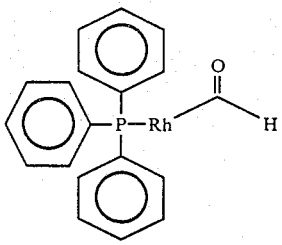

and 50 ml toluene. With stirring, the autoclave is closed and heated to 100° C. While maintaining the autoclave temperature at 100° C., a 1:1 mole ratio mixture of carbon monoxide and hydrogen is charged to the autoclave up to 1,000 psig pressure and the autoclave is maintained at 100° C. and 1,000 psig pressure for a period of 13.5 hours. During the 13.5 hour reaction period, the total pressure drop for the carbon monoxide:hydrogen mixture is 5180 psi. At the end of the 13.5 hour period, the autoclave is depressurized and opened.

The reaction mass is then washed with 500 ml of a 10% hydrochloric acid solution; followed by saturated sodium carbonate aqueous solution and then washed with water until neutral.

The reaction mass is then distilled yielding three fractions; the first fraction being all toluene and the second and third fractions containing 60.5 grams product as confirmed by GLC analysis.

The distillation yielded the following fractions:

| Fraction Number | Vapor Temp. (°C.) | Liquid Temp. (°C.) | Pressure mm/Hg. |
|---|---|---|---|
| 1 | 30 | 34 | 6 |
| 2 | 50 | 79 | 6 |
| 3 | 96 | 200 | 9 |

FIG. 17 is the GLC profile for the beta pinene reactant (conditions: SE-30 column programmed at 100°–200° C. at 8° C. per minute).

FIG. 18 is the GLC profile of the reaction product prior to distillation.

FIG. 19 is the GLC profile for fraction 3 of the foregoing distillation. The peak indicated by the reference numeral "52" is the peak for the compound defined according to the structure

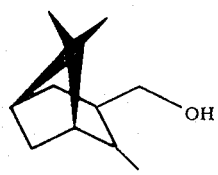

The peak indicated by the reference numeral "52" is for the compound having the structure:

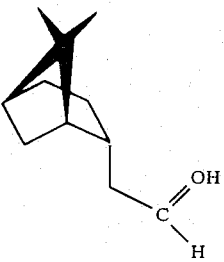

FIG. 20 is the NMR spectrum for the peak indicated by the reference numeral "52" of FIG. 19 for the compound having the structure:

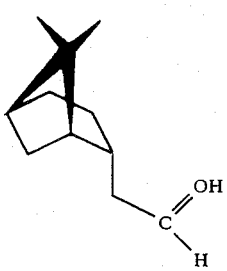

FIG. 21 is the infra-red spectrum for the compound of the peak indicated by reference numeral "52" of FIG. 19 for the compound having the structure:

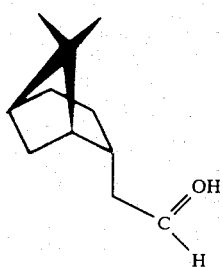

EXAMPLE V(B)

CONDENSATION OF METHYL ETHYL KETONE WITH 10-FORMYL PINANE

Reaction:

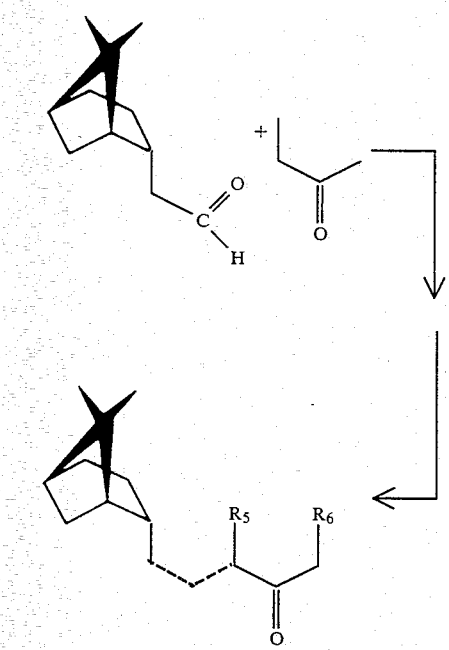

(wherein a mixture is produced wherein in the mixture one of the dashed lines is a carbon-carbon double bond in each of the compounds and the other of the dashed lines is a carbon-carbon single bond in other compounds; wherein one of $R_5$ and $R_6$ is hydrogen and the other of $R_5$ and $R_6$ is methyl in each of the compounds).

Into a one-liter reaction flask equipped with stirrer, addition funnel, thermometer and reflux condenser is added 220 ml methyl alcohol and 33 grams of potassium hydroxide. The resulting mixture is stirred until all of the potassium hydroxide is dissolved.

The reaction vessel is cooled to 10° C. and b 55 grams of 10-formyl pinane having the structure:

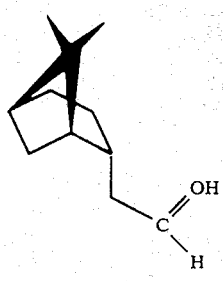

of fraction 3 of the distillation product of Example V(A) is added dropwise subsequent to being dissolved in an equal volume of methyl alcohol. After addition of the 10-formyl pinane, the reaction mass is allowed to reach room temperature (23° C.) and 72 grams of methyl ethyl ketone is added dropwise over a 1.5 hour period while maintaining the reaction mass at room temperature.

After addition of the methyl ethyl ketone, the reaction mass is heated to 45° C. and maintained at 45° C. with stirring for a 6 hour period.

The reaction mass is then cooled to room temperature and the reaction mass is diluted with about 550 ml of saturated sodium chloride solution yielding two phases; an organic phase and an aqueous phase. The organic phase is separated from the aqueous phase and the aqueous phase is extracted with four 100 ml portions of diethyl ether. The diethyl ether extracts are combined and washed three times with saturated sodium chloride solution until neutral. The resulting mixture is dried over anhydrous magnesium sulfate and the solvent is removed to yield 80.0 grams of crude product. This crude material primarily contains the compound defined according to the structure:

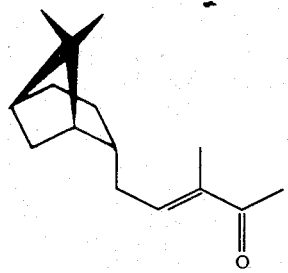

but is also a mixture which can be defined according to the structure:

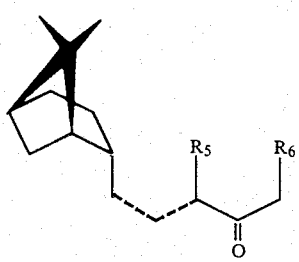

wherein in the mixture in each of the compounds, one of the dashed lines is a carbon-carbon double bond and the other of the dashed lines is a carbon-carbon single bond; and one of $R_5$ or $R_6$ is hydrogen and the other of $R_5$ or $R_6$ is methyl.

The resulting material is distilled on a 1' Vigreux column to yield 13 fractions thusly:

| Fraction Number | Vapor Temp (°C.) | Liquid Temp (°C.) | Pressure mm/Hg. | Weight of Fraction (grams) |
|---|---|---|---|---|
| 1 | 25/25 | 113/126 | 2/1 | 0.9 |
| 2 | 81 | 135 | 1 | 0.9 |
| 3 | 101 | 139 | 1 | 1.8 |
| 4 | 102 | 141 | 1 | 3.2 |
| 5 | 102 | 142 | 1 | 3.6 |
| 6 | 104 | 145 | 1 | 4.4 |
| 7 | 103 | 145 | 1 | 8.7 |
| 8 | 103 | 146 | 1 | 7.7 |
| 9 | 103 | 148 | 1 | 6.2 |
| 10 | 110 | 162 | 1 | 10.3 |
| 11 | 113 | 180 | 1 | 7.3 |
| 12 | 103 | 204 | 1 | 3.3 |
| 13 | 133 | 235 | 1 | 1.8 |

FIG. 22 is the GLC profile for fraction 6 of the foregoing distillation product. (Conditions: 10'×⅛" 5% Carbowax column programmed at 100°–220° C. at 4° C. per minute). The peak indicated by reference numeral "62" is for the compound defined according to the structure:

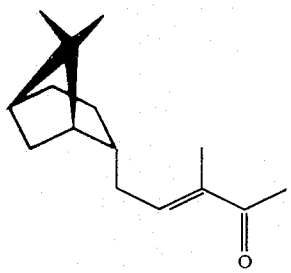

FIG. 23 is the NMR spectrum for the peak indicated by reference numeral "62" of FIG. 22 for the compound defined according to the structure:

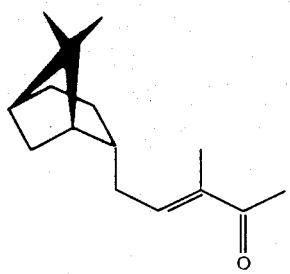

FIG. 24 is the infra-red spectrum for the compound of the peak indicated by reference numeral "62" of FIG. 22 for the compound having the structure:

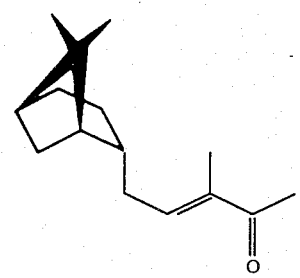

EXAMPLE VI

CHYPRE ESSENCE FORMULATIONS

The following Chypre essence compositions are prepared:

| Ingredients | VI(A) | VI(B) | VI(C) | VI(D) |
|---|---|---|---|---|
| Santalol | 60 | 60 | 60 | 60 |
| Coumarin | 70 | 70 | 70 | 70 |
| Musk ketone | 30 | 30 | 30 | 30 |
| Musk ambrette | 20 | 20 | 20 | 20 |
| Ambrain absolute | 25 | 25 | 25 | 25 |
| Tarragon oil | 25 | 25 | 25 | 25 |
| Angelica root oil | 5 | 5 | 5 | 5 |
| Clary sage | 30 | 30 | 30 | 30 |
| Vetiver oil | 60 | 60 | 60 | 60 |
| Linalool | 30 | 30 | 30 | 30 |
| Patchouli oil | 20 | 20 | 20 | 20 |
| Iso-eugenol | 35 | 35 | 35 | 35 |
| Methyl ionone | 50 | 50 | 50 | 50 |
| Oakmoss absolute | 60 | 60 | 60 | 60 |
| Bergamot oil | 225 | 225 | 225 | 225 |
| Jasmin absolute | 20 | 20 | 20 | 20 |
| Rose absolute | 15 | 15 | 15 | 15 |
| Methyl salicylate | 2 | 2 | 2 | 2 |
| Lavender oil | 3 | 3 | 3 | 3 |
| Vanillin | 15 | 15 | 15 | 15 |
| Heliotropin | 35 | 35 | 35 | 35 |
| Ylang oil, Manila | 70 | 70 | 70 | 70 |
| Cinnamyl acetate | 25 | 25 | 25 | 25 |
| Benzoin resinoid | 50 | 50 | 50 | 50 |
| Ketone produced according to Example IV, peak 15, having the structure: | 25 | 0 | 0 | 0 |

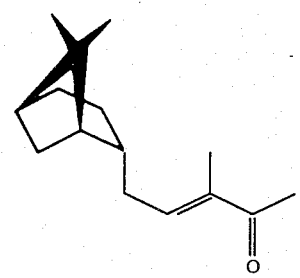

| | | | | |
|---|---|---|---|---|
| Mixture of ketones produced according to Example IV, bulked fractions 14–17 | 0 | 25 | 0 | 0 |
| Mixture of alcohols produced according to Example V, bulked fractions 6–14 | 0 | 0 | 25 | 0 |
| 4-methyl-3-cyclohexene-1-carboxylic acid prepared according to Example I of application for U.S. Letters Pat. Serial No. 299,211 filed on September 3, 1981 incorporated by reference herein | 0 | 0 | 0 | 25 |

The original mixture without the ketones produced according to Example IV or the alcohols produced according to Example VI and without the 4-methyl-3-cyclohexene-1-carboxylic acid was designed as a Chypre essence. The ketone of Example IV defined according to the structure:

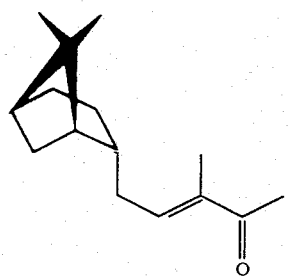

adds a powerful sandalwood, urine note with a sweet, floral, muguet undertone to this Chypre formulation. Thus, the Chypre formation of Example VI(A) can be described as "Chypre essence with powerful sandalwood, urine-like topnotes and sweet, floral muguet undertones".

The mixture of ketones produced according to Example IV, bulked fractions 14–17, imparts to this Chypre essence a woody, urine note with a buttery, caramel topnote. The Chypre essence produced according to Example VI(B) can be described as "a Chypre aroma with a woody, urine, buttery, caramel topnote profile".

The Chypre essence prepared according to Example VI(C) with the mixture of alcohols added has a "Chypre essence with a sandlewood, musky undertone".

The addition of the mixture of ketones of Example IV (bulked fractions 14–17)and 4-methyl-3-cyclohexene-1-carboxylic acid adds to this Chypre essence an intense, sandalwood, musky aroma profile as well as a natural, sweaty, leathery, cuminic, animal-like, cedar-like and castoreum undertone. Thus, the Chypre essence of Example VI(D) can be described as "a Chypre essence with a sandalwood and musky topnote profile and a natural, sweaty, leathery, cuminic-like, cedar-like and castoreum undertone profile".

EXAMPLE VII

WOODY AMBER FRAGRANCE

The following mixture is prepared:

| Ingredients | Parts By Weight | | |
|---|---|---|---|
| | VII(A) | VII(B) | VII(C) |
| Bergamot oil CP | 100 | 100 | 100 |
| Orange oil Fla. CP | 100 | 100 | 100 |
| Bitter orange oil WI | 50 | 50 | 50 |
| Lemon oil Cal. CP | 20 | 20 | 20 |
| Mandarin oil | 20 | 20 | 20 |
| Lime oil exp. WI | 10 | 10 | 10 |
| Ocimene | 10 | 10 | 10 |
| Ortho t-butyl cyclohexanyl acetate | 10 | 10 | 0 |
| Cedryl methyl ether | 50 | 50 | 50 |
| 4-methyl-3-cyclohexene-1-carboxylic acid | 0 | 50 | 50 |
| Mixtures of ketones prepared according to Example II, bulked fractions 2-7 | 40 | 40 | 0 |
| Mixture of alcohols prepared according to Example V, bulked fractions 6-14 | 0 | 0 | 40 |
| Mixtures of ketones having the structures: | | | |
| 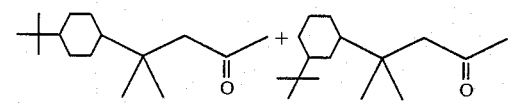 | | | |
| prepared according to Example II of U.S. Pat. No. 3,702,343 incorporated by reference herein | 20 | 20 | 0 |

The mixture of ketones produced according to Example II, bulked fractions 2–7, taken together with the mixture of ketones of U.S. Pat. No. 3,702,343 having the structures:

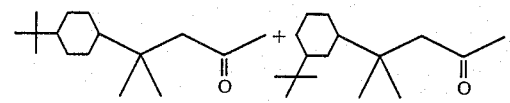

in Example VII(A) imparts to this woody, amber fragrance an intense, pleasant, animal, leathery, sweaty, urine, oriental-like unertone profile. Accordingly, the aroma of the fragrance of Example VII(A) can be described as "woody amber with an animal, leathery, sweaty, urine, oriental-like undertone profile".

The mixture of ketones of Example IV (bulked fractions 14–17) taken together with the 4-methyl-3-cyclohexene-1-carboxylic acid and the mixture of compounds defined according to the structure:

imparts to this woody amber formulation natural sweaty, leathery, cuminic, animal-like, castoreum-like, urine, oriental nuances in both the topnote and undertone areas. The overall aroma description of the perfume of Example VII(B) can be described as "woody amber with natural sweaty, leathery, cuminic, animal-like and castoreum-like topnotes and urine-like, animal-like and oriental undertones".

The mixture of alcohols of Example V (bulked fractions 6–14) taken together with the 4-methyl-3-cyclohexene-1-carboxylic acid imparts to this woody amber fragrance an intense, cumin-like, castoreum-like, sandalwood, musky topnote profile. Accordingly, the aroma of the perfume of Example VII(C) can be described as "a woody amber aroma with a sandalwood, musky, cumin-like, castoreum-like topnote profile".

EXAMPLE VIII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Structure of Product(s) and Example by which Produced | Aroma Discription |
|---|---|
| Reaction product of Example IV defined according to the structure:<br>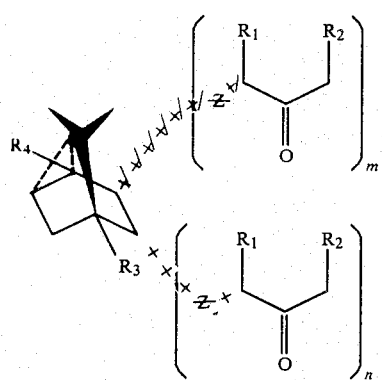<br>taken together with the mixture of compounds defined according to the structure:<br>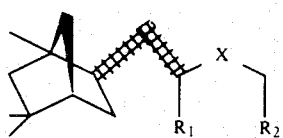<br>(mixture, bulked fractions 14–17). | A strong, woody, urine-like note with a a buttery, caramel topnote. |
| Compound defined according to the structure:<br>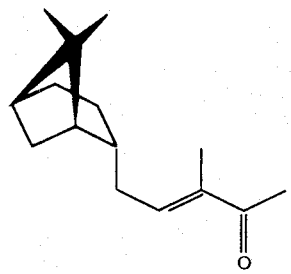<br>produced according to Example IV. | Powerful sandalwood aroma with urine, sweet, floral (muguet) undertone. |
| Mixture of compounds defined according to the structure:<br>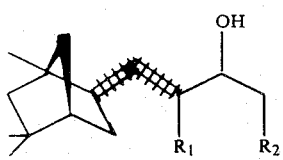<br>produced according to Example V. | A powerful intense, sandalwood aroma at 0.0001 ppm. |
| Mixture of compounds produced according to Example V, bulked fraction 6–14 defined according to the structure: | A sandalwood, musky aroma profile. |

TABLE II-continued

| Structure of Product(s) and Example by which Produced | Aroma Discription |
|---|---|
| taken together with the mixture of compounds defined according to the structure: | |
| Fragrance formulation of Example VI(A) | Chypre essence with powerful sandalwood, urine-like topnotes and sweet, floral muguet undertones. |
| Fragrance formulation of Example VI(B) | A Chypre aroma with a woody, urine, buttery, caramel topnote profile. |
| Fragrance formulation of Example VI(C) | Chypre essence with a sandalwood, musky undertone. |
| Fragrance formulation of Example VI(D) | A Chypre essence with a sandalwood and musky topnote profile and a natural, sweaty, leathery, cuminic-like, cedar-like and castoreum undertone profile. |
| Fragrance formulation of Example VII(A) | Woody amber with an animal, leathery, sweaty, urine, oriental-like undertone profile. |
| Fragrance formulation of Example VII(B) | Woody amber with natural, sweaty, leathery, cuminic, animal-like and castoreum-like topnotes ans urine-like, animal-like and oriental undertones. |
| Fragrance formulation of Example VII(C) | A woody amber aroma with a sandalwood, musky, cumin-like, castoreum-like topnote profile. |

EXAMPLE IX

PERFUMED LIQUID DETERGENTS

Concentrated liquid detergents (Lysine salt of n-dodecyl benzene sulfonic acid as more specifically described in U.S. Pat. No. 3,948,818, issued on Apr. 6, 1976 incorporated by reference herein) with aroma nuances as set forth in Table II of Example VIII, are prepared containing 0.10%, 0.15%, 0.20%, 0.25%, 0.30% and 0.35% of the substance set forth in Table II of Example VIII. They are prepared by adding and homogeneously mixing the appropriate quantity of substance set forth in Table II of Example VIII in the liquid detergent. The detergents all possess excellent aromas as set forth in Table II of Example VIII, the intensity increasing with greater concentrations of substance as set forth in Table II of Example VIII.

EXAMPLE X

PREPARATION OF COLOGNES AND HANDKERCHIEF PERFUMES

Compositions as set forth in Table II of Example VIII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VIII are imparted to the colognes and to the handkerchief perfumes at all levels indicated.

EXAMPLE XI

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table II of Example VIII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VIII.

EXAMPLE XII

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VIII. Each of the detergent samples has an excellent aroma as indicated in Table II of Example VIII.

EXAMPLE XIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table II of Example VIII.

Fabric softening compositions prepared according to Example I at column 15 of U.S. Pat. No. 3,632,396 having aroma characteristics as set forth in Table II of Example VIII supra, consist of a substrate coating having a weight of about three grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VIII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example VIII, supra.

EXAMPLE XIV

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. Eight grams of the polymer is dissolved in the alcohol. The following ingredients are added to the PVP/VA alcoholic solution:

| | |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example VIII supra | 0.10 weight percent |

The perfuming substances as set forth in Table I of Example VIII add aroma characteristics as set forth in Table I of Example VIII which are rather intense and aesthetically pleasing to the users of the soft-feel, good-hold pump hair sprays.

EXAMPLE XV

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ® 755 N polymer (manufactured by GAF Corporation of 140 West 51st Street, New York, N.Y.) (5.0 weight percent) is admixed with 0.1 weight percent sodium sulfite and 1.4 weight percent polyethylene glcyol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table II of Example VIII is added to the mixture. The resulting mixture is cooled to 40° C. and blending is carried out for an additional one hour in each case. At the end of this blending period, the resulting material has a pleasant fragrance as indicated in Table II of Example VIII.

EXAMPLE XVI

BASIC RASPBERRY FORMULATION

The following basic raspberry formulation is prepared:

| Ingredients | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

To the first portion of this basic formulation, a mixture of the ketones of Example IV is added at the rate of 1% (bulked fractions 10-20). To the second portion, nothing is added.

To a third portion of this basic formulation, a mixture of the compounds having the structures:

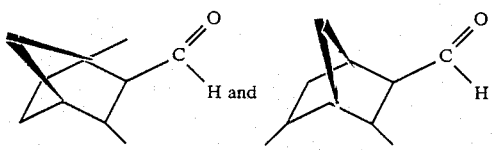

(produced according to Example II of the U.S. Pat. No. 4,284,824) is added at the rate of 1% and a mixture of the ketones produced according to Example IV supra (bulked fractions 10-20) is added at the rate of 1%. The three flavors are compared at the rate of 100 parts per million by a bench panel of experts.

The flavor containing the mixture of ketones produced according to Example IV (bulked fractions 10-20) is considered to have a more raspberry kernal, more seedy, herbaceous and more natural character in both armoa and taste than the flavor without such ketones. The use of the compounds having the structures:

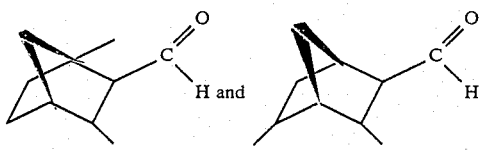

further enhances the raspberry kernel, seedy character.

EXAMPLE XVII

The following mixture is prepared:

| Ingredients | Parts by Weight |
| --- | --- |
| Natural raspberry concentrate | 2.5% |
| Raspberry juice | 85.0% |
| Sugar syrup (37.5° Baume) | 12.5% |

The ripened raspberry and seedy raspberry kernal note of this raspberry juice is imparted in increased strength by the addition of the mixture of ketones (bulked fractions 10-20) prepared according to Example IV at the rate of from 0.01 ppm up to 10 ppm.

EXAMPLE XVIII

To the raspberry formulation as set forth in Example XVI, the mixture of ketones produced according to Example IV (bulked fractions 10-20) is added at the rate of 0.2%. This material is then called the "test composition". The raspberry formulation without the mixture of ketones is called the "control composition".

The test and control compositions are added to the food products described hereinafter in the proportions shown for 10 kilograms of material to be flavored:
Pudding: 5-10 grams (0.05-0.1%)
Cooked sugar: 15-20 grams (0.15-0.2%)
Cooked sugar—100 ml of sugar syrup (prepared by dissolving 1 kilogram of sucrose in 600 ml of water) and 20 grams of glucose are mixed together and slowly heated to 145° C. The flavor is added and the mass is allowed to cool and harden.

Pudding—to 500 ml of warmed milk are added with stirring a mixture of 60 grams sucrose and 3 grams of pectin. The mixture is boiled for a few seconds and the flavor is added. The mixture is allowed to cool.

The finisihed foodstuff samples are tested by a panel of trained persons who express their views about the flavor of the samples. All members of the panel prefer the test samples having a more distinguished ripened raspberry aroma with taste of the ripe raspberries and its seedy kernel note.

An improved effect occurs when a mixture of 25:25:50 of 2-(4-hydroxy-4-methylpenthyl)-norbornadiene:compound having the structure:

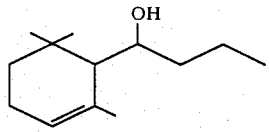

mixture of ketones produced according to Example IV (bulked fractions 10-20) at the rate of 0.02 parts per million up to about 10 parts per million.

EXAMPLE XIX

A. Powder Flavor Composition

Twenty grams of the flavor composition of Example XVI containing the mixture of ketones of Example IV (bulked fractions 10-20) is emulsified in a solution containing 300 grams gum acacia and 700 grams of water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid raspberry flavor of Example XVI containing mixture of ketones prepared according to Example IV (bulked fractions 10-20) | 20 |
| Propylene glycol | 9 |
| Cab—O—Sil ® M-5 (Brand of silica produced by the Cabot Corporation of 125 High Street, Boston, Mass. 02112: Physical properties: Surface area: 200 m²/gm Nominal particle size: 0.012 microns Density: 2.3 lbs/cu. ft.) | 5 |

The Cab-O-Sil ® is dispersed in the liquid raspberry flavor composition of Example XVI with vigorous stirring thereby resulting in a viscous liquid. 71 parts by weight of the powder flavor composition of Part A, supra, is then blended into the said viscous liquid with stirring at 25° C. for a period of 30 minutes resulting in a dry, free-flowing, sustained release raspberry flavor powder.

EXAMPLE XX

Ten parts by weight of 5-Bloom pigskin gelatin is added to ninety parts by weight water at a temperature of 150° F. The mixture is agitated until the gelatin is completely dissolved and the solution is cooled to 120° F. Twenty parts by weight of the liquid raspberry flavor composition of Example XVI (containing the mixture of ketones produced according to Example IV, bulked fractions 10-20) is added to the solution which is then homogenized to form an emulsion having particle size typically in the range of 2-5 microns. This material is kept at 120° F. under which conditions the gelatin will not gel.

Coacervation is induced by adding, slowly and uniformly, 40 parts by weight of a 20% aqueous solution of sodium sulphate. During coacervation, the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting gelled coacervate may be filtered and washed with water at temperatures below the melting point of gelatin, to remove the salt.

EXAMPLE XXI

CHEWING GUM 100 parts by weight of chicle are mixed with 4 parts by weight of the flavor prepared in accordance with Example XIX(B). 300 parts of sucrose and 100 parts of corn syrup are added. Mixing is effected in a ribbion blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting raspberry flavor.

EXAMPLE XXII

CHEWING GUM 100 parts by weight of chicle are mixed with 18 parts by weight of the flavor prepared in accordance with Example XX. 300 parts of sucrose and 100 parts of corn syrup are added. Mixing is effected in a ribbon blender with jacketed walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long-lasting raspberry flavor.

EXAMPLE XXIII

TOOTHPASTE FORMULATION

The following separate groups of ingredients are prepared:

| Parts by Weight | Ingredient |
| --- | --- |
| Group "A" | |
| 30.200 | Glycerine |
| 15.345 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example XIX(B) |

Procedure:

1. The ingredients in Group "A" are stirred and heated in a steam jacketed kettle to 160° F.
2. Stirring is continued for an additional three to five minutes to form a homogeneous gel.
3. The powders of Group "B" are added to the gel while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized and finally tubed.

The resulting toothpaste, when used in a normal toothbrushing procedure yields a pleasant raspberry flavor of constant strong intensity throughout said procedure (1-1.5 minutes).

EXAMPLE XXIV

CHEWABLE VITAMIN TABLETS

The flavor material produced according to the process of Example XIX(B) is added to a chewable vitamin tablet formulation at the rate of 10 grams/kilogram which chewable vitamin tablet formulation is prepated as follows:

In a Hobart Mixer, the following materials are blended to homogeneity:

|  | Gms/1000 Tablets |
|---|---|
| Vitamin C (ascorbic acid) as ascorbic acid-sodium ascorbate mixture 1:1 | 70.000 |
| Vitamin B$_1$ (thiamine mononitrate as Rocoat ® thiamine mononitrate 33⅓% (Hoffman LaRoche) | 4.000 |
| Vitamin B$_2$ (riboflavin) as Rocoat ® riboflavin 33⅓% | 5.000 |
| Vitamin B (pyridoxine hydrochloride) as Rocoat ® pyridoxine hydrochloride 33⅓% | 4.000 |
| Niacinamide as Rocoat ® niacinamide 33⅓% | 33.000 |
| Calcium pantothenate | 11.500 |
| Vitamin B$_{12}$ (cyanocobalamin) as Merck 0.1% in gelatin | 3.500 |
| Vitamin E (dl-alpha tocopheryl acetate) as dry Vitamin E acetate 33⅓% Roche d-biotin | 6.600 |
| Flavor of Example XIX(B) | 0.114 (as indicated above) |

|  | Gms/100 Tablets |
|---|---|
| Certified lake color | 5.000 |
| Sweetener - sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong raspberry flavor for a period of 12 minutes.

EXAMPLE XXV

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn syrup | 60.0 |
| Licorice | 10.0 |
| Glycerine | 20.0 |
| Fig juice | 4.6 |
| Prune juice | 5.0 |
| Flavoring material of Example XIX(B) | 0.4 |

The resultant product is redried to a moisture content of 20%. On chewing, this tobacco has an excellent substantially consistent, long-lasting, licorice/raspberry flavor profile in conjunction with the tobacco note.

EXAMPLE XXVI

GUAVA NECTAR FLAVOR

At the rate of 0.02 parts per million to natural guava nectar is added a mixture of the alcohols prepared according to Example V (bulked fractions 1-17). The mixture of alcohols adds to the guava aroma and taste profile interesting musky, fruity, ionone and perfumy aroma characteristics with lactonic flavor characteristics causing the guava nectar to be much more natural-like having interesting "peachy" nuances.

EXAMPLE XXVII

PAPAYA NECTAR COMPOSITION

To natural papaya nectar is added the following materials:

| i. | natural lemon juice | 0.5% |
| ii. | mixture of alcohols prepared according to Example V, bulked fractions 5-17 | 0.5 ppm |

The addition of the mixture of alcohols prepared according to Example V adds to this papaya nectar a very natural "fruity" lactonic aroma and taste profile making it much more aesthetically pleasing than the papaya nectar without the addition of the mixture of alcohols.

EXAMPLE XXVIII

The following flavor formulation is prepared:

| Ingredients | Parts by Weight |
|---|---|
| Mixture of alcohols prepared according to Example V, bulked fraction 6-17 | 4 |
| 2-methyl-4-n-propyl oxathiane | 3 |
| Natural mango extract | 4 |

The resulting mixture is added to processed mango juice at the rate of 10 ppm. The resulting mango juice has an excellent "natural", fresh, fruity "unprocessed" flavor and is therefore preferred over "processed mango juice".

EXAMPLE XXIX

TOBACCO FORMULATIONS

Tobacco mixtures are produced by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |
| The following flavor formulation is prepared: | |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |

| -continued | |
|---|---|
| Water | 41.90 |

The above stated tobacco formulations are applied at the rate of 1.0% to all of the cigarettes produced using the above tobacco formulation. The cigarettes are then treated with 500 or 1,000 ppm of substances produced according to Examples IV or V as set forth in Table III below. The control cigarettes in each case not containing any methyl substituted pinyl oxopentenes produced according to Examples IV or V in the experimental cigarettes which contain the methyl substituted pinyl oxopentenes produced according to Examples IV or V are evaluated by paired comparison and the results are set forth in Table III below.

TABLE III

| Composition | Evaluation in smoking tobacco prior to and on smoking |
|---|---|
| Reaction product of Example IV defined according to the structure:<br />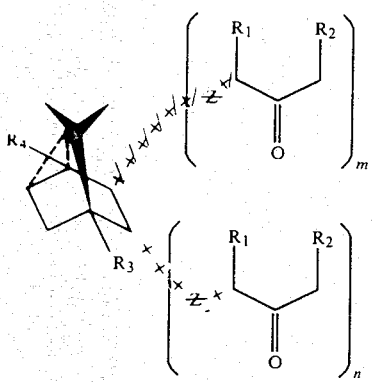 | A woody, sweet, oriental, raspberry, ionone-like aroma and taste prior to smoking with a woody, sweet, oriental ionone-like taste on smoking in the main stream and the side stream. |
| taken together with the mixture of compounds having the structure:<br />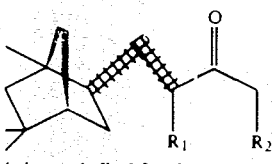<br />(mixture, bulked fractions 14–17). | |
| Mixture of compounds produced according to Example V, bulked fractions 6–14 defined according to the structure:<br />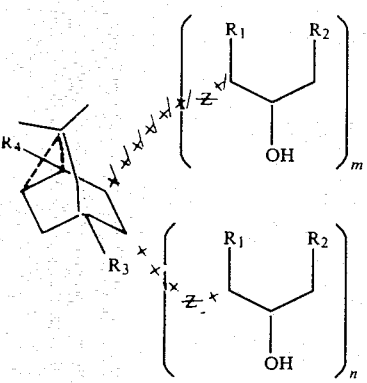<br />taken together with the compounds defined according to the structure: | A woody, sandalwood, patchouli-like, cigar box-like aroma and taste profile both prior to and on smoking in the main stream and the side stream. |

TABLE III-continued

| Composition | Evaluation in smoking tobacco prior to and on smoking |
|---|---|
| 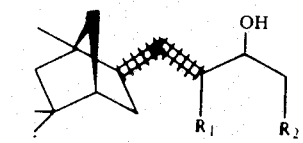 | |

All cigarettes are evaluated for smoke flavor with a 20 mm cellulose acetate filter.

What is claimed is:

1. A compound defined according to the generic structure:

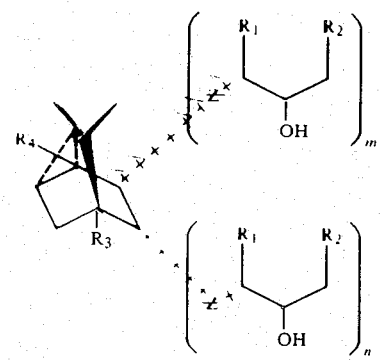

or the generic structure:

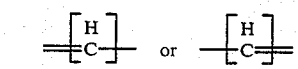

wherein Z represents methylidene defined according to the structure:

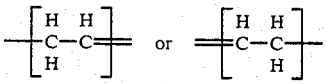

or ethylidene defined according to the structure:

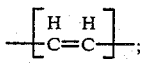

or ethylenyl defined according to the structure:

$$-\left[\begin{array}{cc} H & H \\ C=C \end{array}\right]-;$$

wherein one of the dashed lines represents a carbon-carbon single bond and the other of the dashed lines represents no bond; wherein n is 0 or 1 and m is 0 or 1 with the sum of n+m being equal to 1; wherein $R_1$, $R_2$, $R_3$ and $R_4$ represent hydrogen or methyl; wherein one of the lines:

++++ represents a carbon-carbon single bond and the other of the lines:

++++ represents a carbon-carbon single bond or a carbon-carbon double bond; wherein one of the lines:

/+/+/+/+/+/ represents a carbon-carbon single bond and the other of the lines:
/+/+/+/+/ represents a carbon-carbon single bond or a carbon-carbon double bond; with the provisos that:
(i) when $R_3$ and $R_4$ are each hydrogen, the dashed line at the 7-5 position is a carbon-carbon single bond; n=0 and m is 1; Z represents ethylidene having the structure:

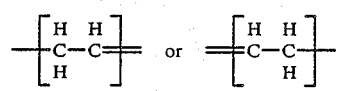

or ethylenyl having the structure:

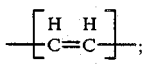

(ii) when one of $R_3$ or $R_4$ is methyl, then either the dashed line at the 7-5 position or the dashed line at the 7-4 position is a carbon-carbon single bond; and Z represents methylidene defined according to the structure:

(iii) when $R_3$ is methyl, then n is 1 and m is 0 and $R_4$ is hydrogen; and
(iv) when $R_4$ is methyl, then $R_3$ is hydrogen, n is 0 and m is 1 and wherein one of the lines:

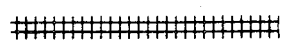

is a carbon-carbon double bond and the other of the lines:

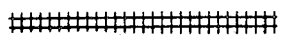

is a carbon-carbon single bond.

2. A compound defined according to claim 1 having a structure selected from the group consisting of:

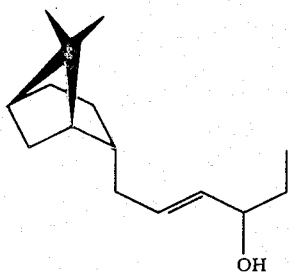

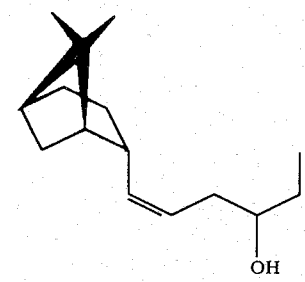

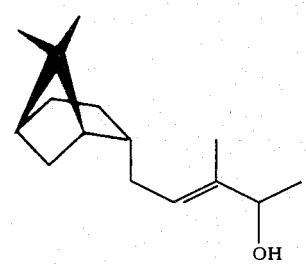

the structure:

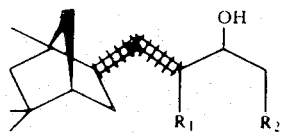

wherein one of $R_1$ or $R_2$ is methyl and the other of $R_1$ or $R_2$ is hydrogen; and wherein one of the lines:

is a carbon-carbon double bond and the other of the lines:

is a carbon-carbon single bond.

3. A compound defined according to claim 1 wherein the structure of the compounds are selected from the group consisting of:

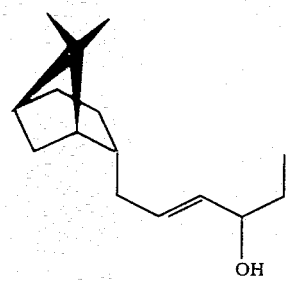
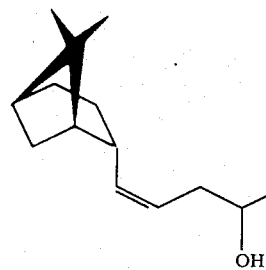 and
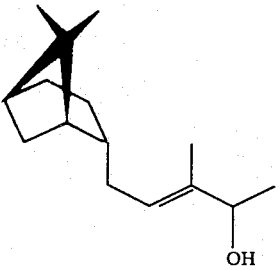
4. A mixture of compound defined according to the structures:
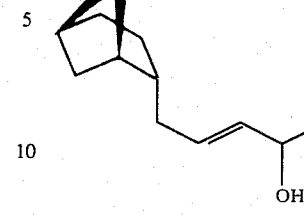
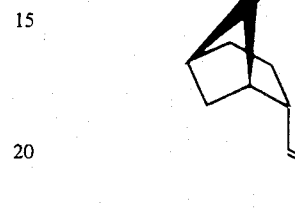
 and
the compounds defined according to the genus:
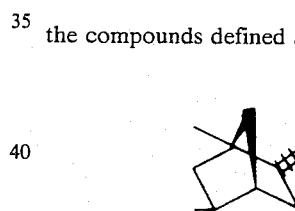
wherein one of $R_1$ or $R_2$ is methyl and the other of $R_1$ or $R_2$ is hydrogen; and wherein one of the lines:
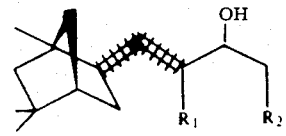
is a carbon-carbon double bond and the other of the lines:
is a carbon-carbon single bond.
* * * * *